US011001625B2

(12) United States Patent
Shoemaker

(10) Patent No.: US 11,001,625 B2
(45) Date of Patent: May 11, 2021

(54) VHH BASED BINDING ANTIBODIES FOR ANTHRAX AND BOTULINUM TOXINS AND METHODS OF MAKING AND USING THEREFOR

(71) Applicant: TUFTS UNIVERSITY, Boston, MA (US)

(72) Inventor: Charles B. Shoemaker, Boston, MA (US)

(73) Assignee: Tufts University, Medford, MA (US), Trustees of Tufts College ( * ) Notice: Subject to any disclaimer, the term of this patent is extended or adjusted under 35 U.S.C. 154(b) by 82 days.

(21) Appl. No.: 15/534,776

(22) PCT Filed: Dec. 10, 2015

(86) PCT No.: PCT/US2015/064872
§ 371 (c)(1),
(2) Date: Jun. 9, 2017

(87) PCT Pub. No.: WO2016/094602
PCT Pub. Date: Jun. 16, 2016

(65) Prior Publication Data
US 2017/0362310 A1  Dec. 21, 2017

Related U.S. Application Data

(60) Provisional application No. 62/089,949, filed on Dec. 10, 2014.

(51) Int. Cl.
*C07K 16/12* (2006.01)
*A61K 39/00* (2006.01)

(52) U.S. Cl.
CPC ...... *C07K 16/1282* (2013.01); *C07K 16/1278* (2013.01); *C12Y 304/24069* (2013.01); *C12Y 304/24083* (2013.01); *A61K 2039/505* (2013.01); *C07K 2317/31* (2013.01); *C07K 2317/569* (2013.01); *C07K 2317/76* (2013.01); *G01N 2333/952* (2013.01); *G01N 2333/954* (2013.01)

(58) Field of Classification Search
None
See application file for complete search history.

(56) References Cited

U.S. PATENT DOCUMENTS

| 10,202,441 | B2 | 2/2019 | Shoemaker |
| 10,766,950 | B2 * | 9/2020 | Shoemaker ........ C07K 16/1228 |
| 2006/0149041 | A1 | 7/2006 | Silence |
| 2013/0058962 | A1 | 3/2013 | Shoemaker et al. |
| 2016/0368972 | A1 | 12/2016 | Shoemaker |
| 2019/0225675 | A1 | 7/2019 | Shoemaker |

FOREIGN PATENT DOCUMENTS

| CN | 103866401 A | 6/2014 |
| WO | 2015100409 A1 | 7/2015 |

OTHER PUBLICATIONS

Abaza et al. J. Protein Chem. 11: 433-444, 1992.*
Skolnick et al. Trends in Biotechnology 18: 34-39, 2000.*
Li et al. PNAS 77: 3211-3214, 1980.*
Lederman et al. Mol. Innnnunol. 28: 1171-1181, 1991.*
Colman et al. Res. Innnnunol. 145: 33-36, 1994.*
International Search Report and Written Opinion for corresponding PCT/US2015/064872, dated Apr. 15, 2016 (10 pages).
English Machine Translation (Google Patents) of CN 103866401 (13 pages).

* cited by examiner

*Primary Examiner* — Sarvamangala Devi
(74) *Attorney, Agent, or Firm* — Melissa Hunter-Ensor; Leslie Serunian; Greenberg Traurig, LLP

(57) ABSTRACT

Methods, compositions and kits are provided for treating a subject exposed to or at risk for exposure to a disease agent, methods, compositions and kits having a pharmaceutical composition including at least one recombinant binding protein or a source of expression of the binding protein, wherein the binding protein neutralizes at least one or a plurality of disease agents that are toxins, for example at least one of a Botulinum toxin or an Anthrax toxin.

7 Claims, 10 Drawing Sheets

Specification includes a Sequence Listing.

```
                    CDR1                              CDR2                                                                      CDR3
JHD-B6   SGGG-LVQPGGSLRLSCAASGS-SESRYAMRWYRQAPGKQRELVANINSRGTSN-YADSVKGRFTISRDNAKNTVYLQMNSLKPEDTAVYYCNAEW----------LGRSEPSWGQGTQVTVSS    (lh)
JHE-D9   SGGG-LVQPGGSLRLSCAASGF-IFSLYTMRWHRQAPGKERELVATITSATGITNYADSVKGRFIISRDDAKKTGYLQMNSLKPEDTAVYYCNAVR----------TTVSRDYWGQGTQVTVSS    (lh)
JIJ-A12  SGGG-LVQPGGSLRLSCAASGI-IFSIYTMGWYRQAPGKQRELVAAIPSGEPSAN-ATDSVGGRFTITRDNAENTVYLQMNDLKPEDTAVYYCNARR----------GPGIKNYWGQGTQVTVSS    (lh)
JIJ-B8   SGGG-LVQPGGSLSVSCAASGS-IARPGAMAWFRQAPGKERELVASITPGGLIN-YADSVTGRFTISRDNAKTVYLQMNSLQPEDTAVYYCHARI----------IPLGLGSEYRDHWGQGTQVTVSS  (sh)
JIJ-D3   TGG--LVQPGGSLRLSCAASGL-TFSSTAMAWFRQAPGKQRELVAISGAGITYYDSDVKGRFTISRNNVENTVYLQMNSLKTEDTAVYYCAARR----------NTYISDYNIPARYPWGQGTQVTVSS  (lh)
JIJ-E9   TGG--LVQPGGSLRLSCAASRSYTATIYSMWRWFRQAPGKQRELVAGMTSDGQTN-YATSVKGRFTISDAKNTVYLLNNSLKLEDTAVYYCVAP---------WRLQGWDYWGQGTQVTVSS        (lh)
JIJ-F11  SGGG-LVQPGGSLRLSCAAPES-IVNSRTMAWYRQAPGKQRORERVATITTAGSPN-YADSVKGREAISRDNAKNTVYLQMNSLKPEDTAVYYCNTLL----------STLPIQGQGTQVTVSS       (sh)
JIK-B8   SGGG-LVQPGGSLGLSCVVASERSIRNYGWGWYRQAPGKQRELVAQISSGGTTN-YADSVEGRFTISRDNVKMVHLQVNSLKPEDTAVYYCNSLL----------RTFSNGQGTQVTVSS           (lh)
JIK-B10  TGGG-LVQPGGSLRLSCAASGF-TFSSYRMSWYRQAAGKERDVVATITNANGVPTGYADSVKGREFVATISRSSAIREYADSVKGRFTISRDGAKNTVLEANSLNPEDTAVYYCNAPR----------LHTSVGYWGQGTQVTVSS  (lh)
JIK-B12  SGGG-LVQAGNSLRLSCTASGV-IFSIYTMGWFRQAPGKEREFVAAIGVADGTALIVADSVTGRFTISRSSAIREYADSVKGRFTISRDGAKNTVLEANSLKPEDTAVYYSCAAYL----SPRVQSPYITDSRVQLWGQGTQVTVSS  (lh)
JIK-F4   TGGG-LVQAGGSLRLSCAASGR-----YAMGWFRQAPGKEREFVATISRSSAIREYADSVKGRFTISRDGAKNTVYAEPLKGRFAISRDNDKNALYLQMNSLKPEDTALYYCAEGR--GATFNPEYAYWGQGTQVTVSS          (lh)
JKH-A4   TGGG-LVQAGGSLRLSCAASGL-TFGNYAMGWFRQAPGKEREFVASIGWTDDNTYYGDSVKGRFTISRSGSNTWYAEPLKGRFAISRDNDKNALYLQMNSLKPEDTAVYYCAGGS----YNSDWMNTMTWGQGTQVTVSS          (sh)
JKH-C7   SGGGGLVQAGGSLVQAGGSLRLSCAASGR-TFSGYAMGWFRQAPGKEREFVADISWSGHNTYYGDSVKGRFTISRDTAKNTVYLQMSLKPEDTAVYYCAAREGARTHLSDSYFPGLMAEPPVGYWGQGTQVTVSS  (lh)
JKH-D12  TGGG-LVQPGGSLRLSCAASGR-TFTSYYIGWFRQEDPGPGKEREFVASIGWTDDNTYYADSVKGRFTISRDNAETTAYLQMSGLKPEDTAVYYCAADY----------GSGIRAWINWIYWGQGTQVTVSS    (lh)
JKM-A6   TGGG-LVQPGGSLRLSCAASGA-TLDTYIITMFRQAPGKERRAVSCINRSGSTT-YSDSVKGRFTISRDNAQKTVYLQMNSLNPEDTAIYYCAADA----------SYRTCGGSMWNAYWGQGTQVTVSS    (lh)
JKO-A4   SGGG-SVQPGGSLRLSCAASGF-TFSSYMSWVRQAPGKGIEWVSDINGGGKDTYADSVKGRFTISRDNARNTLYLQMNSLQPEDTAVYYCAKDL----------SYVSGTYFANDWGQGTQVTVSS        (lh)
JKO-B8   SGGG-LVQPGGSLRLSCTASGI-IFDYYSVDWTVRQAPGKERELVATITGDGSPN-YADSVKGRFTISRDNAKKTVYLQMNSLKTEDTAVYYCHAR----------TIGTKSEYWGQGTQVTVSS        (lh)
JKO-E12  TGGG-LVQAGGSLRLSCLASRM-SESRREMAWYRQAPGKQRERVATISSFGDTNYTDSVEGRFTISRDNAKNTMVLQMNSLKPDDTAVYYCNTLL----------ATYAWGQGTQVTVSS              (lh)
JKO-H2   SGGG-LVQAGGSLRLSCAASGR-TFSSYMGWFRQAPGKEREFVAAISRNGGKTYYADSVKGRFTISRDGTENTVYLQMNSLKPEDTAVYYCAAAV----------AASAEFVTARSNFYEYWGQGTQVTVSS  (lh)
```

(sh) indicates short hinge
(lh) indicates long hinge

MSDKIIHLTDDSFDTDVIKADGAILVDFWAEWCGPCKMIAPILDEIADEYQGKLITVAKLNIDQNPGTAPKYGIRGIPTLLLFKNGEVAATKVGALSKGQLKEFLDA
NLAGSGSGHMHHHHHHSSGLVPRGSGMKETAAAKFERQHMDSPDLGTDDDKAMAISDPNS///GAPVPYDPLEPR///AAAQVQLAESGGGLVQPGGSLGLSCV
VASERSINNYGMGWYRQAPGKQRELVAQISSGGTTNYADSVEGRFTISRDNVKMVHLQVNSLKPEDTAVYYCNSLLRTFSWGQGTQVTVSSEPKTPKPQAIA///
GGGGSGGGGSGGGGS///ILQGQVQLVESGGGLVQPGGSLSVSCAASGSIARPGAMAWYRQAPGKERELVASITPGGLTNYADSVTGRFTISRDNAKRTVYLQMNSL
QPEDTAVYYCHARIIPLGLGSEYRDHWCGQTQVTVSSAHHSEDPSARQ///GAPVPYDPLEPR///GGGS///DICLPRWGCLWED*

Figure 4B

MSDKIIHLTDDSFDTDVIKADGAILVDFWAEWCGPCKMIAPILDEIADEYQGKLITVAKLNIDQNPGTAPKYGIRGIPTLLLFKNGEVAATKVGALSKGQLKEFLDA
NLAGSGSGHMHHHHHHSSGLVPRGSGMKETAAAKFERQHMDSPDLGTDDDKAMAISDPNS///GAPVPYDPLEPR///AAAQVQLAESGGGLVQPGGSLGLSCV
VASERSINNYGMGWYRQAPGKQRELVAQISSGGTTNYADSVEGRFTISRDNVKMVHLQVNSLKPEDTAVYYCNSLLRTFSWGQGTQVTVSSEPKTPKPQAIA///
GGGGSGGGGSGGGGS///ILQGQVQLAESGGGGLVQAGGSIRLSCAASGRTFSGYAMGWFRQAPGKEREFVADISWSGHNTYYGDSVKGRFTISRDTAKNTVYLQMN
SLKPEDTAVYYCAAEGARTHLSDSYYFPGLWAEPPVGYWGQGTQVTVSSEPKTPKPQPARQ///GAPVPYDPLEPR///GGGS///DICLPRWGCLWED*

| Protein | Clone | K_D (nM) | EC₅₀ (nM) | IC₅₀ (nM) | C-group | Comments |
|---|---|---|---|---|---|---|
| JHD-B6 | JHP-18 | 66 +/- 2 | 0.5 | 10 | 1 | |
| JHE-D9 | JHP-25 | 13 +/- 1 | 5 | N/A | 1 | Non-neutralizing |
| JIJ-A12 | JIX-2 | 45 +/- 8 | 2 | N/A | 1 | Non-neutralizing |
| JIJ-B8 | JJS-2 | 8 +/- 8 | 0.4 | N/A | 2 | Non-neutralizing |
| JIJ-D3 | JIX-7 | 18 +/- 0.7 | 0.3 | 9 | 1 | |
| JIJ-E9 | JIX-10 | 12 +/- 1 | 0.4 | 30 | 1 | |
| JIJ-F11 | JIX-15 | 200 +/- 20 | 20 | N/A | 1 | Non-neutralizing |
| JIK-B8 | JIX-20 | 0.13 +/- 0.06 | 0.2 | 1 | 1 | |
| JIK-B10 | JIX-26 | 9 +/- 1 | 0.2 | 8 | 1 | |
| JIK-B12 | JIX-31 | 12 +/- 3 | 0.3 | 6 | 1 | |
| JIK-F4 | JIX-37 | 7 +/- 1 | 0.2 | 3 | 1 | |
| JKH-A4 | JKT-1 | 9 ± 0.5 | 0.5 | N/A | 2 | Non-neutralizing |
| JKH-C7 | JKT-3 | 7 ± 2 | 2 | 5 | 3 | |
| JKH-D12 | JKT-5 | 1 ± 0.4 | 0.3 | N/A | 2 | Non-neutralizing |
| JKM-A6 | JKT-8 | 20 ± 5 | 0.3 | N/A | 2 | Non-neutralizing |
| JKO-A4 | JKT-10 | 10 ± 2.2 | 0.3 | N/A | 2 | Non-neutralizing |
| JKO-B8 | JKT-11 | 200 ± 70 | >100 | N/A | 1 | Non-neutralizing |
| JKO-E12 | JKT-13 | 0.2 ± 0.07 | 0.1 | 0.2 | 1 | |
| JKO-H2 | JKT-15 | 4 ± 1 | 0.6 | N/A | 4 | Poor binding to PA63 |
| VNA1-PA | JKD-11 | ND | ND | 0.5 | | JIK-B8+ JIJ-B8 |
| VNA2-PA | JKU-1 | 0.07 | 1.0 | 0.5 | | JIK-B8+ JKH-C7 |

Figure 6

SEQUENCE LISTING

<160> NUMBER OF SEQ ID NOS: 259

<210> SEQ ID NO 1
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Ala Glu Thr Gly Gly Gly Leu Val Gln Ala Gly Gly
1               5                   10                  15

Ser Leu Arg Leu Ser Cys Ser Ala Ser Gly Leu Thr Phe Gly Asn Tyr
                20                  25                  30

Ala Met Gly Trp Phe Arg Gln Ala Pro Gly Lys Glu Arg Glu Phe Val
            35                  40                  45

Ala Ser Ile Ser Arg Ser Gly Ser Asn Thr Trp Tyr Ala Glu Pro Leu
        50                  55                  60

Lys Gly Arg Phe Ala Ile Ser Arg Asp Asn Asp Lys Asn Ala Leu Tyr
65                  70                  75                  80

Leu Gln Met Asn Ser Leu Lys Pro Glu Asp Thr Ala Val Tyr Tyr Cys
                85                  90                  95

Ala Gly Gly Ser Tyr Asn Ser Asp Trp Trp Asn Tyr Met Tyr Trp Gly
            100                 105                 110

Gln Gly Thr Gln Val Thr Val Ser Ser Glu Pro Lys Thr Pro Lys Pro
        115                 120                 125

Gln

<210> SEQ ID NO 2
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
caggtgcagc tggcggagac ggggggagga ttggtgcagg ctgggggctc gctgagactc      60
tcctgttcag cctctgggct caccttcggg aactatgcca tggctggtt ccgccaggct     120 ccagggaagg agcgtgagtt tgtagcatct atttctcgga gtggtagtaa cacatggtat    180
gcagaacccc tgaagggccg attcgccatc tccagagaca cgacaagaa cgcgctctat    240 ctgcaaatga acagcctgaa acctgaggac acggccgttt attactgtgc tggaggatct    300
tataatagtg actggtggaa ctatatgtac tggggccagg ggacccaggt cactgtctcc    360
tcagaaccca agacaccaaa accacaa                                       387

<210> SEQ ID NO 3
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

-continued

Gln Val Gln Leu Val Glu Ser Gly Gly Gly Leu Val Gln Ala Gly
1               5                   10                  15

Gly Ser Leu Arg Leu Ser Cys Ala Ala Ser Gly Arg Thr Phe Ser Gly
            20                  25                  30

Tyr Ala Met Gly Trp Phe Arg Gln Ala Pro Gly Lys Glu Arg Glu Phe
        35                  40                  45

Val Ala Asp Ile Ser Trp Ser Gly His Asn Thr Tyr Tyr Gly Asp Ser
50                  55                  60

Val Lys Gly Arg Phe Thr Ile Ser Arg Asp Thr Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Glu Gly Ala Arg Thr His Leu Ser Asp Ser Tyr Tyr Phe
            100                 105                 110

Pro Gly Leu Trp Ala Glu Pro Val Gly Tyr Trp Gly Gln Gly Thr
        115                 120                 125

Gln Val Thr Val Ser Ser Glu Pro Lys Thr Pro Lys Pro Gln
    130                 135                 140

<210> SEQ ID NO 4
<211> LENGTH: 426
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
caggtgcagc tggtggagtc gggtggggga ggactggtgc aggctggggg ctctctgaga      60
ctctcctgtg cagcctctgg acgcaccttc agtggctatg ccatgggctg gttccgccag     120
gctccgggga aggagcgtga gtttgtagcc gatattagct ggagtggtca taacacgtac     180
tatggagact ccgtgaaggg ccgattcacc atctccagag acaccgccaa gaacacggtg     240
tatctgcaaa tgaacagcct gaaacctgag gacacggccg tttattactg tgcagcggag     300
ggggcccgta cacaccttag tgatagttac tacttccccgg gcctctgggc cgaaccccccc    360 gtgggctact ggggccaggg gacccaggtc actgtctcct cagaacccaa gacaccaaaa     420
ccacaa                                                                426

<210> SEQ ID NO 5
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Glu Thr Gly Gly Gly Leu Val Gln Ala Gly Gly
1               5                   10                  15

Thr Leu Arg Leu Ser Cys Ala Ala Ser Gly Arg Thr Phe Thr Ser Tyr
            20                  25                  30

Tyr Ile Gly Trp Phe Arg Gln Glu Pro Gly Lys Glu Arg Glu Phe Val
        35                  40                  45

Ala Ser Ile Gly Trp Thr Asp Asp Asn Thr Tyr Tyr Ala Asp Ser Val
    50                  55                  60

Lys Gly Arg Phe Thr Ile Ser Arg Asp Asn Ala Glu Thr Thr Ala Tyr

```
                65                  70                  75                  80
Leu Gln Met Ser Gly Leu Lys Pro Glu Asp Thr Ala Val Tyr Tyr Cys
                    85                  90                  95

Ala Ala Asp Tyr Gly Ser Gly Ile Arg Ala Trp Tyr Asn Trp Ile Tyr
                100                 105                 110

Trp Gly Gln Gly Thr Gln Val Thr Val Ser Ser Glu Pro Lys Thr Pro
        115                 120                 125

Lys Pro Gln
    130

<210> SEQ ID NO 6
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
caggtgcagc tggtggagac cggggggagga ttggtgcagg ctggggggcac tctgagactc       60 tcctgtgcag cctctggacg taccttcacg agctattaca ttggctggtt ccgccaggaa       120
ccagggaagg agcgtgagtt tgtagcaagt atcggctgga ccgatgataa acacatactat      180 gcagactccg tgaagggccg attcaccatc tccagagaca acgccgagac acggcatat        240 ctgcaaatgt cgggcctgaa acctgaggac acggccgttt attactgtgc agccgactac       300
gggtcaggga tacgggcctg gtataattgg atttactggg gccagggggac ccaggtcacc      360 gtctcctcag aacccaagac accaaaacca caa                                    393

<210> SEQ ID NO 7
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Leu Gln Leu Ala Glu Thr Gly Gly Gly Leu Val Gln Pro Gly Gly
1               5                   10                  15

Ser Leu Arg Leu Ser Cys Ala Ala Ser Gly Ala Thr Leu Asp Thr Tyr
            20                  25                  30

Ile Ile Thr Trp Phe Arg Gln Ala Pro Gly Lys Glu Arg Glu Ala Val
        35                  40                  45

Ser Cys Ile Asn Arg Ser Gly Ser Thr Thr Tyr Ser Asp Ser Val Lys
    50                  55                  60

Gly Arg Phe Thr Ile Ser Arg Asp Asn Ala Gln Lys Thr Val Tyr Leu
65                  70                  75                  80

Gln Met Asn Ser Leu Asn Pro Glu Asp Thr Ala Ile Tyr Tyr Cys Ala
                85                  90                  95

Ala Asp Ala Ser Tyr Arg Thr Cys Gly Gly Ser Trp Trp Asn Trp Ala
                100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 8
```

<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cagttgcagc tcgcggagac gggaggaggc ttggtgcagc ctgggggctc tctgagactc    60
tcctgtgcag cctctggcgc cactttggat acttatatca taacctggtt ccgccaggcc   120
ccagggaagg agcgtgaggc cgtctcatgt attaatcgta gtggtagcac gacctattca   180
gactccgtga agggccgatt caccatctcc agagacaacg cccagaaaac ggtgtatctg   240
cagatgaaca gcctgaaccc tgaggacaca gccatttatt actgcgcagc ggatgcttcg   300
taccgtactt gcggcgggag ttggtggaat tgggcgtact ggggccaggg acccaggtc    360 accgtctcct cagaacccaa gacaccaaaa ccacaa                              396

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Ala Glu Ser Gly Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Ile Glu Trp Val
        35                  40                  45

Ser Asp Ile Asn Gly Gly Gly Asp Arg Thr Asp Tyr Ala Asp Ser Val
    50                  55                  60

Lys Gly Arg Phe Thr Ile Ser Arg Asp Asn Ala Arg Asn Thr Leu Tyr
65                  70                  75                  80

Leu Gln Met Asn Ser Leu Gln Pro Glu Asp Thr Ala Val Tyr Tyr Cys
                85                  90                  95

Ala Lys Asp Leu Ser Tyr Val Ser Gly Thr Tyr Phe Ala Asn Asp Trp
            100                 105                 110

Gly Gln Gly Thr Gln Val Thr Val Ser Ser Glu Pro Lys Thr Pro Lys
        115                 120                 125

Pro Gln
    130

<210> SEQ ID NO 10
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
caggtgcagc tcgcggagtc tggaggaggc tcggtgcaac ctgggggctc tctgagactc    60
tcctgtgcag cctctggatt caccttcagt agttatacta tgagctgggt ccgccaggct   120
ccaggaaagg ggatcgagtg gtctcagat attaatgggg gtggtgatag aacagactat    180
gcagactccg tgaagggccg attcaccatc tccagagaca cgccaggaa cacgctgtat    240

```
ctgcaaatga acagcctgca acctgaggac acggccgtgt attactgtgc aaaagatctg    300
agctacgtta gtggtactta tttcgcgaac gactggggcc aggggaccca ggtcaccgtc    360
tcctccgaac ccaagacacc aaaaccacaa                                     390
```

<210> SEQ ID NO 11
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Gln Leu Gln Leu Ala Glu Ser Gly Gly Gly Leu Val Gln Pro Gly Gly
1               5                   10                  15

Ser Leu Arg Leu Ser Cys Thr Ala Ser Gly Ile Ile Phe Asp Tyr Tyr
            20                  25                  30

Ser Val Asp Trp Tyr Arg Gln Ala Pro Gly Lys Glu Arg Glu Leu Val
        35                  40                  45

Ala Thr Ile Thr Gly Asp Gly Ser Pro Asn Tyr Ala Asp Ser Val Lys
    50                  55                  60

Gly Arg Phe Thr Ile Ser Arg Asp Asn Ala Lys Lys Thr Val Tyr Leu
65                  70                  75                  80

Gln Met Asn Gly Leu Lys Pro Glu Glu Thr Ala Val Tyr Tyr Cys His
                85                  90                  95

Ala Lys Arg Thr Ile Gly Thr Lys Ser Glu Tyr Trp Gly Gln Gly Thr
            100                 105                 110

Gln Val Thr Val Ser Ser Glu Pro Lys Thr Pro Lys Pro Gln
        115                 120                 125
```

<210> SEQ ID NO 12
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
cagttgcagc tggcggagtc gggggggaggc ttggtgcagc ctggggggtc tctgagactc    60
tcctgtacag cctctggaat catcttcgat tactattccg tggactggta ccgccaggct    120
ccagggaagg agcgcgaatt ggtcgcaact attacgggtg atggtagccc gaactatgcg    180
gactctgtca agggccgatt caccatctcc agagacaacg ccaagaagac ggtgtatctg    240
caaatgaacg gcctgaaacc tgaggaaacg gccgtctatt actgtcatgc aaaaggact    300 atagggacca atctgagta ctggggccag gggacccagg tcactgtctc ctcagaaccc    360
aagacaccaa aaccacaa                                                  378
```

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Val Gln Leu Ala Glu Thr Gly Gly Gly Leu Val Gln Ala Gly Gly
```

```
1               5                    10                   15
Ser Leu Arg Leu Ser Cys Leu Ala Ser Arg Met Ser Phe Ser Arg Arg
                20                  25                  30

Pro Met Ala Trp Tyr Arg Gln Ala Pro Gly Lys Gln Arg Glu Arg Val
                35                  40                  45

Ala Thr Ile Ser Ser Phe Gly Asp Thr Thr Asn Tyr Thr Asp Ser Val
        50                  55                  60

Glu Gly Arg Phe Thr Ile Ser Arg Asp Asn Ala Lys Asn Thr Met Tyr
65                  70                  75                  80

Leu Gln Met Asn Ser Leu Lys Pro Asp Asp Thr Ala Val Tyr Tyr Cys
                85                  90                  95

Asn Thr Leu Leu Ala Thr Tyr Ala Trp Gly Gln Gly Thr Gln Val Thr
                100                 105                 110

Val Ser Ser Glu Pro Lys Thr Pro Lys Pro Gln
            115                 120
```

<210> SEQ ID NO 14
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
caggtgcagc tcgcggagac cggggggaggc ttggtgcagg ctgggggttc tctgagactc      60
tcctgtttag cctctagaat gagctttagt aggcgcccca tggcctggta ccgccaggct     120
ccaggcaagc agcgcgaaag ggtcgcaact attagtagtt tcggtgatac cacaaactat     180
acagactccg tggagggccg attcaccatc tccagggaca tgccaagaa cacgatgtat      240
ctgcaaatga acagcctgaa acctgacgac acggccgtgt attactgtaa cacattactc     300
gctacgtacg cctggggcca ggggacccag gtcaccgtct cctcagaacc caagacacca     360
aaaccacaa                                                             369
```

<210> SEQ ID NO 15
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Val Gln Leu Ala Glu Ser Gly Gly Gly Leu Val Gln Ala Gly Gly
1               5                  10                  15

Ser Leu Arg Leu Ser Cys Ala Ala Ser Gly Arg Thr Phe Ser Ser Tyr
                20                  25                  30

Val Met Gly Trp Phe Arg Gln Ala Pro Gly Lys Glu Arg Glu Phe Val
                35                  40                  45

Ala Ala Ile Ser Arg Asn Gly Gly Lys Thr Tyr Tyr Ala Asp Ser Val
        50                  55                  60

Lys Gly Arg Phe Thr Ile Ser Arg Asp Gly Thr Glu Asn Thr Val Tyr
65                  70                  75                  80

Leu Gln Met Asn Ser Leu Lys Pro Glu Asp Thr Ala Val Tyr Tyr Cys
                85                  90                  95

Ala Ala Ala Val Ala Ala Ser Ala Glu Phe Val Thr Ala Arg Ser Asn
                100                 105                 110
```

```
Phe Tyr Glu Tyr Trp Gly Gln Gly Thr Gln Val Thr Val Ser Ser Glu
            115                 120                 125

Pro Lys Thr Pro Lys Pro Gln
        130                 135

<210> SEQ ID NO 16
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
caggtgcagc tggcggagtc ggggggagga ttggtgcagg ctgggggctc tctgagactc      60
tcctgtgcag cctctggacg caccttcagt agctatgtca tgggctggtt ccgccaggct     120
ccagggaagg agcgtgagtt tgtggccgct attagccgaa atggtggtaa gacctactat     180
gcagactccg tgaagggccg attcaccatc tcaagagacg caccgagaa cacggtgtat     240 ctgcaaatga acagcctgaa acctgaggac acggccgttt attactgcgc agcagccgta     300
gccgcttctg ccgagttttgt tacggctcgc tcgaattttt atgaatattg gggtcagggg     360
acccaggtca ctgtctcctc agaacccaag acaccaaaac cacaa                     405

<210> SEQ ID NO 17
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Thr Gly Gly Gly Leu Val Gln Ala Gly Gly
1               5                   10                  15

Ser Leu Arg Leu Ser Cys Glu Ala Ser Gly Ser Val Val Thr Ile Lys
            20                  25                  30

Glu Met Gly Trp Tyr Arg Gln Ala Pro Gly Lys Glu Arg Glu Gln Glu
        35                  40                  45

Arg Asp Leu Val Ala Ala Ile Gly Ile Gly Gly Val Thr Tyr Tyr Ala
    50                  55                  60

Thr Ser Val Lys Gly Arg Phe Thr Ile Ser Arg Asp Ser Ala Lys Thr
65                  70                  75                  80

Thr Leu Arg Leu Gln Met Ser Ser Leu Arg Pro Glu Asp Thr Ala Met
                85                  90                  95

Tyr Tyr Cys Ala Val Ile Thr Asp Arg Asn Thr Gly Tyr Pro Asp
            100                 105                 110

Tyr Trp Gly Gln Gly Thr Gln Val Thr Val Thr Ala Glu Pro Lys Thr
        115                 120                 125

Pro Lys Pro Gln
        130

<210> SEQ ID NO 18
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide
```

-continued

<400> SEQUENCE: 18

```
caggtgcagc tggtggagac gggtggaggc ttggtgcagg ctggggggtc tctgagactc      60
tcctgtgaag cctctggaag cgtcgtcacc atcaaagaga tgggctggta ccgacaggct     120
ccaggaaagg agcgcgaaca ggagcgcgac ttggtcgcag caattggcat tggtggtgtc     180
acatactacg caacctctgt gaagggccga ttcaccatct ccagagacag tgccaagact     240
acgctgcgtc tgcaaatgag cagcctgaga cctgaggaca cggccatgta ttattgtgcg     300
gtcataactg acaggaacac cggtggttac ccggactact ggggccaggg acccaggtc      360 actgttaccg cagaacccaa gacaccaaaa ccacaa                              396
```

<210> SEQ ID NO 19
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Gln Val Gln Leu Val Glu Ser Gly Gly Gly Leu Val Gln Ala Gly Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
        35                  40                  45

Gly Val Ser Cys Ile Ser Ser Thr Asp Gly Ala Thr Tyr Tyr Ala Asp
    50                  55                  60

Ser Val Lys Gly Arg Phe Thr Ile Ser Arg Asn Asn Ala Lys Asn Thr
65                  70                  75                  80

Val Tyr Leu Gln Met Asn Asn Leu Lys Pro Glu Asp Thr Ala Ile Tyr
                85                  90                  95

Tyr Cys Ala Ala Ala Pro Leu Ala Gly Arg Tyr Cys Pro Ala Ser His
            100                 105                 110

Glu Tyr Gly Tyr Trp Gly Gln Gly Thr Gln Val Thr Val Ser Ser Glu
        115                 120                 125

Pro Lys Thr Pro Lys Pro Gln
    130                 135
```

<210> SEQ ID NO 20
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
caggtgcagc tggtggagtc cggtggaggc ttggtgcagg ctggggggtc tctgagactc      60
tcctgtgcag cctctatact cacttatgat ttggattatt attacatagg ctgggtccgc     120
caggccccag gaaggagcg tgaggggtc tcatgtatta gtagtactga tggtgccaca      180
tactatgcag actccgtgaa gggccgattc accatctcca gaacaacgc caagaacacg      240 gtgtatctgc aaatgaacaa cctaaaacct gaggacacag ccatttatta ttgtgcagca     300
gcccccctgg ctgggcgcta ctgtcccgcc tcgcatgagt atggctactg gggtcagggg     360
acccaggtca ccgtctcgtc agaacccaag acaccaaaac cacaa                     405
```

<210> SEQ ID NO 21
<211> LENGTH: 133
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 21

Gln Val Gln Leu Val Glu Ser Gly Gly Gly Leu Val Gln Pro Gly Glu
1               5                   10                  15

Ser Leu Arg Leu Ser Cys Gly Ala Ser Gly Met Ser Leu Asp Tyr Tyr
            20                  25                  30

Ala Ile Ala Trp Tyr Arg Gln Ala Pro Gly Lys Glu Arg Glu Gly Val
        35                  40                  45

Ser Cys Ile Ser Val Ser Gly Ser Ala Gln Tyr Leu Asp Ser Val
    50                  55                  60

Arg Gly Arg Phe Ile Ile Ser Lys Asp Asn Thr Lys Ser Thr Ala Tyr
65                  70                  75                  80

Leu Gln Met Asn Ser Leu Lys Pro Glu Asp Thr Ala Val Tyr Tyr Cys
                85                  90                  95

Ala Ala Leu Ala Asp Cys Ala Gly Tyr Ala Ser Leu Thr Phe Asp Phe
            100                 105                 110

Asp Ser Trp Gly Gln Gly Thr Gln Val Ala Val Ser Ser Ala His His
        115                 120                 125

Ser Glu Asp Pro Ser
    130

<210> SEQ ID NO 22
<211> LENGTH: 399
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 22
caggtgcagc tcgtggagtc gggtggaggc ttggtgcagc ctggggagtc tctgagactc      60
tcctgtggag cctctggaat gagtttggat tactatgcca tagcctggta ccgccaggcc     120
ccagggaagg agcgtgaggg ggtctcatgt attagtgtta gtggcagtag cgcacaatat     180
ttagactccg tgaggggtcg cttcatcatc tccaaagaca acaccaagag cacggcgtat     240
ctgcaaatga acagcctgaa gcctgaagac acagccgttt attactgcgc agccctggcc     300
gactgtgcag gctatgccag tcttaccttt gactttgatt cttggggcca ggggacccag     360
gtcgccgtct cctcggcgca ccacagcgaa gaccccctcg                           399

<210> SEQ ID NO 23
<211> LENGTH: 133
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 23

Gln Val Gln Leu Val Glu Ser Gly Gly Gly Leu Val Gln Ala Gly Gly
1               5                   10                  15

Ser Leu Arg Leu Ser Cys Ala Pro Ser Arg Leu Thr Leu Asp Phe Phe
            20                  25                  30

Ala Ile Ala Trp Phe Arg Gln Ala Pro Gly Lys Glu Arg Glu Gly Val
            35                  40                  45

Ser Cys Ile Ser Ser His Asp Gly Ser Thr Tyr Tyr Thr Asp Ser Val
        50                  55                  60

Lys Gly Arg Phe Thr Ile Ser Lys Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Leu Asp His Asn Val Gly Thr Cys Gln Leu Thr Gln Ala Glu Tyr
            100                 105                 110

Asp Tyr Trp Gly Gln Gly Thr Gln Val Thr Val Ser Ser Ala His His
        115                 120                 125

Ser Glu Asp Pro Ser
    130

<210> SEQ ID NO 24
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
caggtgcagc tggtggagtc cggtggaggc ttggtgcagg ctgggggtc tctgagactc      60 tcctgtgcac cctcgcgatt aactttggat ttctttgcca tagcctggtt ccgccaggcc    120
ccagggaagg agcgtgaggg ggtctcatgt attagtagtc atgatggtag cacatactac    180
acagactccg tgaagggccg attcaccatc tccaaagaca cgccaagaa cacggtgtat     240 ctgcaaatga acagcctgaa gcctgaggac acagccgttt attactgtgc cctagaccat    300
aacgtgggta cctgccaact cacccaagct gagtatgact actggggcca ggggacccag    360
gtcaccgtct cctcggcgca ccacagcgaa gaccctcg                             399

<210> SEQ ID NO 25
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Val Glu Ser Gly Gly Gly Leu Val Gln Ser Gly Gly
  1               5                  10                  15

Ser Leu Arg Leu Ser Cys Ala Ser Gly Ser Ile Asp Ser Leu Tyr
            20                  25                  30

His Met Gly Trp Tyr Arg Gln Ala Pro Gly Lys Glu Arg Glu Leu Val
            35                  40                  45

Ala Arg Val Gln Asp Gly Gly Ser Thr Ala Tyr Lys Asp Ser Val Lys
        50                  55                  60

Gly Arg Phe Thr Ile Ser Arg Asp Phe Ser Arg Ser Thr Met Tyr Leu
 65                  70                  75                  80

Gln Met Asn Ser Leu Lys Pro Glu Asp Thr Ala Ile Tyr Tyr Cys Ala
                85                  90                  95

Ala Lys Ser Thr Ile Ser Thr Pro Leu Ser Trp Gly Gln Gly Thr Gln
            100                 105                 110

Val Thr Val Ser Ser Glu Pro Lys Thr Pro Lys Pro Gln
            115                 120                 125

<210> SEQ ID NO 26
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caggtgcagc tggtggagtc cggggggaggc ttggtgcagt ctgggggggtc tctgagactc      60 tcctgtgcag cctctggaag tatcgatagt ctctatcata tgggctggta ccgccaggct     120
ccagggaagg agcgcgagtt ggtcgcacga gttcaagatg ggggtagcac agcgtacaaa     180
gactctgtga agggcgatt caccatctcc agagactttt ccaggagcac gatgtatctg     240
caaatgaaca gcctgaaacc tgaggacacg gccatctatt actgtgcggc aagagtaca      300 attagcaccc ccttgtcctg gggccagggg acccaggtca ccgtctcctc ggaacccaag     360
acaccaaaac cacaa                                                      375

<210> SEQ ID NO 27
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Gly His Asn
            20                  25                  30

Gln Val Ala Trp Phe Arg Gln Ala Pro Gly Lys Glu Arg Glu Gly Val
        35                  40                  45

Ala Cys Ile Ser Ala Thr Gly Ala Ser Thr His Tyr Ala Asp Pro Val
    50                  55                  60

Lys Gly Arg Phe Thr Val Ser Arg Asp Asn Thr Lys Asn Val Val Tyr
65                  70                  75                  80

Leu Gln Val Asn Ser Leu Lys Pro Glu Asp Thr Ala Asn Tyr Val Cys
                85                  90                  95

Ala Ser Arg Phe Ser Leu Met Ser Ile Asp Ala Ser Met Cys Leu Ser
            100                 105                 110

Ala Pro Gln Tyr Asp Arg Trp Gly Gln Gly Thr Gln Val Arg Ile Ser
        115                 120                 125

Ser Glu Pro Lys Thr Pro Lys Pro Gln
    130                 135

<210> SEQ ID NO 28
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
caggtgcagc tggtggagtc cggtggaggc ttggtgcagg ctgggggggtc tctgagactc      60

| | |
|---|---|
| tcctgtgcag cctctggatt cactttggga cataatcaag tagcctggtt ccgccaggcc | 120 |
| ccaggcaagg agcgtgaggg ggtcgcgtgt attagcgcca ccgtgctag cacacactat | 180 |
| gcagaccccg tgaagggccg atttaccgtc tccagagaca acaccaagaa cgtggtgtat | 240 |
| ctgcaagtga acagcctgaa acctgaggac acggccaatt atgtctgtgc aagcagattc | 300 |
| tcccttatgt cgatcgatgc gagcatgtgc ctttcggcgc ctcagtatga ccgctggggc | 360 |
| caggggaccc aggtcagaat ctcctcagaa cccaagacac caaaaccaca a | 411 |

<210> SEQ ID NO 29
<211> LENGTH: 136
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Gln Val Gln Leu Val Glu Thr Gly Gly Leu Val Gln Pro Gly Gly Ser
1               5                   10                  15

Leu Arg Leu Ser Cys Thr Ala Ser Gly Phe Thr Leu Gly His His Arg
            20                  25                  30

Val Gly Trp Phe Arg Gln Ala Pro Gly Lys Glu Arg Glu Gly Val Ala
        35                  40                  45

Cys Ile Ser Ala Thr Gly Leu Ser Ser His Tyr Ser Asp Phe Val Ile
    50                  55                  60

Gly Arg Phe Thr Val Ser Arg Asp Asn Asp Asn Val Val Tyr Leu
65                  70                  75                  80

Gln Val Asn Gly Leu Lys Pro Glu Asp Thr Ala Val Tyr Tyr Cys Ala
                85                  90                  95

Ser Arg Phe Ser Leu Asn Ser Val Asp Ala Asn Met Cys Leu Ser Glu
            100                 105                 110

Pro Gln Tyr Asp Asn Trp Gly Gln Gly Thr Pro Val Arg Ile Ser Ser
        115                 120                 125

Glu Pro Lys Thr Pro Lys Pro Gln
    130                 135

<210> SEQ ID NO 30
<211> LENGTH: 408
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

| | |
|---|---|
| caggtgcagc tggtggagac gggtggcttg gtgcagcctg ggggtctct gagactctcc | 60 |
| tgtacagcct ctggattcac tttgggacac catcgcgttg gctggttccg ccaggcccca | 120 |
| ggaaaggagc gtgaggggt cgcgtgtatt agcgccactg gtcttagttc acactattca | 180 |
| gacttcgtga tcggccgatt taccgtctcc agagacaacg acaacaacgt ggtgtatcta | 240 |
| caagtgaacg gcctgaaacc tgaggacaca gccgtttatt actgtgcaag cagattctcc | 300 |
| cttaattcgg tcgatgcgaa tatgtgcctt tcggagcctc agtatgacaa ctggggccag | 360 |
| gggacccccgg tcagaatctc ctcagaaccc aagacaccaa aaccacaa | 408 |

<210> SEQ ID NO 31
<211> LENGTH: 134
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 31

```
Gln Val Gln Leu Val Glu Ser Gly Gly Gly Leu Val Gln Ala Gly Gly
1               5                   10                  15

Ser Leu Arg Leu Ser Cys Ala Ala Ser Glu Phe Arg Ala Glu His Phe
            20                  25                  30

Ala Val Gly Trp Phe Arg Gln Ala Pro Gly Lys Glu Arg Glu Gly Val
        35                  40                  45

Ser Cys Val Asp Ala Ser Gly Asp Ser Thr Ala Tyr Ala Asp Ser Val
    50                  55                  60

Lys Gly Arg Phe Thr Ile Ser Arg Asp Asn Lys Asn Val Val Tyr
65                  70                  75                  80

Leu Gln Met Asp Ser Leu Glu Pro Glu Asp Thr Gly Asp Tyr Tyr Cys
                85                  90                  95

Gly Ala Ser Tyr Phe Thr Val Cys Ala Lys Ser Met Arg Lys Ile Glu
            100                 105                 110

Tyr Arg Tyr Trp Gly Gln Gly Thr Gln Val Thr Val Ser Ser Glu Pro
        115                 120                 125

Lys Thr Pro Lys Pro Gln
    130
```

<210> SEQ ID NO 32
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
caggtgcagc tggtggagtc cggtggaggc ttggtgcagg ctgggggtc tctgagactc     60
tcctgtgcag cctctgaatt ccgtgcggag cattttgccg tgggctggtt ccgccaggcc   120
ccagggaagg agcgtgaggg ggtctcatgt gtagacgcga gtggtgatag tacagcatat   180
gcggactctg tgaagggccg attcaccatc tccagagaca acaacaagaa cgtagtgtat   240
ctgcaaatgg acagcctgga acctgaagac acaggagatt attattgtgg agcctcgtac   300
tttactgtct gcgccaagag catgcggaaa attgaatata ggtactgggg ccaggggacc   360
caggtcaccg tctcctcaga acccaagaca ccaaaaccac aa                      402
```

<210> SEQ ID NO 33
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Gln Val Gln Leu Ala Glu Ser Gly Gly Gly Leu Val Gln Pro Gly Gly
1               5                   10                  15

Ser Leu Arg Leu Ser Cys Ala Ala Ser Gly Arg Ala Leu Asn Tyr Tyr
            20                  25                  30

Val Ile Gly Trp Phe Arg Gln Ala Pro Gly Lys Glu Arg Glu Gly Val
        35                  40                  45
```

Ser Cys Ile Ala Ser Ser Glu Ala Tyr Thr Asp Tyr Ala Asp Ser Val
    50                  55                  60

Gln Gly Arg Phe Thr Ile Ser Arg Asp Lys Ala Leu Asn Thr Val Tyr
65                  70                  75                  80

Leu Asp Met Lys Arg Leu Lys Pro Asp Asp Thr Ala Val Tyr Tyr Cys
                85                  90                  95

Ala Ala Arg Leu Arg Asp Pro Asn Trp Cys Gly Arg Asn Ala Asp Glu
            100                 105                 110

Tyr Asp Ser Trp Gly Gln Gly Thr Gln Val Thr Val Ser Ser Glu Pro
                115                 120                 125

Lys Thr Pro Lys Pro Gln
    130

<210> SEQ ID NO 34
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
caggtgcagc tcgcggagtc aggcggaggc ttggtgcagc tggggggtc tctgagactc       60 tcctgtgcag cctctggacg cgctttgaat tattatgtca taggctggtt ccgccaggcc     120
ccagggaagg agcgtgaggg ggtctcatgt attgcgagta gcgaagccta cacagactat     180
gcagactccg tgcaaggccg attcaccatc tcgagagaca aggctctgaa tacggtgtat     240
ttggatatga agcgcctgaa acctgacgac acagccgttt attattgtgc agcccggttg     300
cgtgatccta attggtgcgg gcggaatgcg gatgagtatg actcctgggg ccaggggacc     360
caggtcaccg tctcctcaga acccaagaca ccaaaaccac aa                        402

<210> SEQ ID NO 35
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Leu Val Gln Ala Gly Gly
1               5                   10                  15

Ser Leu Arg Leu Ser Cys Ala Ala Ser Gly Phe Pro Phe Gly Ser Tyr
            20                  25                  30

Tyr Met Ser Trp Val Arg Gln Ala Pro Gly Lys Gly Pro Glu Trp Val
        35                  40                  45

Ser Asp Ile Ser Asn Gly Gly Ile Ile Thr Arg Tyr Ser Asp Ser Val
    50                  55                  60

Lys Gly Arg Phe Thr Ile Ser Arg Asp Asn Ala Lys Asn Ile Leu Tyr
65                  70                  75                  80

Leu Gln Met Asn Ser Leu Lys Pro Glu Asp Thr Ala Leu Tyr Phe Cys
                85                  90                  95

Ala Thr Gly Thr Gly Arg Asp Trp Ser Arg Glu Tyr Arg Gly Gln Gly
            100                 105                 110

Thr Gln Val Thr Val Ser Ser Glu Pro Lys Thr Pro Lys Pro Gln
        115                 120                 125

<210> SEQ ID NO 36
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
caggtgcagc tggtggagtc cggtggaggc ttggtgcagg ctggggggtc tctgagactc    60
tcctgtgcag cctctggatt ccccttcggt agttactaca tgagctgggt ccgccaggct   120
ccaggaaagg ggcccgagtg ggtctcagat attagcaatg gtggtattat tacaaggtat   180
tcagactccg tgaagggccg attcaccatc tcccgagaca acgccaagaa catattgtat   240
ctgcaaatga acagcctgaa acctgaagac acggccctgt atttctgtgc gacagggacc   300
ggtagagact ggagcaggga gtaccggggc caggggaccc aggtcaccgt ctcctcagaa   360
cccaagacac caaaaccaca a                                              381
```

<210> SEQ ID NO 37
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

```
Gln Val Gln Leu Ala Glu Ser Gly Gly Gly Leu Val Gln Pro Gly Gly
1               5                   10                  15

Ser Leu Arg Leu Ser Cys Glu Ala Ser Gly Phe His Leu Glu His Phe
            20                  25                  30

Ala Val Gly Trp Phe Arg Gln Ala Pro Gly Lys Glu Arg Glu Gly Val
        35                  40                  45

Ser Cys Ile Ser Ala Ser Gly Asp Ser Thr Thr Tyr Ala Asp Ser Val
    50                  55                  60

Lys Gly Arg Ser Thr Ile Ser Lys Asp Asn Ala Lys Asn Ala Val Tyr
65                  70                  75                  80

Leu Gln Met Asp Ser Leu Arg Pro Glu Asp Thr Gly Asp Tyr Tyr Cys
                85                  90                  95

Ala Ala Ser His Phe Ser Val Cys Gly Lys Asn Ile Arg Lys Ile Glu
            100                 105                 110

Tyr Arg Tyr Trp Gly Gln Gly Thr Pro Val Thr Val Ser Ser Glu Pro
        115                 120                 125

Lys Thr Pro Lys Pro Gln
    130
```

<210> SEQ ID NO 38
<211> LENGTH: 402
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 38

```
caggtgcagc tcgcggagtc tggtggaggc ttggtgcagc ctggggggtc tctgagactc    60
tcctgtgaag cctcaggatt ccatttggag cattttgccg taggctggtt ccgccaggcc   120
ccagggaagg agcgtgaggg ggtctcatgt ataagcgcga gtggtgatag tacaacgtat   180
```

```
gcagactccg tgaagggccg atccaccatc tccaaagaca acgccaagaa cgcggtgtat     240
ctgcaaatgg acagcctgag acccgaggac acaggcgatt attactgtgc agcctcgcac     300
ttcagtgtct gcggcaagaa cattcggaaa attgagtata ggtactgggg ccaggggacc     360
ccggtcaccg tctcctcaga acccaagaca ccaaaaccac aa                        402
```

<210> SEQ ID NO 39
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Thr Gly Gly Gly Leu Val Gln Pro Gly Gly
1               5                   10                  15

Ser Leu Arg Leu Ser Cys Val Val Ser Gly Leu Thr Phe Asn Ser Asn
            20                  25                  30

Tyr Met Ser Trp Val Arg Gln Ala Pro Gly Lys Gly Pro Glu Leu Val
        35                  40                  45

Ser Tyr Ile Asn Ser Glu Asp Gly Ser Thr Phe Tyr Ala Asp Ser Val
    50                  55                  60

Lys Gly Arg Phe Thr Ile Ser Arg Asp Asn Asn Glu Asn Thr Leu Tyr
65                  70                  75                  80

Leu Gln Met Ser Ser Leu Lys Pro Glu Asp Thr Ala Arg Tyr Tyr Cys
                85                  90                  95

Ala Leu Gly Ile Ala Gly Ala Thr Arg Gly Gln Gly Thr Gln Val Thr
            100                 105                 110

Val Ser Ser Glu Pro Lys Thr Pro Lys Pro Gln
        115                 120

<210> SEQ ID NO 40
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
caggtgcagc tcgtggagac cggggggaggc ttggtgcagc cggggggggtc tctgagactc      60 tcctgtgtag tgtctggatt aaccttcaat agcaactaca tgagttgggt ccgccaggct     120
ccagggaagg ggcccgagtt ggtctcatat attaattctg aagatggtag taccttttat     180
gcagactccg tgaagggccg attcaccatc tcgcgagaca caacgagaa tacactgtat      240 ctgcaaatga gcagcctgaa gcctgaggac acggcccgct attactgtgc actggggatc     300
gctggtgcaa ctcggggcca ggggacccag gtcaccgtct cctcagaacc caagacacca    360
aaaccacaa                                                             369
```

<210> SEQ ID NO 41
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ala Cys Ile Ser Ala Ser Gly Ser Gly Thr Asp Tyr Val Asp Ser Val
    50                  55                  60

Lys Gly Arg Phe Thr Val Ser Arg Asp Gln Ala Lys Ser Met Val Phe
65                  70                  75                  80

Leu Gln Met Asn Asn Met Lys Pro Glu Asp Ala Ala Val Tyr Tyr Cys
                85                  90                  95

Ala Ala Asp Tyr Arg Pro Arg Pro Leu Pro Ile Gln Ala Pro Cys Thr
            100                 105                 110

Met Thr Gly Gly Asn Tyr Trp Gly Gln Gly Thr Gln Val Thr Val Ser
            115                 120                 125

Ser Glu Pro Lys Thr Pro Lys Pro Gln
            130                 135

<210> SEQ ID NO 42
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
caggtgcagc tcgtggagtc aggggggaggc ttggtgcagc ctggggggtc tctgagactc      60
tcctgtgcag cctctggatt cactttagat agttatgcaa taggctggtt ccgccaggcc     120
ccagggaagg agcgtgaggg ggtcgcatgt attagtgcta gtggtagtgg cacggactat     180
gtagactccg tgaagggccg attcaccgtc tccagagacc aggccaagag catggtgttt     240
ctgcaaatga acaacatgaa acctgaggac gcagccgttt attactgtgc agcagattat     300
cggccgaggc ccctgccgat tcaggcgccg tgtacaatga caggtggcaa ctactggggc     360
caggggaccc aggtcaccgt ctcctcagaa cccaagacac caaaaccaca a              411

<210> SEQ ID NO 43
<211> LENGTH: 138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Glu Ser Gly Gly Gly Leu Val Gln Pro Gly Gly
1               5                   10                  15

Ser Leu Thr Leu Ser Cys Val Ala Ser Gly Ser Asn Leu Asp Tyr Phe
            20                  25                  30

Ala Ile Gly Trp Phe Arg Gln Ala Pro Gly Lys Glu Arg Glu Gly Val
        35                  40                  45

Ser Cys Ile Ser Thr Ser Ser Asp Met Ser Lys Tyr Ala Asp Ser Val
    50                  55                  60

Lys Gly Arg Phe Thr Ile Ser Arg Asp Asn Thr Arg Asn Thr Val Tyr
65                  70                  75                  80

Leu Gln Met Asn Ser Leu Glu Pro Glu Asp Thr Ala Val Tyr Tyr Cys
```

```
                    85                  90                  95
Ala Ala Lys Arg Arg Tyr Gly Leu Asp Arg Asp Met Cys Leu Met
                100                 105                 110

Asp Ser Val Gly Met Asp Val Trp Gly Lys Gly Thr Leu Val Thr Val
            115                 120                 125

Ser Ser Ala His His Ser Glu Asp Pro Ser
    130                 135

<210> SEQ ID NO 44
<211> LENGTH: 414
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caggtgcagc tggtggagtc ggggggaggc ttggtgcagc ctgggggtc tctgacactc       60 tcctgtgtag cctctggatc caatttggat tattttgcga taggctggtt ccgccaggcc     120
ccagggaagg agcgtgaggg ggtctcatgt attagtacga gtagtgacat gtcaaagtat     180
gcagactccg tgaagggccg cttcaccatc tccagagaca acaccaggaa cacggtgtat     240
ctgcaaatga acagcctgga acccgaagat acggccgttt attattgtgc agcaaagcgc     300
cgccgatatg gtctcgatcg tgatatgtgt cttatggatt cggtcggcat ggacgtgtgg     360
ggcaaaggga ccctggtcac cgtctcctcg gcgcaccaca gcgaagaccc ctcg            414

<210> SEQ ID NO 45
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Glu Ser Gly Gly Gly Leu Val Gln Pro Gly Gly
1               5                   10                  15

Ser Leu Arg Leu Ser Cys Ala Ala Pro Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ser Cys Ile Arg Ser Arg Gly Asp Arg Thr Asn Tyr Ala Asp Ser Val
    50                  55                  60

Lys Gly Arg Phe Thr Val Ser Arg Asp Asn Ala Lys Asn Thr Ala Tyr
65                  70                  75                  80

Leu Gln Met Asn Asn Leu Lys Pro Glu Asp Thr Gly Val Tyr Phe Cys
                85                  90                  95

Ala Ala Ala Pro Arg Thr Thr Val Gln Asp Leu Cys Val Thr Pro Leu
                100                 105                 110

Leu Gly Gly Ala Asp Trp Val Ser Trp Gly Gln Gly Thr Gln Val Thr
            115                 120                 125

Val Ser Ser Glu Pro Lys Thr Pro Lys Pro Gln
    130                 135

<210> SEQ ID NO 46
<211> LENGTH: 417
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 46
caggtgcagc tcgtggagtc aggaggaggc ttggtgcagc ctgggggtc tctgagactc      60 tcctgtgcag ctcctggatt cactttggat tattatgcca taggctggtt ccgccaggcc    120
ccagggaagg agcgtgaggg ggtctcatgt attcgtagtc gtggtgatcg gacaaattat    180
gcagactccg tgaagggccg attcaccgtc tccagagaca acgccaagaa cacggcgtat    240
ctgcaaatga acaacctgaa acctgaggac acaggcgttt atttctgtgc agctgctccg    300
aggactactg ttcaggattt gtgtgtaacc cctcttttgg ggggtgctga ctgggtttcc    360
tggggccagg ggacccaggt caccgtctcc tcggaaccca agacaccaaa accacaa      417

<210> SEQ ID NO 47
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Pro Leu Gly Asp Tyr
            20                  25                  30

Thr Val Gly Trp Phe Arg Gln Ala Pro Gly Lys Glu Arg Glu Gly Val
        35                  40                  45

Ser Cys Ile Ser Lys Gly Ser Arg Gly Leu Arg Tyr Gly Asp Ser Val
    50                  55                  60

Lys Gly Arg Phe Thr Val Ala Arg Asp Asn Ala Lys Ser Thr Val Thr
65                  70                  75                  80

Leu Gln Met Asp Ser Leu Lys Pro Glu Asp Thr Ala Val Tyr Ser Cys
                85                  90                  95

Ala Ala Gly Pro Ala Met Phe Asn Gln Cys His Met Val Asp Asn Tyr
            100                 105                 110

Phe Thr Tyr Trp Gly Gln Gly Thr Gln Val Thr Val Ser Ser Ala His
        115                 120                 125

His Ser Glu Asp Pro Ser
    130

<210> SEQ ID NO 48
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
cagttgcagc tggtggagtc tggcggaggc ttggtgcagc ctgggggtc tctgagactc      60 tcctgtgcag cctctggatt ccctttgggt gattataccg tgggctggtt ccgccaggcc    120
ccagggaagg agcgtgaggg ggtctcatgt attagtaaag gtagtagagg cttaagatac    180
ggagactccg tgaaaggccg attcaccgtt gccagagaca acgccaagag cacggtaact    240
ctgcaaatgg acagcctgaa accggaggac acagccgttt attcttgtgc tgcagggccg    300

```
gccatgttca atcaatgtca tatggtcgac aattacttta catactgggg tcagggacc    360 caggtcaccg tctcctcggc gcaccacagc gaagacccct cg                      402
```

<210> SEQ ID NO 49
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

```
Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Ser Trp Ser Gly Ala His Thr Tyr Tyr Ala Asp Ser Val
    50                  55                  60

Lys Gly Arg Phe Thr Ile Ser Arg Asp Asn Ala Lys Ser Thr Met Tyr
65                  70                  75                  80

Leu Gln Met Asn Ser Leu Lys Pro Glu Asp Thr Ala Val Tyr Tyr Cys
                85                  90                  95

Asn Ala Asp Leu Glu Arg Tyr Ser Asp Phe Gly Arg Glu Val Asp Asp
            100                 105                 110

Tyr Trp Gly Gln Gly Thr Gln Val Thr Val Ser Ser Glu Pro Lys Thr
        115                 120                 125

Pro Lys Pro Gln
    130
```

<210> SEQ ID NO 50
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
caggtgcagc tcgtggagac aggtggagga ttggtgcagg ctggggggtc tctgagactc    60
tcctgtgcag cctctggacg caccttcagt aactatgcca tgggctggtt ccgccaggct   120
ccagggaagg agcgtgagtt tgtcgcagct attagctgga gtggtgctca cacatactat   180
gcagactccg tgaagggccg attcaccatc tccagagaca acgccaagag cacgatgtat   240
ctgcaaatga acagcctgaa acctgaggac acggccgtct attactgtaa tgcagatctc   300
gagcggtata gtgacttcgg tagggaggtg gatgactact ggggccaggg gacccaggtc   360
accgtctcct cagaacccaa gacaccaaaa ccacaa                             396
```

<210> SEQ ID NO 51
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Gln Val Gln Leu Val Glu Ser Gly Gly Gly Leu Val Gln Pro Gly Gly
```

```
1               5                   10                  15
Ser Leu Arg Leu Ser Cys Thr Ala Ser Gly Leu Thr Leu Ala Lys Trp
            20                  25                  30

Thr Ile Asn Trp Phe Arg Gln Ala Pro Gly Lys Glu Arg Glu Gly Ile
            35                  40                  45

Ser Cys Ile Ser Ser Ser Gly Ser Thr Tyr Tyr Ala Asp Ser Val
            50                  55                  60

Lys Gly Arg Phe Thr Ile Ser Arg Asp Asn Ala Glu Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asp Ser Phe Lys Gly Cys Thr Phe Leu Ser Ser Thr Thr His
                100                 105                 110

Tyr Asn Asn Met Asp Tyr Trp Gly Lys Gly Thr Leu Val Thr Val Ser
            115                 120                 125

Ser Ala His His Ser Glu Asp Pro Ser
            130                 135
```

<210> SEQ ID NO 52
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggtgcagc tcgtggagtc gggtggaggc ttggtgcagc tgggggggtc tctgagactc      60
tcgtgtacag cctctggatt aactttggct aagtggacca tcaactggtt ccgccaggcc     120
ccagggaagg agcgcgaggg gatctcatgt attagtagca gtagtggtag cacatactat     180
gcagactccg tgaagggccg attcaccatc tccagagaca cgccgaaaaa cacggtatat     240
ctgcaaatga gcagcctgaa acctgaggac acggccgttt attactgtgc agcggattct     300
tttaagggct gtacgttcct cagtagtact acccattaca caacatggac tactggggc      360 aaagggaccc tggtcaccgt ctcctcagcg caccacagcg aagacccctc g              411

<210> SEQ ID NO 53
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Val Gln Leu Val Glu Ser Gly Gly Gly Leu Val Gln Ser Gly Gly
1               5                   10                  15

Ser Leu Arg Leu Ser Cys Ala Ala Ser Arg Arg Thr Ala Ser Asn Tyr
            20                  25                  30

Ala Val Ala Trp Phe Arg Gln Ala Pro Gly Lys Glu Arg Glu Phe Val
            35                  40                  45

Ala Ala Ile Gly Trp Ser Asp Asp Val Thr Tyr Tyr Ala Asp Ser Val
            50                  55                  60

Lys Gly Arg Phe Thr Val Ser Arg Asp Asn Ala Lys Asn Thr Val Tyr
65                  70                  75                  80

Leu Gln Met Asn Gly Leu Glu Pro Glu Asp Thr Ala Val Tyr Tyr Cys
                85                  90                  95
```

Thr Thr Asn Gly Asp Arg Tyr Ser Tyr Arg Thr Ala Ser Ser Tyr His
            100                 105                 110

Tyr Trp Gly Gln Gly Thr Gln Val Thr Val Ser Ser Ala His His Ser
        115                 120                 125

Glu Asp Pro Ser
    130

<210> SEQ ID NO 54
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
caggtgcagc tcgtggagtc gggtggggga ttggtgcagt ctgggggctc tctgagactc      60
tcctgtgcag cctctagacg caccgccagt aactatgccg tggcctggtt ccgccaggct     120
ccaggaaagg agcgtgagtt tgtagcagcg attggctgga gtgatgatgt cacgtattac     180
gcagactccg tgaagggccg attcaccgtc tccagagaca cgccaagaa cacggtgtat     240 ctgcaaatga acggcctgga acctgaggac acggccgttt attactgtac aacaaatggt     300
gatagataca gttacaggac ggcatccagc tatcactact ggggccaggg gacccaggtc     360
accgtctcct cagcgcacca cagcgaagac ccctcg                              396

<210> SEQ ID NO 55
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Ala Glu Thr Gly Gly Gly Ser Val Gln Thr Gly Gly
1               5                   10                  15

Ser Leu Arg Leu Ser Cys Ala Ala Ser Gly Leu Pro Phe Arg Asn Tyr
            20                  25                  30

Ala Met Ala Trp Phe Arg Gln Ala Pro Gly Lys Glu Arg Glu Phe Val
        35                  40                  45

Ala Ala Ile Ser Arg Glu Gly Gly Arg Thr Tyr Tyr Ala Asp Phe Val
    50                  55                  60

Lys Gly Arg Phe Thr Ile Ser Arg Asp Asn Gly Arg Asn Thr Ile Tyr
65                  70                  75                  80

Leu Glu Met Asn Ser Leu Ala Ser Glu Asp Thr Ala Ile Tyr Tyr Cys
                85                  90                  95

Ala Gly Val Glu Gly Ala Tyr Thr Tyr Arg Thr Gly Ala Ser Tyr Thr
            100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 56
<211> LENGTH: 396
<212> TYPE: DNA
<213> ORGANISM: Artificial Sequence
<220> FEATURE:

<210> SEQ ID NO 56
<211> LENGTH: 396
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
caggtgcagc tcgcggagac tgggggagga tcggtgcaga ctgggggctc tctgaggctc      60
tcctgtgcag cctctggact gcccttcaga aactatgcca tggcctggtt ccgccaggct     120
ccagggaagg agcgtgagtt tgtagcagct attagtcggg aaggcgggag acatactat     180
gcagacttcg tgaagggccg attcaccatc tccagagaca acggcaggaa cacgatatat     240
ctggagatga acagcctggc atcggaggat acggccattt attactgtgc cggtgtcgag     300
ggtgcttata cttatcgtac cggggcctcg tatacttact ggggccaggg gacccaggtc     360
accgtctcct cagaacccaa gacaccaaaa ccacaa                               396
```

<210> SEQ ID NO 57
<211> LENGTH: 131
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Gln Val Gln Leu Val Glu Thr Gly Gly Gly Leu Val Gln Ala Gly Gly
1               5                   10                  15
Ser Leu Arg Leu Ser Cys Ala Ala Ser Gly Arg Ser Tyr Ala Met Gly
            20                  25                  30
Trp Phe Arg Gln Gly Pro Gly Lys Glu Arg Glu Phe Val Ala Thr Ile
        35                  40                  45
Ser Trp Ser Ser Thr Asn Thr Trp Tyr Ala Asp Ser Val Lys Gly Arg
    50                  55                  60
Phe Thr Ile Ser Arg Asp Asn Ala Lys Asn Thr Val Tyr Leu Gln Met
65                  70                  75                  80
Asn Ser Leu Lys Pro Glu Asp Thr Ala Val Tyr Tyr Cys Ala Ala Ser
                85                  90                  95
His Arg Phe Ser Asp Tyr Pro Met Arg Ser Glu Asp Gly Met Asp Tyr
            100                 105                 110
Trp Gly Lys Gly Thr Leu Val Thr Val Ser Ser Glu Pro Lys Thr Pro
        115                 120                 125
Lys Pro Gln
    130
```

<210> SEQ ID NO 58
<211> LENGTH: 393
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 58

```
caggtgcagc tggtggagac ggggggagga ttggtgcagg ctgggggctc tctgagactc      60
tcctgtgcag cctctggacg cagttatgcc atgggctggt tccgccaggg tccagggaag     120
gagcgtgagt ttgtagccac tatcagttgg agtagtacta acacatggta tgcagattcc     180
gtgaagggcc gattcaccat ctctagagac aacgccaaga acacggtgta tctgcaaatg     240
aacagcctga aacctgagga cacggctgtt tattactgtg cagcgagcca tcgtttttagc     300
gactatccca tgaggtcaga ggacggcatg gactactggg gcaaagggac cctggtcacc     360
```
gtctcctcag aacccaagac accaaaacca caa        393

<210> SEQ ID NO 59
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln Ala Pro Gly Lys Glu Arg Glu Tyr Val
        35                  40                  45

Ala Ala Val Asn Ser Asn Gly Asp Ser Thr Phe Tyr Ala Asp Ser Ile
    50                  55                  60

Lys Gly Arg Phe Thr Val Ser Arg Asp Ala Ala Lys Asn Thr Val Tyr
65                  70                  75                  80

Leu Gln Met Asn Ser Leu Lys Pro Glu Asp Thr Ala Leu Tyr Tyr Cys
                85                  90                  95

Ala Ala Val Tyr Gly Arg Tyr Tyr Gln Ser Pro Lys Ser Tyr Glu
            100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 60
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
caggtgcagc tggtggagac gggaggagga ttggtgcagg ctgggggctc tctgagactc        60
tcgtgtgcag cctctggacg caccttcagt agctattcca tgggctggtt ccgccaggct       120
ccagggaagg agcgtgagta tgtagcagca gttaactcca atggcgacag tacattctat       180
gccgactcca ttaagggccg attcaccgtc tccagagacg ccgccaagaa cacagtctat       240
ctgcaaatga acagcctgaa acctgaggac acggcccttt attactgtgc agctgtctac       300
ggtagataca cttaccagtc cccaaaatcg tatgagtact ggggccaggg acccaggtc        360 accgtctcct cagaacccaa gacaccaaaa ccacaa                                 396

<210> SEQ ID NO 61
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Leu Gln Leu Val Glu Thr Gly Gly Gly Leu Val Lys Pro Gly Gly
1               5                   10                  15

Ser Leu Arg Leu Ser Cys Val Val Ser Gly Phe Thr Phe Asp Asp Tyr
            20                  25                  30

Arg Met Ala Trp Val Arg Gln Ala Pro Gly Lys Glu Leu Glu Trp Val
                35                  40                  45

Ser Ser Ile Asp Ser Trp Ser Ile Asn Thr Tyr Tyr Glu Asp Ser Val
 50                  55                  60

Lys Gly Arg Phe Thr Ile Ser Thr Asp Asn Ala Lys Asn Thr Leu Tyr
 65                  70                  75                  80

Leu Gln Met Ser Ser Leu Lys Pro Glu Asp Thr Ala Val Tyr Tyr Cys
                85                  90                  95

Ala Ala Glu Asp Arg Leu Gly Val Pro Thr Ile Asn Ala His Pro Ser
            100                 105                 110

Lys Tyr Asp Tyr Asn Tyr Trp Gly Gln Gly Thr Gln Val Thr Val Ser
            115                 120                 125

Ser Glu Pro Lys Thr Pro Lys Pro Gln
            130                 135

<210> SEQ ID NO 62
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
cagttgcagc tcgtggagac tggtggaggc ttggtgaagc ctgggggttc tctgagactc      60
tcctgtgtag tctccggatt cactttttgat gattatcgca tggcttgggt ccgccaggct    120
ccagggaagg agctggagtg ggtgtccagt atagatagtt ggagtatcaa cacatactat    180
gaagactccg tgaagggccg gttcaccatc tccacagaca acgccaagaa tacactgtat    240
ctgcaaatga gcagcctgaa acctgaggac acggccgtgt attactgtgc agcagaggac    300
cgcttaggtg taccgactat taacgcccac ccttcaaaat atgattataa ctactggggg    360
caggggaccc aggtcaccgt ctcctcagaa cccaagacac caaaaccaca a              411

<210> SEQ ID NO 63
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (90)..(90)
<223> OTHER INFORMATION: Any amino acid

<400> SEQUENCE: 63

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Thr Ser Tyr
            20                  25                  30

Ala Met Gly Trp Phe Arg Gln Ala Pro Gly Lys Glu Arg Glu Phe Val
                35                  40                  45

Ala Ser Ile Ser Trp Arg Gly Ser Tyr Thr Tyr Tyr Ser Asp Ser Val
 50                  55                  60

Lys Gly Arg Phe Thr Ile Ser Arg Asp Tyr Ala Glu Asn Thr Met Tyr
 65                  70                  75                  80

Leu Gln Met Asn Ser Leu Lys Pro Glu Xaa Thr Gly Arg Tyr Tyr Cys
                85                  90                  95

Ala Thr Leu Thr Gly Asp Val Ser Val Gly Glu Tyr Asp Asn Arg Gly
            100                 105                 110

Gln Gly Thr Gln Val Thr Val Ser Ser Ala His His Ser Glu Asp Pro
        115                 120                 125

Ser

<210> SEQ ID NO 64
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (269)..(270)
<223> OTHER INFORMATION: a, c, t, g, unknown or other

<400> SEQUENCE: 64
caggtgcagc tggtggagtc cggtggaggc ttggtgcagg ctgggggtc tctgagactc        60 tcctgtgcag cctctggacg caccttcact agttatgcca tgggctggtt ccgccaggct      120
ccagggaagg agcgtgagtt tgtagcgtct attagctggc gcggtagtta cacatactat      180
tcagactccg tgaagggccg attcaccatc tccagagatt acgccgagaa cacgatgtat      240
ctgcaaatga acagcctgaa acctgaggnn acgggcagat attactgtgc aaccttaacc      300
ggcgacgtga gtgtcggcga gtatgacaac cggggccagg gacccaggt cactgtctcc      360 tcagcgcacc acagcgaaga cccctcg                                          387

<210> SEQ ID NO 65
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Ser Val Gln Pro Gly Gly
1               5                   10                  15

Ser Leu Arg Leu Ser Cys Val Ala Ser Gly Phe Thr Phe Thr Asn Tyr
            20                  25                  30

Ala Met Ala Trp Val Arg Gln Val Ser Gly Lys Gly Leu Glu Gly Val
        35                  40                  45

Ala Ala Ile Ser Ser Glu Gly Phe Ile Tyr Ile Pro Asp Ser Val Lys
    50                  55                  60

Gly Arg Phe Thr Ile Ser Arg Asp Asn Ala Lys Asn Thr Val Tyr Leu
65                  70                  75                  80

Gln Met Asp Asn Leu Gln Ser Glu Asp Thr Ala Ile Tyr His Cys Ala
                85                  90                  95

Ala Val Asp Trp Lys Arg Val Ala Ala Met Asn Ser Tyr Asn Met Asp
            100                 105                 110

Tyr Trp Gly Lys Gly Thr Pro Val Thr Val Ser Ala Glu Pro Lys Thr
        115                 120                 125

Pro Lys Pro Gln
    130

<210> SEQ ID NO 66
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66
caggtgcagc tggtggagtc gggggggaggc tcggtgcagc ctggggggtc tctgagactc      60
tcctgtgtag cctctggatt caccttcact aattacgcga tggcctgggt ccgccaggta     120
tcagggaagg ggctcgaggg tgtggccgct attagtagtg agggtttcat atatatccca     180
gactcagtga agggccgatt caccatctcc agagacaacg ccaagaacac ggtgtatcta     240
caaatggaca acctccagtc tgaggatacg gccatatatc actgtgcggc agttgattgg     300
aaacgggtcg ccgcgatgaa cagctacaac atggactact ggggaaaagg gacccccggtc     360 accgtctccg cagaacccaa gacaccaaaa ccacaa                                396

<210> SEQ ID NO 67
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu His Val
        35                  40                  45

Ala Ala Ile Ser Trp Ser Gly Gly Tyr Thr Tyr Tyr Ala Asn Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Gly Val Gln Asp His Ser Asp Ser Leu Gln Asn Trp Gly Gln Gly
            100                 105                 110

Thr Gln Val Thr Val Ser Ser Glu Pro Lys Thr Pro Lys Pro Gln
        115                 120                 125

<210> SEQ ID NO 68
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
cagttgcagc tggtggagtc gggcggagga ttggtgcagg ctggggggtc tctgagactc      60
tcctgtgcag cctctggacg caccttcagt agctatgcca tgggctggtt ccgccaggct     120
ccagggaagg aacgtgagca tgtcgcagct attagctgga gtggtggtta cacatactat     180
gcaaactccg tgaagggccg attcaccatc tccagagaca cgccaagaa cacggtgtat     240

```
ctgcaaatga acagcctgaa acctgaggac acggccgtct attactgtaa tggagttcag    300
gaccatagcg actcccttca gaactggggc caggggaccc aggtcaccgt ctcctcagaa    360
cccaagacac caaaaccaca a                                              381
```

<210> SEQ ID NO 69  
<211> LENGTH: 130  
<212> TYPE: PRT  
<213> ORGANISM: Artificial Sequence  
<220> FEATURE:  
<223> OTHER INFORMATION: Description of Artificial Sequence: Synthetic  
     polypeptide <400> SEQUENCE: 69

```
Gln Leu Gln Leu Val Glu Thr Gly Gly Gly Leu Val Gln Ala Gly Gly
 1               5                  10                  15

Ser Leu Arg Leu Ser Cys Ala Ala Ser Gly Arg Thr Phe Ser Ser Tyr
            20                  25                  30

Ala Val Gly Trp Phe Arg Gln Ala Pro Gly Lys Glu Arg Glu Phe Val
        35                  40                  45

Ala Ala Ile Ser Trp Ser Gly Ser Tyr Ala Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Asn Gly Asp Leu Glu Gly Tyr Ser Asn His Glu Thr Gly Asp Tyr Trp
            100                 105                 110

Gly Gln Gly Thr Gln Val Thr Val Ser Ser Glu Pro Lys Thr Pro Lys
        115                 120                 125

Pro Gln
    130
```

<210> SEQ ID NO 70  
<211> LENGTH: 390  
<212> TYPE: DNA  
<213> ORGANISM: Artificial Sequence  
<220> FEATURE:  
<223> OTHER INFORMATION: Description of Artificial Sequence: Synthetic  
     polynucleotide <400> SEQUENCE: 70

```
cagttgcagc tggtggagac gggaggagga ttggtgcagg ctggggggtc tctgagactc     60
tcctgtgcag cctctggacg cacctttcagt agttatgccg tgggctggtt ccgccaggct   120
ccagggaagg agcgtgagtt tgtcgcagct attagctgga gtggtagtta cgcatactat   180
gcagactccg tgaagggccg attcaccatc tccagagaca cgccaagaa cacggtgtat    240 ctgcaaatga acagcctgaa acctgaggac acggccgtct attactgtaa tggagatctt   300
gagggttata gcaaccatga accggggac tactggggcc aggggaccca ggtcaccgtc    360
tcctcagaac ccaagacacc aaaaccacaa                                     390
```

<210> SEQ ID NO 71  
<211> LENGTH: 130  
<212> TYPE: PRT  
<213> ORGANISM: Artificial Sequence  
<220> FEATURE:  
<223> OTHER INFORMATION: Description of Artificial Sequence: Synthetic  
     polypeptide <400> SEQUENCE: 71

Gln Leu Gln Leu Ala Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Ala Ile Ser Trp Thr Gly Gly Tyr Thr Tyr Tyr Ala Ser Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Tyr Cys
                85                  90                  95

Asn Ala Asp Leu Glu Ser Tyr Ser Glu Tyr Pro Glu Ser Tyr Tyr Trp
            100                 105                 110

Gly Gln Gly Thr Gln Val Thr Val Ser Ser Glu Pro Lys Thr Pro Lys
        115                 120                 125

Pro Gln
    130

<210> SEQ ID NO 72
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
cagttgcagc tggcggagtc gggaggagga ttggtgcagg ctggggggtc tctgagactc      60
tcctgtgcag cctctggacg caccttcagt agctatgcca tgggctggtt ccgccaggct     120
ccagggaagg agcgtgagtt tgtcgcagct attagctgga ctggtggtta cacatactat     180
gcaagctccg tgaagggccg attcaccatc tccagagaca atgccaaaaa cacgatgtat     240
ctgcaaatga acagcctgaa accggaggac acggccgtct attactgtaa tgcagattta     300
gaatcctata gcgagtatcc cgagagctac tactggggcc aggggaccca ggtcaccgtc     360
tcctcagaac ccaagacacc aaaaccacaa                                      390

<210> SEQ ID NO 73
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Ala Glu Ser Gly Gly Gly Leu Val Gln Ala Gly Gly
1               5                   10                  15

Ser Leu Thr Leu Ser Cys Ala Ala Ser Gly Leu Asn Phe Asp Lys Tyr
            20                  25                  30

Ala Ile Gly Trp Tyr Arg Gln Ala Pro Gly Lys Glu Arg Glu Gly Val
        35                  40                  45

Ser Cys Ile Ser Lys Tyr Tyr Asn His Arg Met Tyr Ser Asp Ser Val
    50                  55                  60

Lys Gly Arg Phe Thr Val Ser Ser Asn Tyr Ala Lys Asn Thr Val Tyr
65                  70                  75                  80

```
Leu Gln Met Thr Asn Leu Lys Pro Glu Asp Thr Ala Val Tyr Tyr Cys
                 85                  90                  95

Ala Ala Gly Cys Ile Asp Pro Glu Asp Trp Gly Gln Gly Thr Gln Val
            100                 105                 110

Thr Val Ser Ser Glu Pro Lys Thr Pro Lys Pro Gln
        115                 120
```

<210> SEQ ID NO 74
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74

```
caggtgcagc tggcggagtc gggggggaggc ttggtgcagg ctgggggtc tctgacactc      60 tcctgtgcag cctctggcct caatttcgat aaatatgcca taggctggta ccgccaggcc     120
ccagggaaag agcgtgaggg ggtttcatgt attagtaagt attacaatca tcggatgtat     180
agtgactccg tgaagggccg attcaccgtc tccagtaact atgccaagaa cacggtgtac     240
ctgcaaatga ccaatctgaa accggaggat acggccgttt attactgtgc ggcagggtgt     300
attgacccgg aagattgggg ccaggggacc caggtcaccg tctcctcaga acccaagaca     360
ccaaaaccac aa                                                         372
```

<210> SEQ ID NO 75
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Gln Val Gln Leu Val Glu Thr Gly Gly Gly Val Gln Thr Gly Gly
1               5                   10                  15

Ser Leu Arg Leu Ser Cys Ala Ala Ser Glu Pro Thr Phe Thr Pro Lys
            20                  25                  30

Val Val Gly Trp Phe Arg Gln Ala Pro Val Lys Glu Arg Asp Phe Val
        35                  40                  45

Ala Thr Ile Thr Ile Arg Thr Gly Arg Thr Leu Tyr Ala Asp Ser Val
    50                  55                  60

Lys Gly Arg Phe Thr Ile Ser Gly Asp Gly Ala Asn Asn Thr Val Tyr
65                  70                  75                  80

Leu Gln Met Asn Gly Leu Lys Pro Glu Asp Thr Ala Val Tyr Tyr Cys
                85                  90                  95

Ala Ala Ser Leu Pro Leu Ala Ile Pro Pro Thr Gln Ala Ser Ala Tyr
            100                 105                 110

Glu Tyr Trp Gly Leu Gly Thr Gln Val Thr Val Ser Ser Glu Pro Lys
        115                 120                 125

Thr Pro Lys Pro Gln
    130
```

<210> SEQ ID NO 76
<211> LENGTH: 399
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 76

```
caggtgcagc tggtggagac cggggaggc caggtgcaga ctggggatc tctgagactc      60
tcttgcgcag cctctgaacc caccttcact ccgaaagttg tgggctggtt ccgccaggct    120
ccagtgaagg agcgtgactt tgtagcaact ataacaatcc gtaccggtcg cacactctat    180
gcagattccg tgaagggccg attcaccatc tccggagacg cgccaacaa tacggtgtat     240
ctacaaatga acggcctgaa acctgaggac acggccgttt attactgcgc cgcatctctt    300
ccgctagcaa taccaccgac gcaggcttcg gcatatgaat actggggcct ggggacccag    360
gtcaccgtct cctcagaacc caagacacca aaaccacaa                            399
```

<210> SEQ ID NO 77
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Gln Val Gln Leu Val Glu Thr Gly Gly Gly Leu Val Gln Pro Gly Gly
1               5                   10                  15
Ser Leu Arg Leu Ser Cys Ser Val Ser Gly Leu His Phe Arg Phe Ala
            20                  25                  30
Asn Met Gly Trp Phe Arg Gln Ala Pro Gly Lys Gln Arg Glu Leu Val
        35                  40                  45
Ala Tyr Ile Thr Thr Gly Asp Asn Thr Asn Tyr Val Asp His Val Lys
    50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ile Val Asn Ala Leu Gly Glu Phe Asn Pro Arg Asn Asp Trp Gly Gln
            100                 105                 110
Gly Thr Gln Val Thr Val Ser Ser Glu Pro Lys Thr Pro Lys Pro Gln
        115                 120                 125
```

<210> SEQ ID NO 78
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 78

```
caggtgcagc tggtggagac gggggaggc ttggtgcagc ctggggggtc tctgagactc       60
tcctgttcag tctctggcct ccacttcagg ttcgcgaaca tgggatggtt cgccaggct     120
ccagggaagc agcgcgagtt ggtcgcatat attactactg gtgataacac taactatgta    180
gaccacgtga agggccgatt caccatctcc agagacaacg ccaagaacac ggtgtatctg    240
caaatgaaca gcctgaaacc tgaagacacg gccgtctact actgtaatat agtcaatgcg    300
ctgggggagt tcaatccccg aaacgactgg ggccagggga cccaggtcac cgtctcctca    360
gaacccaaga caccaaaacc acaa                                            384
```

<210> SEQ ID NO 79
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

```
Gln Val Gln Leu Val Glu Thr Gly Gly Gly Trp Val Gln Ala Gly Gly
1               5                   10                  15

Ser Leu Arg Leu Ser Cys Ala Ala Ser Gly Arg Ala Ala Ser Gly Asn
            20                  25                  30

Ala Met Ala Trp Phe Arg Gln Ala Pro Gly Lys Glu Arg Glu Phe Val
        35                  40                  45

Ala Leu Ile Ser Trp Ser Gly Gly Arg Pro Tyr Tyr Ala Asn Ser Val
    50                  55                  60

Lys Gly Arg Phe Ala Ile Ser Arg Asp Asn Ala Thr Asn Thr Val Tyr
65                  70                  75                  80

Leu Gln Met Asn Arg Leu Lys Pro Glu Asp Thr Ala Val Tyr Tyr Cys
                85                  90                  95

Ala Ala Ser Pro Thr Ile Ala Ile Leu Pro Thr Pro Tyr Asp Tyr Trp
            100                 105                 110

Gly Gln Gly Thr Gln Val Thr Val Ser Ser Glu Pro Lys Thr Pro Lys
        115                 120                 125

Pro Gln
    130
```

<210> SEQ ID NO 80
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

```
caggtgcagc tggtggagac gggtggggggg tgggtacagg ctgggggctc tctgagactc      60
tcctgtgcag cctctggacg cgccgccagt ggaaatgcca tggcctggtt ccgccaggct     120
ccaggaaagg agcgtgagtt tgtagcattg attagttgga gtggtggtcg cccatactat     180
gcaaactccg tgaagggccg attcgccatc tccagagaca acgccacgaa tacggtgtat     240
ctgcaaatga acagactgaa acctgaggac acggccgttt attactgtgc agcgtcgcct     300
accatagcga tactacctac tccgtatgac tactggggcc aggggaccca ggtcaccgtc     360
tcctcagaac ccaagacacc aaaaccacaa                                      390
```

<210> SEQ ID NO 81
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Val Gln Leu Val Glu Thr Gly Gly Gly Leu Val Gln Ala Gly Ala
1               5                   10                  15

Ser Leu Arg Leu Ser Cys Ala Ala Ser Gly Arg Thr Phe Ser Thr Asp
            20                  25                  30
```

His Met Gly Trp Phe Arg Gln Ala Pro Gln Lys Glu Arg Glu Phe Val
       35                  40                  45

Ala Ala Ile Asn Ala Trp Ser Gly Leu Ser Ile Tyr Tyr Ala Asp Ser
 50                  55                  60

Val Lys Gly Arg Phe Thr Ile Ser Arg Asp Asn Asp Lys Lys Thr Ala
 65                  70                  75                  80

Tyr Leu Gln Met Asn Ser Leu Lys Pro Glu Asp Thr Ala Val Tyr Tyr
                 85                  90                  95

Cys Ala Ala Lys Glu Met Gly Arg Gly Trp Val Pro Gln Ser Ser Asp
             100                 105                 110

Asp Tyr Asp Ala Trp Gly Gln Gly Thr Gln Val Thr Val Ser Ser Glu
             115                 120                 125

Pro Lys Thr Pro Lys Pro Gln
        130                 135

<210> SEQ ID NO 82
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggtgcagc tggtggagac ggggggagga ttggtgcagg ctggggcctc tctgagactc      60
tcctgtgcag cctctggacg caccttcagt accgatcaca tgggctggtt ccgccaggct     120
ccacagaagg agcgtgagtt tgtggcagca ataaatgcat ggagtggact cagcatttac     180
tatgcagact ccgtgaaggg ccgattcacc atctccagag acaacgacaa gaaaacggca     240
tatctacaaa tgaacagcct gaaacctgag gacacggccg tttattactg tgcagccaag     300
gagatgggta ggggttgggt gccacagagc tcagacgact atgacgcctg gggccagggg     360
acccaggtca ccgtctcctc agaacccaag acaccaaaac cacaa                     405

<210> SEQ ID NO 83
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Glu Thr Gly Gly Gly Leu Val Gln Ala Gly Gly
 1               5                  10                  15

Ser Leu Arg Leu Ser Cys Ala Val Ser Gly Arg Thr Phe Ser Ser Tyr
             20                  25                  30

Ala Met Ala Trp Phe Arg Gln Ala Pro Gly Lys Glu Arg Asp Phe Val
         35                  40                  45

Ala Ala Ile Ser Trp Ser Gly Gly Ala Pro His Tyr Glu Asp Ser Val
 50                  55                  60

Lys Gly Arg Phe Thr Ile Ser Arg Asp Asn Ala Lys Asn Met Val Tyr
 65                  70                  75                  80

Leu Gln Met Asn Ser Leu Lys Pro Asp Asp Thr Ala Val Tyr Tyr Cys
                 85                  90                  95

Ala Ala Ala Lys Ala Gly Tyr Tyr Ser Gly Ser Tyr Tyr Val Gly Gly
             100                 105                 110

Gly Met Tyr Asp Tyr Trp Gly Gln Gly Thr Gln Val Thr Val Ser Ser 115                 120                 125
Glu Pro Lys Thr Pro Lys Pro Gln
    130                 135

<210> SEQ ID NO 84
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 84
caggtgcagc tggtggagac tggaggagga ttggtgcagg ctgggggctc tctgagactc     60
tcctgtgcag tctctggacg caccttcagt agctatgcca tggcctggtt ccgccaggct    120
ccagggaagg agcgtgattt tgtagcagct attagctgga gtggtggtgc cccacactat    180
gaagactccg tgaagggccg attcaccatc tccagagaca cgccaagaa catggtatat    240 ctccaaatga acagcctgaa acctgacgac acggccgttt actactgtgc agcagcgaaa    300
gcaggatact atagtggtag ttactacgtg ggggggggta tgtatgacta ctggggccag    360
gggacccagg tcaccgtctc ctcagaaccc aagacaccaa aaccacaa                 408

<210> SEQ ID NO 85
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Glu Thr Gly Gly Leu Val Gln Ala Gly Gly Ser
1               5                   10                  15

Leu Arg Leu Ser Cys Ala Ala Ser Gly Ser Ile Gly Arg Val Asp Asn
            20                  25                  30

Met Gly Trp Tyr Arg Gln Thr Pro Gly Lys Glu Arg Glu Arg Val Ala
        35                  40                  45

Ile Ile Thr Gly Gly Gly Thr Ala Ile Tyr Ala Asp Thr Val Lys Gly
    50                  55                  60

Arg Phe Thr Val Ser Arg Asp Asn Ala Lys Asn Thr Ile Tyr Leu Gln
65                  70                  75                  80

Met Asn Ser Val Lys Pro Glu Asp Thr Ala Val Tyr Phe Cys Asn Ala
                85                  90                  95

Asp Ile Ser Arg Ser Ile Glu Ser Ile Val Tyr Arg Ser Tyr Trp Gly
            100                 105                 110

Gln Gly Thr Gln Val Thr Val Ser Ser Glu Pro Lys Thr Pro Lys Pro
        115                 120                 125

Gln

<210> SEQ ID NO 86
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tggtggagac aggaggcttg gtgcaggctg ggggtctct gagactctcc     60

```
tgtgcagcct ccggaagcat cggcagggtc gataacatgg gctggtaccg ccaaactcca    120
gggaaagagc gcgagcgggt cgcaatcatt actggaggcg gtaccgcgat ctatgcagac    180
accgtgaagg gccgattcac cgtctccaga gacaacgcca agaacacaat atatctacaa    240
atgaacagcg tgaaacctga ggacacagcc gtctatttct gtaatgccga catcagtcgt    300
agtattgagt ccatcgtcta tcgttcctac tggggccagg ggacccaggt caccgtctcc    360
tcagaaccca agacaccaaa accacaa                                         387

<210> SEQ ID NO 87
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Glu Thr Gly Gly Gly Leu Val Gln Pro Gly Gly
1               5                   10                  15

Ser Leu Arg Leu Ser Cys Ala Ala Ser Gly Asn Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Asn Ser Gly Ser Thr Asn Tyr Glu Asp Ser Val Lys
    50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Phe Asp Leu Val Ala Gly Thr Arg Leu Gly Ser Trp Gly Gln Gly
            100                 105                 110

Thr Gln Val Thr Val Ser Ser Glu Pro Lys Thr Pro Lys Pro Gln
        115                 120                 125

<210> SEQ ID NO 88
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88
caggtgcagc tggtggagac ggggggaggc ttggtgcagc ctggggggtc tctgagactc    60
tcctgtgcag cctctggaaa catcttcagt atcaatgcca tggctggta ccgccaggct    120 ccagggaagc agcgcgagtt ggtcgcagct attagtaata gtggtagcac aaactatgaa    180
gactccgtga agggccgatt caccgtctcc agagacaacg ccaagaacac ggtgtatctg    240
caaatgaaca gcctgaaacc tgaggacacg gccgtctatt actgtaatgc cttcgattta    300
gtagctggta ctaggctggg gtcctggggc caggggaccc aggtcaccgt ctcctcggaa    360
cccaagacac aaaaccaca a                                                381

<210> SEQ ID NO 89
<211> LENGTH: 135
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 89

Gln Val Gln Leu Val Glu Ser Gly Gly Gly Leu Val Gln Pro Gly Gly
1               5                   10                  15

Ser Leu Arg Leu Ser Cys Ala Ala Ser Glu Phe Thr Leu Glu His Ala
            20                  25                  30

Ala Val Gly Trp Phe Arg Gln Ala Pro Gly Lys Glu Arg Glu Gly Val
        35                  40                  45

Ser Cys Ile Ser Ser Arg Asp Ser Asn Thr Tyr Tyr Ala Asp Ser Val
    50                  55                  60

Lys Gly Arg Phe Thr Ile Ser Arg Asp Asn Ala Glu Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asp Val Pro Cys Trp Asp Gly Ser Asn Trp Ser Leu Gly His
            100                 105                 110

Glu Tyr Asp Tyr Trp Gly Gln Gly Thr Gln Val Thr Val Ser Ser Glu
        115                 120                 125

Pro Lys Thr Pro Lys Pro Gln
    130                 135

<210> SEQ ID NO 90
<211> LENGTH: 405
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 90
caggtgcagc tggtggagtc ggggggaggc ttggtgcagc ctgggggtc tctgagactc      60 tcctgtgcag cctctgaatt cactttggaa catgccgccg taggctggtt ccgccaggcc    120
ccagggaagg agcgcgaggg ggtctcttgt attagtagtc gtgatagtaa cacatactat    180
gcagactccg tgaagggccg attcaccatc tccagagaca tgccgaaaa cacggtatat     240 ctgcaaatga acagcctgaa acctgaggac acggccgttt attactgtgc gacagatgtc    300
ccctgctggg acggtagtaa ctggtccctc ggtcatgagt atgactactg gggccagggg    360
acccaggtca ccgtctcctc agaacccaag acaccaaaac cacaa                    405

<210> SEQ ID NO 91
<211> LENGTH: 131
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 91

Gln Val Gln Leu Val Glu Thr Gly Gly Gly Leu Val Gln Pro Gly Gly
1               5                   10                  15

Ser Leu Arg Leu Ser Cys Ala Ala Ser Gly Ser Ile Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ile Arg Gly Asn Thr Val Tyr Gly Asp Ser Val Lys
    50                  55                  60

```
Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Lys Ser Thr Pro Ser Leu Tyr Ala Ala Gly Tyr Gly Val Asp Tyr
            100                 105                 110

Trp Gly Glu Gly Thr Leu Val Thr Val Ser Ser Glu Pro Lys Thr Pro
        115                 120                 125

Lys Pro Gln
    130

<210> SEQ ID NO 92
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92
caggtgcagc tggtggagac ggggggaggc ttggtgcagc ctgggggtc tctgagactc      60 tcctgtgcag cctctggaag catctccagt atcaatgcca tgggctggta ccgccaggct     120
ccagggaagc agcgcgagtt ggtcgcggct attactattc gtggtaacac agtctatgga     180
gactccgtga agggccgatt caccgtctcc agagacaacg ccaagaacac ggtgtatctg     240
caaatgaaca gcctgaaacc tgaggacacg gccgtctatt actgtaatgc caagtcgacc     300
ccgagcttgt acgccgccgg ctacggcgtg gactactggg gcgaagggac cctagtcacc     360
gtctcctcag aacccaagac accaaaacca caa                                  393

<210> SEQ ID NO 93
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Gln Val Gln Leu Val Glu Thr Gly Gly Gly Leu Val Gln Ala Gly Gly
1               5                   10                  15

Ser Leu Arg Leu Ser Cys Ala Ala Ser Gly Asn Ile Ser Ser Ile Asn
            20                  25                  30

Ala Met Ala Trp Tyr Arg Gln Ala Pro Gly Gln Gln Arg Glu Leu Val
        35                  40                  45

Ala Gly Ile Thr Ser Gly Gly Arg Thr Gln Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Glu Ser Leu Lys Pro Glu Asp Thr Ala Val Tyr Tyr Cys Asn
                85                  90                  95

Ala Lys Ser Pro Pro Ser Thr Trp Ala Thr Gly Gly Gly Met Asn Tyr
            100                 105                 110

Trp Gly Lys Gly Thr Leu Val Thr Val Ser Ser Glu Pro Lys Thr Pro
        115                 120                 125

Lys Pro Gln
    130
```

<210> SEQ ID NO 94
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
caggtgcagc tggtggagac ggggggaggc ttggtgcagg ctggggggtc tctgagactc       60
tcctgtgcag cctctgggaa catctccagt atcaatgcca tggcctggta ccgccaggct      120
ccagggcagc agcgcgagct ggtcgcaggg attactagtg gtggcaggac acaatataca      180
gactccgtga agggccgatt caccatctcc agagacaacg ccaagaacac ggtgtatctg      240
caaatggaga gtctgaaacc tgaggacaca gccgtctatt actgtaatgc aaaaagccct      300
cccagtacct gggccacggg gggggcatg aactactggg gcaaaggga cctggtcacc        360 gtctcctcag aacccaagac accaaaacca caa                                   393

<210> SEQ ID NO 95
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Gln Val Gln Leu Val Glu Thr Gly Gly Ala Leu Val Gln Ala Gly Gly
1               5                   10                  15

Ser Leu Arg Leu Ser Cys Ala Ala Ser Glu Thr Ser Ser Val Ser Leu
            20                  25                  30

Ser Trp Met Gly Trp Tyr Arg Gln Ala Pro Gly Lys Glu Arg Glu Leu
        35                  40                  45

Val Ala Gly Ile Asn Arg Asp Arg Pro Lys Tyr Lys Glu Ser Val Lys
    50                  55                  60

Gly Arg Phe Thr Ile Ser Arg Asp Asn Ala Gln Asn Thr Val Tyr Leu
65                  70                  75                  80

Gln Met Asn Ser Leu Lys Pro Glu Asp Thr Ala Val Tyr Tyr Cys Asn
                85                  90                  95

Thr Val Pro Pro Arg Gly Asp Tyr Trp Gly Gln Gly Thr Gln Val Thr
            100                 105                 110

Val Ser Ser Glu Pro Lys Thr Pro Lys Pro Gln
        115                 120

<210> SEQ ID NO 96
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
caggtgcagc tggtggagac aggaggagcc ttggtgcagg cggggggtc tctgagactc        60 tcctgtgcag cctctgagac atcttcagta tcgctatcat ggatgggctg gtaccgccag      120
gctcctggga aggagcgcga gttggtcgca ggcattaatc gtgataggcc aaagtataaa      180
gagtccgtga agggccgatt caccatctcc agagacaacg cccagaatac ggtgtatctg      240

```
caaatgaaca gcctgaaacc tgaggacaca gccgtctatt actgtaatac ggttccacca        300
cgcggcgact actggggcca ggggacccag gtcaccgtct cctcagaacc caagacacca        360
aaaccacaa                                                                369
```

<210> SEQ ID NO 97
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Glu Ser Gly Gly Gly Leu Val Gln Pro Gly Gly
1               5                   10                  15

Ser Leu Arg Val Ser Cys Val Ala Ser Gly Asn Ile Ser Val Ala
            20                  25                  30

Ala Met Ala Trp Tyr Arg Gln Arg Pro Glu Lys Arg Arg Glu Leu Val
        35                  40                  45

Ala Val Ile Thr Asn Ser Gly Gly Thr Ala Tyr Thr Asp Ser Val Arg
    50                  55                  60

Gly Arg Phe Thr Ile Ser Arg Asp Asn Val Lys Ser Thr Val Tyr Leu
65                  70                  75                  80

Gln Met Asn Asn Leu Lys Pro Glu Asp Thr Ala Val Tyr Tyr Cys Asn
                85                  90                  95

Ala Arg Gly Leu Asp Ala Gly Ser Gly Arg Ile Asp Tyr Trp Gly Gln
            100                 105                 110

Gly Thr Gln Val Thr Val Ser Ser Glu Pro Lys Thr Pro Lys Pro Gln
        115                 120                 125

<210> SEQ ID NO 98
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
caggtgcagc tggtggagtc cggtggaggc ttggtgcagc ctgggggggtc tctgagagtc        60 tcctgtgtag cctctggaaa catctccagt gtcgctgcca tggcctggta ccgccagaga        120
ccagagaagc gccgcgaatt ggtcgcagtc attactaaca gcggtggcac agcctataca        180
gactccgtga ggggccgatt caccatctcc agagacaatg tcaagtcaac ggtgtatcta        240
caaatgaata acctgaaacc tgaggacaca gccgtgtatt actgtaatgc gagggggtta        300
gacgccgggt cagggcgcat tgactactgg ggccagggaa cccaggtcac cgtctcctca        360
gaacccaaga caccaaaacc acaa                                               384
```

<210> SEQ ID NO 99
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Val Glu Ser Gly Gly Gly Leu Ala Gln Thr Gly Gly
1               5                   10                  15

Ser Leu Asn Leu Ser Cys Ala Ala Ser Gly Pro Thr Phe Ser Gly Tyr
            20                  25                  30

Gly Met Gly Trp Phe Arg Gln Ala Pro Gly Lys Glu Arg Glu Phe Leu
        35                  40                  45

Ala Val Ile Arg Trp Ser Val Gly Asn Thr Leu Tyr Ala Glu Ser Val
    50                  55                  60

Lys Gly Arg Phe Thr Ile Ser Arg Asp Lys Val Lys Asn Thr Gly Tyr
65                  70                  75                  80

Leu Gln Ile Asp Asn Leu Lys Pro Glu Asp Thr Ala Val Tyr Tyr Cys
                85                  90                  95

Ala Ala Gly Ala Tyr Val Thr Thr Arg Ser Arg Asp Tyr Ala Tyr Trp
            100                 105                 110

Gly Gln Gly Thr Gln Val Thr Val Ser Ser Glu Pro Lys Thr Pro Lys
        115                 120                 125

Pro Gln
    130

<210> SEQ ID NO 100
<211> LENGTH: 390
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
caggtgcagc tggtggagtc ggggggagga ttggcgcaga ctgggggctc tctgaacctc     60
tcctgtgcag cctctggacc gactttcagc ggctatggta tgggctggtt ccgccaggct    120
ccagggaagg agcgtgaatt ctagcggta attcgctgga gtgtaggtaa tacattgtat     180
gcagagtccg tcaagggccg attcaccatc tccagagaca aggtcaagaa cacggggtat    240
ctgcaaatag acaacctgaa acccgaggac acggccgttt attactgtgc agcgggggcg    300
tacgtaacta cgaggtcccg cgactatgcc tactggggcc aggggaccca ggtcaccgtc    360
tcctcagaac ccaagacacc aaaaccacaa                                      390

<210> SEQ ID NO 101
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Val Glu Thr Gly Gly Arg Gln Val Gln Thr Gly Asp
1               5                   10                  15

Ser Leu Asn Leu Ser Cys Ala Ala Ser Glu His Thr Phe Ser Pro Lys
            20                  25                  30

Val Met Gly Trp Phe Arg Gln Ala Pro Gly Lys Gly Arg Glu Phe Val
        35                  40                  45

Ala Thr Ile Thr Ile Arg Gly Gly Arg Thr Leu Tyr Ala Asp Ser Val
    50                  55                  60

Lys Gly Arg Phe Ala Ile Ser Lys Asp Gly Ala Lys Asn Thr Val Tyr
65                  70                  75                  80

Leu Gln Met Asn Ser Leu Lys Pro Glu Asp Thr Ala Val Tyr Tyr Cys
                85                  90                  95

```
Ala Ala Ser Arg Glu Leu Ala Ile Pro Pro Thr Gln Pro Ser Ala Tyr
                100                 105                 110

Asp His Trp Gly Gln Gly Thr Gln Val Thr Val Ser Ser Ala His His
        115                 120                 125

Ser Glu Asp Pro Ser
    130

<210> SEQ ID NO 102
<211> LENGTH: 399
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
caggtgcagc tcgtggagac cggcggacgt caggtgcaga ctggggactc tctgaacctc    60
tcttgcgcag cttctgaaca caccttcagt cctaaagtta tggggtggtt ccgccaggct   120
ccaggcaagg ggcgtgagtt tgtagcaact atcacaatcc gtggcggtcg cacactctat   180
gcagattccg tgaagggccg atttgccatc tccaaagacg cgccaagaa tacggtgtat    240 ctgcaaatga acagtctgaa acctgaggac acggccgttt attactgtgc agcaagtcgt   300
gagctagcga taccaccgac gcagccttcg gcatacgacc actggggcca ggggacccag   360
gtcaccgtct cctcagcgca ccacagcgaa gacccctcg                         399

<210> SEQ ID NO 103
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Ala Glu Ser Gly Gly Gly Leu Val Gln Pro Gly Gly
1               5                   10                  15

Ser Leu Gly Leu Ser Cys Val Val Ala Ser Glu Arg Ser Ile Asn Asn
            20                  25                  30

Tyr Gly Met Gly Trp Tyr Arg Gln Ala Pro Gly Lys Gln Arg Glu Leu
        35                  40                  45

Val Ala Gln Ile Ser Ser Gly Gly Thr Thr Asn Tyr Ala Asp Ser Val
    50                  55                  60

Glu Gly Arg Phe Thr Ile Ser Arg Asp Asn Val Lys Lys Met Val His
65                  70                  75                  80

Leu Gln Val Asn Ser Leu Lys Pro Glu Asp Thr Ala Val Tyr Tyr Cys
                85                  90                  95

Asn Ser Leu Leu Arg Thr Phe Ser Trp Gly Gln Gly Thr Gln Val Thr
            100                 105                 110

Val Ser Ser Glu Pro Lys Thr Pro Lys Pro Gln Ala Ile Ala Gly Gly
        115                 120                 125

Gly Gly Ser Gly Gly Gly Gly Ser Gly Gly Gly Ser Leu Gln Gly
    130                 135                 140

Gln Val Gln Leu Val Glu Ser Gly Gly Gly Leu Val Gln Pro Gly Gly
145                 150                 155                 160

Ser Leu Ser Val Ser Cys Ala Ala Ser Gly Ser Ile Ala Arg Pro Gly
                165                 170                 175

Ala Met Ala Trp Tyr Arg Gln Ala Pro Gly Lys Glu Arg Glu Leu Val
```

```
            180             185                 190
Ala Ser Ile Thr Pro Gly Gly Leu Thr Asn Tyr Ala Asp Ser Val Thr
            195                 200                 205

Gly Arg Phe Thr Ile Ser Arg Asp Asn Ala Lys Arg Thr Val Tyr Leu
        210                 215                 220

Gln Met Asn Ser Leu Gln Pro Glu Asp Thr Ala Val Tyr Tyr Cys His
225                 230                 235                 240

Ala Arg Ile Ile Pro Leu Gly Leu Gly Ser Glu Tyr Arg Asp His Trp
                245                 250                 255

Gly Gln Gly Thr Gln Val Thr Val Ser Ser Ala His His Ser Glu Asp
                260                 265                 270

Pro Ser
```

<210> SEQ ID NO 104
<211> LENGTH: 822
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 104

```
caggtgcagc tggcggagtc gggcggaggc ttggtgcagc ctggggggtc tctgggactc      60
tcctgtgtag tcgcctctga agaagcatc aataattatg catgggctg gtaccgccag       120
gctccaggga agcagcgcga gttggtcgcg caaattagta gtggtggtac cacaaattat     180
gcagactccg tagagggccg attcaccatc tccagagaca cgtcaagaa aatggtgcat     240
cttcaagtga acagcctgaa acctgaggac acggccgtct attactgtaa ttcgctactc     300
cgaactttt cctggggcca ggggacccag gtcaccgtct cctcggaacc caagacacca     360
aaaccacaag cgatcgctgg tggaggcggt tcaggcggag gtggctctgg cggtggcggt     420
tccctgcagg tcagktgca gctsgyggag tccgggggcg gcttggtgca gcccgggggg     480
tctctgagtg tctcctgtgc agcctctgga agcatcgcaa gaccaggtgc catggcctgg     540
taccgccagg ctccagggaa ggagcgcgag ttggtcgcgt ctattacgcc tggtggtctt     600
acaaactatg cggactccgt gacgggccga ttcaccattt ccagagacaa cgccaagagg     660
acggtgtatc tgcagatgaa cagcctccaa cccgaggaca cggccgtcta ttactgtcat     720
gcacgaataa ttcccctagg acttgggtcc gaatacaggg accactgggg ccaggggact     780
caggtcaccg tctcctcagc gcaccacagc gaagaccctt cg                        822
```

<210> SEQ ID NO 105
<211> LENGTH: 286
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Ala Glu Ser Gly Gly Gly Leu Val Gln Pro Gly Gly
1               5                   10                  15

Ser Leu Gly Leu Ser Cys Val Val Ala Ser Glu Arg Ser Ile Asn Asn
            20                  25                  30

Tyr Gly Met Gly Trp Tyr Arg Gln Ala Pro Gly Lys Gln Arg Glu Leu
        35                  40                  45

Val Ala Gln Ile Ser Ser Gly Gly Thr Thr Asn Tyr Ala Asp Ser Val
```

```
                50                  55                  60
Glu Gly Arg Phe Thr Ile Ser Arg Asp Asn Val Lys Lys Met Val His
 65                  70                  75                  80

Leu Gln Val Asn Ser Leu Lys Pro Glu Asp Thr Ala Val Tyr Tyr Cys
                 85                  90                  95

Asn Ser Leu Leu Arg Thr Phe Ser Trp Gly Gln Gly Thr Gln Val Thr
                100                 105                 110

Val Ser Ser Glu Pro Lys Thr Pro Lys Pro Gln Ala Ile Ala Gly Gly
            115                 120                 125

Gly Gly Ser Gly Gly Gly Ser Gly Gly Gly Ser Leu Gln Gly
        130                 135                 140

Gln Val Gln Leu Ala Glu Ser Gly Gly Gly Leu Val Gln Ala Gly
145                 150                 155                 160

Gly Ser Leu Arg Leu Ser Cys Ala Ala Ser Gly Arg Thr Phe Ser Gly
                165                 170                 175

Tyr Ala Met Gly Trp Phe Arg Gln Ala Pro Gly Lys Glu Arg Glu Phe
                180                 185                 190

Val Ala Asp Ile Ser Trp Ser Gly His Asn Thr Tyr Tyr Gly Asp Ser
            195                 200                 205

Val Lys Gly Arg Phe Thr Ile Ser Arg Asp Thr Ala Lys Asn Thr Val
        210                 215                 220

Tyr Leu Gln Met Asn Ser Leu Lys Pro Glu Asp Thr Ala Val Tyr Tyr
225                 230                 235                 240

Cys Ala Ala Glu Gly Ala Arg Thr His Leu Ser Asp Ser Tyr Tyr Phe
                245                 250                 255

Pro Gly Leu Trp Ala Glu Pro Pro Val Gly Tyr Trp Gly Gln Gly Thr
                260                 265                 270

Gln Val Thr Val Ser Ser Glu Pro Lys Thr Pro Lys Pro Gln
            275                 280                 285

<210> SEQ ID NO 106
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
caggtgcagc tggcggagtc gggcggaggc ttggtgcagc ctgggggtc tctgggactc     60 tcctgtgtag tcgcctctga agaagcatc aataattatg catgggctg gtaccgccag    120 gctccaggga agcagcgcga gttggtcgcg caaattagta gtggtggtac cacaaattat    180
gcagactccg tagagggccg attcaccatc tccagagaca acgtcaagaa aatggtgcat    240
cttcaagtga acagcctgaa acctgaggac acggccgtct attactgtaa ttcgctactc    300 cgaactttt cctggggcca ggggacccag gtcaccgtct cctcggaacc caagacacca    360
aaaccacaag cgatcgctgg tggaggcggt tcaggcggag gtggctctgg cggtggcggt    420
tccctgcagg gtcaggtgca gctcgcggag tcgggtgggg gaggactggt gcaggctggg    480
ggctctctga gactctcctg tgcagcctct ggacgcacct tcagtggcta tgccatgggc    540
tggttccgcc aggctccggg gaaggagcgt gagtttgtag ccgatattag ctggagtggt    600
cataacacgt actatggaga ctccgtgaag ggccgattca ccatctccag agacaccgcc    660
aagaacacgg tgtatctgca aatgaacagc ctgaaacctg aggacacggc cgtttattac    720
```

```
tgtgcagcgg agggggcccg tacacacctt agtgatagtt actacttccc gggcctctgg    780
gccgaacccc ccgtgggcta ctggggccag gggacccagg tcactgtctc ctcagaaccc    840
aagacaccaa aaccacaa                                                   858
```

<210> SEQ ID NO 107
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Gln Val Gln Leu Val Glu Ser Gly Gly Gly Val Gln Ala Gly Gly
1               5                   10                  15

Ser Leu Arg Leu Thr Cys Thr Gly Ser Gly Arg Ser Phe Ala Leu Tyr
            20                  25                  30

Tyr Met Ala Trp Phe Arg Gln Ala Pro Gly Lys Glu Arg Glu Phe Val
        35                  40                  45

Ala Ala Ile Ser His Asn Ser Leu Ser Ala Ile Val Ala Asp Ser Leu
    50                  55                  60

Lys Gly Arg Phe Thr Ile Ser Arg Asp Asn Ala Arg Asn Gln Val Val
65                  70                  75                  80

Leu Gln Met Asn Ser Leu Lys Pro Glu Asp Thr Ala Val Tyr Tyr Cys
                85                  90                  95

Ala Ala Asp Phe Ser Pro Ser Thr Tyr Asn Thr Asn Tyr Tyr Arg Thr
            100                 105                 110

Gly Ser Tyr Gln Tyr Trp Gly Gln Gly Thr Gln Val Thr Val Ser Ser
        115                 120                 125

Glu Pro Lys Thr Pro Lys Pro Gln
    130                 135
```

<210> SEQ ID NO 108
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
caggtgcagc tggtggagtc ggggggagga tcggtgcagg ctggggggctc tctgagactc    60 acctgtacag gctctggacg cagtttcgcg ctctattaca tggcctggtt ccgccaggct   120
ccagggaagg agcgtgagtt tgtagcagct atcagccaca attcgttaag cgcaatcgtt   180
gcagactccc taaagggccg attcaccatc tccagagaca cgccagaaa ccaggtggtt   240 ctacaaatga acagcctgaa acctgaggac acggccgttt attactgtgc agcagacttt   300
tcgccctcga cctataatac aaattactac cgcaccggtt cgtatcagta ttggggccag   360
gggacccagg tcaccgtctc ctcagaaccc aagacaccaa aaccacaa                408
```

<210> SEQ ID NO 109
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Gln Val Gln Leu Val Glu Thr Gly Gly Gly Leu Val Gln Ala Gly Gly
1               5                   10                  15

Ser Leu Gly Leu Ser Cys Ala Ala Ser Gly Leu Ser Phe Asn Trp Tyr
            20                  25                  30

Asp Val Gly Trp Phe Arg Gln Ala Pro Gly Lys Glu Arg Glu Phe Val
        35                  40                  45

Ala Ser Arg Ser Ser Gly Gly Gly Ser Thr Tyr Tyr Gly Asp Ser Val
    50                  55                  60

Lys Gly Arg Phe Ser Ile Ser Thr Asp Asn Ala Lys Asn Thr Ala Tyr
65                  70                  75                  80

Leu Gln Met Asn Ser Leu Lys Pro Glu Asp Thr Ala Val Tyr Tyr Cys
                85                  90                  95

Ala Ala Asp Trp Thr Gly Arg Ala Gly Phe Ser Val Gly Tyr Tyr Arg
            100                 105                 110

Pro Asp Glu Tyr Asp Tyr Trp Gly Gln Gly Thr Gln Val Thr Val Ser
        115                 120                 125

Glu Glu Pro Lys Thr Pro Lys Pro Gln
    130                 135
```

<210> SEQ ID NO 110
<211> LENGTH: 411
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
caggtgcagc tggtggagac gggaggagga ttggtgcagg ctgggggctc tctgggactc    60
tcctgtgcag cctctggact gtcctttaat tggtatgacg tgggctggtt ccgccaggct   120
ccagggaagg agcgtgagtt tgtagcgtct cgtagctcgg gtggtggtag tacatattat   180
ggagactccg tgaagggccg attcagcatc tccacagaca atgccaagaa cacggcgtat   240
ctgcaaatga acagcctaaa acctgaggac acggccgttt actactgtgc agcagattgg   300
acaggccgcg caggcttcag tgttggttac taccggcccg atgagtatga ctactggggc   360
caggggaccc aggtcaccgt ctccgaagaa cccaagacac aaaaccaca a              411
```

<210> SEQ ID NO 111
<211> LENGTH: 134
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

```
Gln Val Gln Leu Val Glu Thr Gly Gly Gly Leu Val Gln Pro Gly Gly
1               5                   10                  15

Ser Leu Arg Leu Ser Cys Val Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ser Cys Met Ser Ser Gly Asp Gly Ser Thr Tyr Tyr Thr Asn Ser Val
    50                  55                  60

Lys Gly Arg Phe Thr Ile Ser Arg Asp Asn Ala Gln Asn Thr Val Tyr
65                  70                  75                  80
```

-continued

```
Leu Gln Met Asn Ser Leu Lys Pro Glu Asp Thr Ala Val Tyr Tyr Cys
                85                  90                  95

Ala Ala Asp Gly Phe Asp Tyr Cys Ser Ala Tyr Val Pro Gly Arg Gly
            100                 105                 110

Met Asn Tyr Ser Gly Lys Gly Thr Leu Val Thr Val Ser Ser Glu Pro
        115                 120                 125

Lys Thr Pro Lys Pro Gln
    130
```

<210> SEQ ID NO 112
<211> LENGTH: 402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 112

```
caggtgcagc tggtggagac gggggggaggc ttggtgcagc ctgggggggtc tctgagactc    60 tcctgtgtag cctctggatt cactttggat tcatatgcca taggctggtt ccgccaggcc   120
ccagggaagg agcgtgaggg ggtctcatgt atgagtagtg gtgatggtag cacatactat   180
acaaactccg tgaagggccg attcaccatc tccagagaca acgcccagaa cacggtgtat   240
ctgcaaatga acagcctgaa acctgaggac acagccgttt attactgtgc agcagatggg   300
tttgactatt gttcagctta tgtgcccggg agaggcatga actactcggg caaagggacc   360
ctggtcaccg tctcctcaga acccaagaca ccaaaaccac aa                      402
```

<210> SEQ ID NO 113
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

```
Gln Val Gln Leu Val Glu Thr Gly Gly Gly Leu Val Gln Pro Gly Gly
1               5                   10                  15

Ser Leu Arg Leu Ser Cys Ala Gly Ser Gly Phe Thr Leu Asp Asn Tyr
            20                  25                  30

Ala Val Gly Trp Phe Arg Gln Ala Pro Gly Lys Glu Arg Glu Gly Val
        35                  40                  45

Ser Cys Ile Ser Ser Ser Asp Asp Asn Thr Asp Tyr Ser Asp Ser Val
    50                  55                  60

Lys Gly Arg Phe Thr Ile Ser Arg Asp Asn Ala Lys Asp Thr Val Tyr
65                  70                  75                  80

Leu Gln Met Asn Ser Leu Lys Pro Glu Asp Thr Ala Ile Tyr Tyr Cys
                85                  90                  95

Ala Ala Glu Ser Pro Thr Phe Gly Phe Ser Cys Thr Val Ala Thr Asp
            100                 105                 110

Pro Tyr Asp Tyr Trp Gly Gln Gly Thr Gln Val Thr Val Ser Ser Glu
        115                 120                 125

Pro Lys Thr Pro Lys Pro Gln
    130                 135
```

<210> SEQ ID NO 114
<211> LENGTH: 405
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 114

```
caggtgcagc tggtggagac gggtggaggc ttggtgcagc ctgggggtc tctgagactc      60 tcctgtgcag gctctggatt cactttggat aattatgccg tcggctggtt ccgccaggcc    120
ccagggaagg agcgtgaggg ggtctcatgt attagtagta gtgatgataa cactgactat    180
tcagactccg tgaagggccg attcaccatc tccagagaca acgccaagga cacggtctat    240
ctgcaaatga acagcctgaa acctgaggac acagcgattt attactgtgc agcagaaagc    300
ccgacgttcg ggttcagctg tacggtagcc actgatccat atgactactg gggccagggg    360
acccaggtca ccgtctcctc agaacccaag acaccaaaac cacaa                     405
```

<210> SEQ ID NO 115
<211> LENGTH: 130
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Gly Tyr
            20                  25                  30

Ala Ala Gly Trp Phe Arg Gln Ala Pro Gly Lys Glu Arg Glu Leu Val
        35                  40                  45

Ser Trp Ile Ser Ser Thr Asp Gly Ser Thr Tyr Tyr Ala Ala Ser Val
    50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Thr Ala Gly Leu Gly Leu Asp Val Ser Asp Tyr Val Tyr Asp Tyr Trp
            100                 105                 110

Gly Gln Gly Thr Gln Val Thr Val Ser Ser Glu Pro Lys Thr Pro Lys
        115                 120                 125

Pro Gln
    130
```

<210> SEQ ID NO 116
<211> LENGTH: 390
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 116

```
caggtgcagc tggtggagac gggggggaggc ttggtgcagc ctgggggtc tctgaggctc      60 tcctgtgcag cctctggatt cactttggat ggctatgccg caggctggtt ccgccaggcc    120
ccagggaagg agcgtgagtt ggtctcatgg attagtagca ctgatggtag cacatactat    180
gcagcctccg tgaagggccg attcaccgtc tccagagaca acgccaagaa cacggtgtat    240
ctacaaatga acagcctgaa acctgaggac acagccgttt attactgtac agcaggtcta    300
```

```
gggcttgacg ttagcgacta tgtatatgac tactggggcc aggggaccca ggtcaccgtc    360
tcctcagaac ccaagacacc aaaaccacaa                                     390
```

<210> SEQ ID NO 117
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Gln Val Gln Leu Val Glu Ser Gly Gly Leu Val Gln Pro Gly Gly Ser
1               5                   10                  15

Leu Arg Leu Ser Cys Ala Ala Ser Gly Phe Thr Leu Asp Tyr Tyr Gly
            20                  25                  30

Ile Gly Trp Val Arg Gln Ala Pro Gly Lys Glu Arg Glu Glu Val Ser
        35                  40                  45

Cys Ile Thr Ser Gly Gly Leu Thr Asn Tyr Pro Asp Ser Val Lys Gly
    50                  55                  60

Arg Phe Thr Ile Ser Arg Asp Asn Ala Lys Asn Thr Val Tyr Leu Gln
65                  70                  75                  80

Met Asn Ser Leu Lys Pro Glu Asp Thr Ala Val Tyr Tyr Cys Ala Ile
                85                  90                  95

Asp Arg Val Gly Val Cys Ala Met Glu Asp Phe Gly Ser Trp Gly Gln
            100                 105                 110

Gly Thr Gln Val Thr Val Ser Ser Glu Pro Lys Thr Pro Lys Pro Gln
        115                 120                 125
```

<210> SEQ ID NO 118
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118

```
caggtgcagc tggtggagtc gggcggcttg gtgcagcctg gggggtctct gagactctcc    60
tgtgcagcct ctggattcac tttggattat tatggcatag ctgggtccg ccaggcccca    120 gggaaggagc gtgaggaggt ctcatgtatt actagtggtg gtctcacaaa ctatccagac    180
tccgtgaagg gccgattcac catctccaga gacaacgcca agaacacagt gtatctgcaa    240
atgaacagcc tgaaacctga ggacacggcc gtttattact gtgcaatcga ccgtgtggga    300
gtatgcgcga tggaggactt tggttcctgg ggccagggga cccaggtcac cgtctcctcg    360
gaacccaaga caccaaaacc acaa                                           384
```

<210> SEQ ID NO 119
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

```
Gln Val Gln Leu Val Glu Thr Gly Gly Gly Leu Val Gln Ala Gly Asp
1               5                   10                  15
```

Ser Leu Arg Leu Ser Cys Ala Ala Ser Gly Arg Thr Phe Asn Tyr Tyr
            20                  25                  30

Ala Met Ala Trp Phe Arg Gln Ala Pro Gly Lys Glu Arg Glu Phe Val
        35                  40                  45

Ala Phe Ile Asn Trp Ser Gly Asp Ser Thr Tyr Tyr Ala Gly Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Ser Cys
                85                  90                  95

Ala Ala Glu Phe Gly Thr Phe Ser Tyr Leu Gln Gly Asp Asp Tyr Ser
            100                 105                 110

Tyr Trp Gly Gln Gly Thr Gln Val Thr Val Ser Ser Glu Pro Lys Thr
        115                 120                 125

Pro Lys Pro Gln
    130

<210> SEQ ID NO 120
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 120
caggtgcagc tggtggagac aggtggagga ttggtgcagg ctggggactc tctgagactc      60
tcctgtgcag cctctggacg caccttcaat tactatgcca tggcctggtt ccgccaggcc    120
ccaggaaagg agcgtgaatt tgtagcattt attaactgga gcggcgatag tacatactat    180
gcaggctccg tgaagggccg attcaccatc tccagagaca cgccaagaa cacggtgtat     240 ctgcaaatga acaacctgaa acctgaggac acggccgttt attcctgtgc agcagaattc    300
ggtacatttt cctacttgca aggcgatgac tatagctact ggggccaggg gacccaggtc    360
accgtctcct cagaacccaa gacaccaaaa ccacaa                               396

<210> SEQ ID NO 121
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Phe Ser Ser Tyr
            20                  25                  30

Arg Met Gly Trp Phe Arg Gln Ala Pro Gly Lys Glu Arg Glu Leu Val
        35                  40                  45

Ala Gly Ile Ser Trp Ser Gly Ser Ser Thr Trp Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Asp Gly Leu Gly Thr Asp Trp Ser Asp Ala Ile Trp Asp Tyr

```
                    100                 105                 110
Trp Gly Gln Gly Thr Gln Val Thr Val Ser Ser Glu Pro Lys Thr Pro
        115                 120                 125

Lys Pro Gln
    130
```

<210> SEQ ID NO 122
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122

```
caggtgcagc tggtggagtc tggaggagga ttggtgcagg ctgggggctc tctgagactc      60
tcctgtgcag cctctggacg cagcttcagt agctatcgca tgggctggtt ccgccaggct     120
ccagggaagg agcgtgagct tgtagcaggt attagctgga gtggaagtag tacatggtat     180
gcagactccg tgaagggccg attcaccatc tccagagaca cgccaagaa cacggtgtat      240 ctgcaaatga acagcctgaa acccgaggac acggccgttt attactgtgc agcagatggg     300
ctagggacgg attggagcga tgccatatgg gactactggg gccaggggac ccaggtcacc     360
gtctcctcag aacccaagac accaaaacca caa                                  393
```

<210> SEQ ID NO 123
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Asn Phe Ser His Tyr
            20                  25                  30

Ala Met Gly Trp Phe Arg Gln Ala Pro Gly Lys Ala Arg Glu Phe Val
        35                  40                  45

Ala Thr Ile Asn Arg Asp Gly Asp Ser Thr Tyr Tyr Thr Asn Ser Val
    50                  55                  60

Lys Gly Arg Phe Thr Ile Ser Arg Glu Asn Ala Lys Asn Thr Gly Tyr
65                  70                  75                  80

Leu Gln Met Asn Ser Leu Lys Pro Glu Asp Thr Ala Val Tyr Tyr Cys
                85                  90                  95

Gly Val Gln Tyr Ser Trp Ser Gly Thr Ser Ile Tyr Trp Arg Glu Tyr
            100                 105                 110

Glu Tyr Ala Tyr Trp Gly Gln Gly Ala Gln Val Thr Val Ser Ser Glu
        115                 120                 125

Pro Lys Thr Pro Lys Pro Gln
    130                 135
```

<210> SEQ ID NO 124
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 124

```
caggtgcagc tggtggagtc gggggaggga ttggtgcagg ctgggggctc tctgagactc        60
tcctgtgcag cctctggacg caatttcagt cactatgcca tgggctggtt ccgccaggct       120
ccagggaagg cgcgtgagtt tgtagcaact attaaccggg atggtgatag cacatactat       180
acgaactccg tgaagggccg attcaccatc tccagagaga acgccaagaa cacgggatat       240
ctgcaaatga acagcctgaa acctgaggac acggccgttt attactgtgg agtacaatac       300
tcgtggtcgg gtacaagtat ttactggagg gagtatgagt atgcctactg gggccagggg       360
gcccaggtca ccgtctcctc agaacccaag acaccaaaac cacaa                       405
```

<210> SEQ ID NO 125
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe His Ala Tyr
            20                  25                  30

Tyr Met Ser Trp Val Arg Gln Ala Pro Gly Lys Gly Leu Glu Trp Val
        35                  40                  45

Ser His Ile Gly Asn Gly Gly Ile Ile Thr Arg Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Asn Leu Lys Pro Glu Asp Thr Ala Leu Tyr Tyr Cys
                85                  90                  95

Thr Leu Gly Thr Arg Asp Asp Leu Gly Pro Glu Arg Gly Gln Gly Thr
            100                 105                 110

Gln Val Thr Val Ser Ser Glu Pro Lys Thr Pro Lys Pro Gln
        115                 120                 125
```

<210> SEQ ID NO 126
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

```
caggtgcagc tggtggagtc gggtggaggc ttggtgcagc ctgggggtc tctgagactc         60
tcctgtgcag cctctggatt ccccttccat gcctactaca tgagctgggt ccgccaggct       120
ccaggaaagg ggctcgagtg gtctcccat attggcaatg gtggtattat tacacgctat       180
gcagactccg tgaagggccg gttcaccatc tccagadaca acgccaagaa cacgctgtat       240
ctgcaaatga ccaacctgaa acctgaggac acggccctgt attattgtac cctggggacc       300
cgcgacgacc tggggcctga gaggggccag ggaacccagg tcaccgtctc ctcagaaccc       360
aagacaccaa aaccacaa                                                     378
```

<210> SEQ ID NO 127

<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

```
Gln Val Gln Leu Val Glu Ser Gly Gly Gly Leu Val Gln Pro Gly Gly
1               5                   10                  15
Ser Leu Arg Leu Ser Cys Ala Ala Ser Glu Gly Ile Phe Ser Val Asp
            20                  25                  30
Ala Met Gly Trp Tyr Arg Gln Val Pro Gly Lys Gln Arg Glu Leu Val
        35                  40                  45
Ala Arg Ile Thr Arg Gly Gly Ser Ile Ile Tyr Ala Asp Ser Val Lys
    50                  55                  60
Gly Arg Phe Thr Ile Ser Arg Asp Ser Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Arg Leu Tyr Arg Gly Thr Leu Thr Phe Gly Gln Gly Thr Gln Val Thr
            100                 105                 110
Val Ser Ser Ala His His Ser Glu Asp Pro Ser
        115                 120
```

<210> SEQ ID NO 128
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
caggtgcagc tcgtggagtc gggtggaggc ttggtgcagc ctgggggtc tctgagactc      60
tcctgtgcag cctctgaggg aatcttcagt gttgatgcca tgggctggta ccgccaggtt    120
ccagggaagc agcgcgagtt ggtcgcacga attacccgtg gtggtagcat aatttatgca    180
gactccgtga agggccgatt caccatctcc agagacagcg ccaagaacac ggtgtatctg    240
caaatgaaca gcctgaaacc tgaggacacg gccgtctatt actgtaatcg cctttatagg    300
ggtaccctaa cgttcggcca ggggacccag gtcaccgtct cctcagcgca ccacagcgaa    360
gacccctcg                                                            369
```

<210> SEQ ID NO 129
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Gln Val Gln Leu Val Glu Thr Gly Gly Gly Leu Val Gln Ala Gly Gly
1               5                   10                  15
Ser Leu Arg Leu Ser Cys Ala Ala Ser Gly Arg Thr Phe Ser Ile Tyr
            20                  25                  30
Ala Met Gly Trp Phe Arg Gln Ala Pro Gly Arg Glu Arg Glu Phe Val
        35                  40                  45
Ala Ser Ile Ser Arg Met Gly Trp Ser Thr Tyr Tyr Gly Asp Ser Val
```

| | | | | 50 | | | | | 55 | | | | | 60 | | |

Lys Gly Arg Phe Thr Ala Ser Arg Asp Asn Ala Lys Asn Thr Leu Tyr
65                  70                  75                  80

Leu Gln Met Asn Ser Leu Glu Leu Glu Asp Thr Ala Val Tyr Phe Cys
                85                  90                  95

Ala Ala Ser Ala Ser Ala Leu Arg Val Asn Gln Trp Asp Tyr Trp Gly
            100                 105                 110

Gln Gly Thr Gln Val Thr Val Ser Ser Glu Pro Lys Thr Pro Lys Pro
        115                 120                 125

Gln

<210> SEQ ID NO 130
<211> LENGTH: 387
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130
caggtgcagc tggtggagac cggcggagga ttggtgcagg ctgggggctc tctgagactc      60
tcctgtgcag cctctggacg caccttcagt atctatgcca tgggctggtt ccgccaggct    120
ccagggaggg agcgtgagtt tgtagcgtct attagtcgga tgggttggag cacatattat    180
ggggactccg tgaagggccg attcaccgcc tccagagaca cgccaagaa cacgctgtat     240 ctacaaatga acagcctcga acttgaggac acggccgtat attttttgtgc ggcatctgcg   300 agtgcgttac gagttaatca gtgggactac tggggccagg ggacccaggt caccgtctcc    360
tcagaaccca agacaccaaa accacaa                                         387

<210> SEQ ID NO 131
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Ser Tyr
            20                  25                  30

Ala Ile Gly Trp Phe Arg Gln Ala Pro Gly Lys Glu Arg Glu Gly Val
        35                  40                  45

Ala Cys Ile Ser Ala Ser Gly Ser Gly Thr Asp Tyr Val Asp Ser Val
    50                  55                  60

Lys Gly Arg Phe Thr Val Ser Arg Asp Gln Ala Lys Ser Met Val Phe
65                  70                  75                  80

Leu Gln Met Asn Asn Met Lys Pro Glu Asp Ala Ala Val Tyr Tyr Cys
                85                  90                  95

Ala Ala Asp Tyr Arg Pro Arg Pro Leu Pro Ile Gln Ala Pro Cys Thr
            100                 105                 110

Met Thr Gly Gly Asn Tyr Trp Gly Gln Gly Thr Gln Val Thr Val Ser
        115                 120                 125

Ser Glu Pro Lys Thr Pro Lys Pro Gln Ala Ile Ala Gly Gly Gly Gly
    130                 135                 140

```
Ser Gly Gly Gly Gly Ser Gly Gly Gly Ser Leu Gln Gly Gln Val
145                 150                 155                 160

Gln Leu Val Glu Ser Gly Gly Gly Leu Val Gln Ala Gly Gly Ser Leu
            165                 170                 175

Arg Leu Ser Cys Ala Ala Ser Ile Leu Thr Tyr Asp Leu Asp Tyr Tyr
        180                 185                 190

Tyr Ile Gly Trp Val Arg Gln Ala Pro Gly Lys Glu Arg Glu Gly Val
    195                 200                 205

Ser Cys Ile Ser Ser Thr Asp Gly Ala Thr Tyr Tyr Ala Asp Ser Val
210                 215                 220

Lys Gly Arg Phe Thr Ile Ser Arg Asn Asn Ala Lys Asn Thr Val Tyr
225                 230                 235                 240

Leu Gln Met Asn Asn Leu Lys Pro Glu Asp Thr Ala Ile Tyr Tyr Cys
            245                 250                 255

Ala Ala Ala Pro Leu Ala Gly Arg Tyr Cys Pro Ala Ser His Glu Tyr
        260                 265                 270

Gly Tyr Trp Gly Gln Gly Thr Gln Val Thr Val Ser Ser Ala His His
    275                 280                 285

Ser Glu Asp Pro Ser
    290
```

<210> SEQ ID NO 132
<211> LENGTH: 879
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
caggtgcagc tcgtggagtc aggggaggc ttggtgcagc tggggggtc tctgagactc      60
tcctgtgcag cctctggatt cactttagat agttatgcaa taggctggtt ccgccaggcc    120
ccagggaagg agcgtgaggg ggtcgcatgt attagtgcta gtggtagtgg cacggactat    180
gtagactccg tgaagggccg attcaccgtc tccagagacc aggccaagag catggtgttt    240
ctgcaaatga acaacatgaa acctgaggac gcagccgttt attactgtgc agcagattat    300
cggccgaggc ccctgccgat tcaggcgccg tgtacaatga caggtggcaa ctactgggc     360
caggggaccc aggtcaccgt ctcctcagaa cccaagacac caaaaccaca agcgatcgct    420
ggtggaggcg gttcaggcgg aggtggctct ggcggtggcg gttccctgca gggtcaggtg    480
cagctcgtgg agtccggtgg aggcttggtg caggctgggg gtctctgag actctcctgt    540
gcagcctcta tactcactta tgatttggat tattattaca taggctgggt ccgccaggcc    600
ccagggaagg agcgtgaggg gtctcatgt attagtagta ctgatggtgc acatactat     660
gcagactccg tgaagggccg attcaccatc tccagaaaca acgccaagaa cacggtgtat    720
ctgcaaatga acaacctaaa acctgaggac acagccattt attattgtgc agcagccccc    780
ctggctgggc gctactgtcc cgcctcgcat gagtatggct actggggtca ggggacccag    840
gtcaccgtct cgtcagcgca ccacagcgaa gacccctcg                          879
```

<210> SEQ ID NO 133
<211> LENGTH: 292
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (160)..(160)
<223> OTHER INFORMATION: Any amino acid
<220> FEATURE:
<221> NAME/KEY: MOD_RES
<222> LOCATION: (163)..(163)
<223> OTHER INFORMATION: Any amino acid

<400> SEQUENCE: 133

| Gln | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Leu | Asp | Ser | Tyr |
|---|---|---|---|---|---|---|---|---|---|---|---|---|---|---|---|
| | | | 20 | | | | | 25 | | | | | 30 | | |

| Ala | Ile | Gly | Trp | Phe | Arg | Gln | Ala | Pro | Gly | Lys | Glu | Arg | Glu | Gly | Val |
|---|---|---|---|---|---|---|---|---|---|---|---|---|---|---|---|
| | | 35 | | | | | 40 | | | | | 45 | | | |

| Ala | Cys | Ile | Ser | Ala | Ser | Ser | Gly | Thr | Asp | Tyr | Val | Asp | Ser | Val |
|---|---|---|---|---|---|---|---|---|---|---|---|---|---|---|
| 50 | | | | | 55 | | | | | 60 | | | | |

| Lys | Gly | Arg | Phe | Thr | Val | Ser | Arg | Asp | Gln | Ala | Lys | Ser | Met | Val | Phe |
|---|---|---|---|---|---|---|---|---|---|---|---|---|---|---|---|
| 65 | | | | | 70 | | | | | 75 | | | | | 80 |

| Leu | Gln | Met | Asn | Asn | Met | Lys | Pro | Glu | Asp | Ala | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Ala | Asp | Tyr | Arg | Pro | Arg | Pro | Leu | Pro | Ile | Gln | Ala | Pro | Cys | Thr |
|---|---|---|---|---|---|---|---|---|---|---|---|---|---|---|---|
| | | | 100 | | | | | 105 | | | | | 110 | | |

| Met | Thr | Gly | Gly | Asn | Tyr | Trp | Gly | Gln | Gly | Thr | Gln | Val | Thr | Val | Ser |
|---|---|---|---|---|---|---|---|---|---|---|---|---|---|---|---|
| | | 115 | | | | | 120 | | | | | 125 | | | |

| Ser | Glu | Pro | Lys | Thr | Pro | Lys | Pro | Gln | Ala | Ile | Ala | Gly | Gly | Gly |
|---|---|---|---|---|---|---|---|---|---|---|---|---|---|---|
| 130 | | | | | 135 | | | | | 140 | | | | |

| Ser | Gly | Gly | Gly | Gly | Ser | Gly | Gly | Gly | Ser | Leu | Gln | Gly | Gln | Xaa |
|---|---|---|---|---|---|---|---|---|---|---|---|---|---|---|
| 145 | | | | | 150 | | | | | 155 | | | | 160 |

| Gln | Leu | Xaa | Glu | Ser | Gly | Gly | Gly | Leu | Val | Gln | Ala | Gly | Gly | Ser | Leu |
|---|---|---|---|---|---|---|---|---|---|---|---|---|---|---|---|
| | | | 165 | | | | | 170 | | | | | 175 | | |

| Arg | Leu | Ser | Cys | Ala | Ala | Ser | Glu | Phe | Arg | Ala | Glu | His | Phe | Ala | Val |
|---|---|---|---|---|---|---|---|---|---|---|---|---|---|---|---|
| | | | 180 | | | | | 185 | | | | | 190 | | |

| Gly | Trp | Phe | Arg | Gln | Ala | Pro | Gly | Lys | Glu | Arg | Glu | Gly | Val | Ser | Cys |
|---|---|---|---|---|---|---|---|---|---|---|---|---|---|---|---|
| | | 195 | | | | | 200 | | | | | 205 | | | |

| Val | Asp | Ala | Ser | Gly | Asp | Ser | Thr | Ala | Tyr | Ala | Asp | Ser | Val | Lys | Gly |
|---|---|---|---|---|---|---|---|---|---|---|---|---|---|---|---|
| | 210 | | | | | 215 | | | | | 220 | | | | |

| Arg | Phe | Thr | Ile | Ser | Arg | Asp | Asn | Asn | Lys | Asn | Val | Val | Tyr | Leu | Gln |
|---|---|---|---|---|---|---|---|---|---|---|---|---|---|---|---|
| 225 | | | | | 230 | | | | | 235 | | | | | 240 |

| Met | Asp | Ser | Leu | Glu | Pro | Glu | Asp | Thr | Gly | Asp | Tyr | Tyr | Cys | Gly | Ala |
|---|---|---|---|---|---|---|---|---|---|---|---|---|---|---|---|
| | | | | 245 | | | | | 250 | | | | | 255 | |

| Ser | Tyr | Phe | Thr | Val | Cys | Ala | Lys | Ser | Met | Arg | Lys | Ile | Glu | Tyr | Arg |
|---|---|---|---|---|---|---|---|---|---|---|---|---|---|---|---|
| | | | 260 | | | | | 265 | | | | | 270 | | |

| Tyr | Trp | Gly | Gln | Gly | Thr | Gln | Val | Thr | Val | Ser | Ser | Glu | Pro | Lys | Thr |
|---|---|---|---|---|---|---|---|---|---|---|---|---|---|---|---|
| | | 275 | | | | | 280 | | | | | 285 | | | |

| Pro | Lys | Pro | Gln |
|---|---|---|---|
| | | | 290 |

<210> SEQ ID NO 134
<211> LENGTH: 876
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
caggtgcagc tcgtggagtc agggggaggc ttggtgcagc ctggggggtc tctgagactc      60
tcctgtgcag cctctggatt cactttagat agttatgcaa taggctggtt ccgccaggcc     120
ccagggaagg agcgtgaggg ggtcgcatgt attagtgcta gtggtagtgg cacggactat     180
gtagactccg tgaagggccg attcaccgtc tccagagacc aggccaagag catggtgttt     240
ctgcaaatga acaacatgaa acctgaggac gcagccgttt attactgtgc agcagattat     300
cggccgaggc ccctgccgat tcaggcgccg tgtacaatga caggtggcaa ctactggggc     360
caggggaccc aggtcaccgt ctcctcagaa cccaagacac caaaaccaca agcgatcgct     420
ggtggaggcg gttcaggcgg aggtggctct ggcggtggcg gttccctgca gggtcagktg     480
cagctsgygg agtccggtgg aggcttggtg caggctgggg ggtctctgag actctcctgt     540
gcagcctctg aattccgtgc ggagcatttt gccgtgggct ggttccgcca ggccccaggg     600
aaggagcgtg agggggtctc atgtgtagac gcgagtggtg atagtacagc atatgcggac     660
tctgtgaagg gccgattcac catctcccaga gacaacaaca agaacgtagt gtatctgcaa     720
atggacagcc tggaacctga agacacagga gattattatt gtggagcctc gtactttact     780
gtctgcgcca agagcatgcg gaaaattgaa tataggtact ggggccaggg gacccaggtc     840
accgtctcct cagaacccaa gacaccaaaa ccacaa                                876

<210> SEQ ID NO 135
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Gln Val Gln Leu Val Glu Ser Gly Gly Gly Leu Val Gln Ala Gly Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
        35                  40                  45

Gly Val Ser Cys Ile Ser Ser Thr Asp Gly Ala Thr Tyr Tyr Ala Asp
    50                  55                  60

Ser Val Lys Gly Arg Phe Thr Ile Ser Arg Asn Asn Ala Lys Asn Thr
65                  70                  75                  80

Val Tyr Leu Gln Met Asn Asn Leu Lys Pro Glu Asp Thr Ala Ile Tyr
                85                  90                  95

Tyr Cys Ala Ala Ala Pro Leu Ala Gly Arg Tyr Cys Pro Ala Ser His
            100                 105                 110

Glu Tyr Gly Tyr Trp Gly Gln Gly Thr Gln Val Thr Val Ser Ser Ala
        115                 120                 125

His His Ser Glu Asp Pro Ser Ala Ile Ala Gly Gly Gly Ser Gly
    130                 135                 140

Gly Gly Gly Ser Gly Gly Gly Ser Leu Gln Gly Gln Val Gln Leu
145                 150                 155                 160

Val Glu Ser Gly Gly Gly Leu Val Gln Pro Gly Gly Ser Leu Arg Leu
                165                 170                 175

Ser Cys Glu Ala Ser Gly Phe His Leu Glu His Phe Ala Val Gly Trp
            180                 185                 190

Phe Arg Gln Ala Pro Gly Lys Glu Arg Glu Gly Val Ser Cys Ile Ser
        195                 200                 205
```

Ala Ser Gly Asp Ser Thr Thr Tyr Ala Asp Ser Val Lys Gly Arg Ser
    210                 215                 220

Thr Ile Ser Lys Asp Asn Ala Lys Asn Ala Val Tyr Leu Gln Met Asp
225                 230                 235                 240

Ser Leu Arg Pro Glu Asp Thr Gly Asp Tyr Tyr Cys Ala Ala Ser His
                245                 250                 255

Phe Ser Val Cys Gly Lys Asn Ile Arg Lys Ile Glu Tyr Arg Tyr Trp
            260                 265                 270

Gly Gln Gly Thr Pro Val Thr Val Ser Ser Glu Pro Lys Thr Pro Lys
        275                 280                 285

Pro Gln
    290

<210> SEQ ID NO 136
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 136
caggtgcagc tggtggagtc cggtggaggc ttggtgcagg ctgggggtc tctgagactc      60 tcctgtgcag cctctatact cacttatgat ttggattatt attacatagg ctgggtccgc     120
caggccccag ggaaggagcg tgagggggtc tcatgtatta gtagtactga tggtgccaca     180
tactatgcag actccgtgaa gggccgattc accatctcca gaacaacgc caagaacacg      240 gtgtatctgc aaatgaacaa cctaaaacct gaggacacag ccatttatta ttgtgcagca     300 gccccccctgg ctgggcgcta ctgtcccgcc tcgcatgagt atggctactg ggtcagggg    360 acccaggtca ccgtctcgtc agcgcaccac agcgaagacc cctcggcgat cgctggtgga    420
ggcggttcag gcgaggtgg ctctggcggt ggcggttccc tgcagggtca ggtgcagctg      480
gtggagtctg gtggaggctt ggtgcagcct gggggtctc tgagactctc ctgtgaagcc     540
tcaggattcc atttggagca ttttgccgta ggctggttcc gccaggcccc agggaaggag    600
cgtgaggggg tctcatgtat aagcgcgagt ggtgatagta caacgtatgc agactccgtg    660
aagggccgat ccaccatctc caagacaac gccaagaacg cggtgtatct gcaaatggac     720
agcctgagac ccgaggacac aggcgattat tactgtgcag cctcgcactt cagtgtctgc    780
ggcaagaaca ttcggaaaat tgagtatagg tactggggcc aggggacccc ggtcaccgtc    840
tcctcagaac ccaagacacc aaaaccacaa                                      870

<210> SEQ ID NO 137
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Val Glu Ser Gly Gly Gly Leu Val Gln Ala Gly Gly
1               5                   10                  15

Ser Leu Arg Leu Ser Cys Ala Ala Ser Ile Leu Thr Tyr Asp Leu Asp
            20                  25                  30

Tyr Tyr Tyr Ile Gly Trp Val Arg Gln Ala Pro Gly Lys Glu Arg Glu
        35                  40                  45

Gly Val Ser Cys Ile Ser Ser Thr Asp Gly Ala Thr Tyr Tyr Ala Asp
        50                  55                  60

Ser Val Lys Gly Arg Phe Thr Ile Ser Arg Asn Asn Ala Lys Asn Thr
 65                  70                  75                  80

Val Tyr Leu Gln Met Asn Asn Leu Lys Pro Glu Asp Thr Ala Ile Tyr
                 85                  90                  95

Tyr Cys Ala Ala Ala Pro Leu Ala Gly Arg Tyr Cys Pro Ala Ser His
            100                 105                 110

Glu Tyr Gly Tyr Trp Gly Gln Gly Thr Gln Val Thr Val Ser Ser Ala
        115                 120                 125

His His Ser Glu Asp Pro Ser Ala Ile Ala Gly Gly Gly Gly Ser Gly
    130                 135                 140

Gly Gly Gly Ser Gly Gly Gly Gly Ser Leu Gln Gly Gln Val Gln Leu
145                 150                 155                 160

Ala Glu Ser Gly Gly Gly Leu Val Gln Ala Gly Gly Ser Leu Arg Leu
                165                 170                 175

Ser Cys Ala Ala Ser Glu Phe Arg Ala Glu His Phe Ala Val Gly Trp
            180                 185                 190

Phe Arg Gln Ala Pro Gly Lys Glu Arg Glu Gly Val Ser Cys Val Asp
        195                 200                 205

Ala Ser Gly Asp Ser Thr Ala Tyr Ala Asp Ser Val Lys Gly Arg Phe
    210                 215                 220

Thr Ile Ser Arg Asp Asn Asn Lys Asn Val Val Tyr Leu Gln Met Asp
225                 230                 235                 240

Ser Leu Glu Pro Glu Asp Thr Gly Asp Tyr Tyr Cys Gly Ala Ser Tyr
                245                 250                 255

Phe Thr Val Cys Ala Lys Ser Met Arg Lys Ile Glu Tyr Arg Tyr Trp
            260                 265                 270

Gly Gln Gly Thr Gln Val Thr Val Ser Ser Glu Pro Lys Thr Pro Lys
        275                 280                 285

Pro Gln
    290

<210> SEQ ID NO 138
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 138
caggtgcagc tggtggagtc cggtggaggc ttggtgcagg ctgggggtc tctgagactc      60 tcctgtgcag cctctatact cacttatgat ttggattatt attacatagg ctgggtccgc    120
caggccccag ggaaggagcg tgaggggtc tcatgtatta gtagtactga tggtgccaca    180
tactatgcag actccgtgaa gggccgattc accatctcca gaaacaacgc caagaacacg    240
gtgtatctgc aaatgaacaa cctaaaacct gaggacacag ccatttatta ttgtgcagca    300 gccccctgg ctgggcgcta ctgtcccgcc tcgcatgagt atggctactg ggtcagggg    360 acccaggtca ccgtctcgtc agcgcaccac agcgaagacc cctcggcgat cgctggtgga    420
ggcggttcag gcggaggtgg ctctggcggt ggcggttccc tgcagggtca ggtgcagctg    480
gcggagtccg gtgaggcctt ggtgcaggct gggggtctc tgagactctc ctgtgcagcc    540
tctgaattcc gtgcggagca ttttgccgtg ggctggttcc gccaggcccc agggaaggag    600

```
cgtgaggggg tctcatgtgt agacgcgagt ggtgatagta cagcatatgc ggactctgtg    660
aagggccgat tcaccatctc cagagacaac aacaagaacg tagtgtatct gcaaatggac    720
agcctggaac ctgaagacac aggagattat tattgtggag cctcgtactt tactgtctgc    780
gccaagagca tgcggaaaat tgaatatagg tactggggcc aggggaccca ggtcaccgtc    840
tcctcagaac ccaagacacc aaaaccacaa                                     870
```

<210> SEQ ID NO 139
<211> LENGTH: 284
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 139

```
Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Ser Tyr Ala Met Gly
            20                  25                  30

Trp Phe Arg Gln Gly Pro Gly Lys Glu Arg Glu Phe Val Ala Thr Ile
        35                  40                  45

Ser Trp Ser Ser Thr Asn Thr Trp Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Cys Ala Ala Ser
                85                  90                  95

His Arg Phe Ser Asp Tyr Pro Met Arg Ser Glu Asp Gly Met Asp Tyr
            100                 105                 110

Trp Gly Lys Gly Thr Leu Val Thr Val Ser Ser Glu Pro Lys Thr Pro
        115                 120                 125

Lys Pro Gln Ala Ile Ala Gly Gly Gly Ser Gly Gly Gly Gly Ser
    130                 135                 140

Gly Gly Gly Gly Ser Leu Gln Gly Gln Val Gln Leu Val Glu Thr Gly
145                 150                 155                 160

Gly Gly Leu Val Gln Ala Gly Gly Ser Leu Arg Leu Ser Cys Ala Ala
                165                 170                 175

Ser Gly Arg Thr Phe Ser Ser Tyr Ser Met Gly Trp Phe Arg Gln Ala
            180                 185                 190

Pro Gly Lys Glu Arg Glu Tyr Val Ala Ala Val Asn Ser Asn Gly Asp
        195                 200                 205

Ser Thr Phe Tyr Ala Asp Ser Ile Lys Gly Arg Phe Thr Val Ser Arg
    210                 215                 220

Asp Ala Ala Lys Asn Thr Val Tyr Leu Gln Met Asn Ser Leu Lys Pro
225                 230                 235                 240

Glu Asp Thr Ala Leu Tyr Tyr Cys Ala Ala Val Tyr Gly Arg Tyr Thr
                245                 250                 255

Tyr Gln Ser Pro Lys Ser Tyr Glu Tyr Trp Gly Gln Gly Thr Gln Val
            260                 265                 270

Thr Val Ser Ser Glu Pro Lys Thr Pro Lys Pro Gln
        275                 280
```

<210> SEQ ID NO 140
<211> LENGTH: 852

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 140

```
caggtgcagc tggtggagac ggggggagga ttggtgcagg ctgggggctc tctgagactc      60
tcctgtgcag cctctggacg cagttatgcc atgggctggt tccgccaggg tccaggaag     120
gagcgtgagt ttgtagccac tatcagttgg agtagtacta acacatggta tgcagattcc    180
gtgaagggcc gattcaccat ctctagagac aacgccaaga acacggtgta tctgcaaatg    240
aacagcctga acctgagga cacggctgtt tattactgtg cagcgagcca tcgttttagc    300
gactatccca tgaggtcaga ggacggcatg gactactggg gcaaagggac cctggtcacc    360
gtctcctcag aacccaagac accaaaacca caagcgatcg ctggtggagg cggttcaggc    420
ggaggtggct ctggcggtgg cggttccctg caggtcagg tgcagctggt ggagacggga    480
ggaggattgg tgcaggctgg gggctctctg agactctcgt gtgcagcctc tggacgcacc    540
ttcagtagct attccatggg ctggttccgc caggctccag ggaaggagcg tgagtatgta    600
gcagcagtta actccaatgg cgacagtaca ttctatgccg actccattaa gggccgattc    660
accgtctcca gagacgccgc caagaacaca gtctatctgc aaatgaacag cctgaaacct    720
gaggacacgg ccctttatta ctgtgcagct gtctacggta gatacactta ccagtcccca    780
aaatcgtatg agtactgggg ccaggggacc caggtcaccg tctcctcaga acccaagaca    840
ccaaaaccac aa                                                       852
```

<210> SEQ ID NO 141
<211> LENGTH: 289
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

```
Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Ser Tyr Ala Met Gly
            20                  25                  30

Trp Phe Arg Gln Gly Pro Gly Lys Glu Arg Glu Phe Val Ala Thr Ile
        35                  40                  45

Ser Trp Ser Ser Thr Asn Thr Trp Tyr Ala Asp Ser Val Lys Gly Arg
    50                  55                  60

Phe Thr Ile Ser Arg Asp Asn Ala Lys Asn Thr Val Tyr Leu Gln Met
65                  70                  75                  80

Asn Ser Leu Lys Pro Glu Asp Thr Ala Val Tyr Tyr Cys Ala Ala Ser
                85                  90                  95

His Arg Phe Ser Asp Tyr Pro Met Arg Ser Glu Asp Gly Met Asp Tyr
            100                 105                 110

Trp Gly Lys Gly Thr Leu Val Thr Val Ser Ser Glu Pro Lys Thr Pro
        115                 120                 125

Lys Pro Gln Ala Ile Ala Gly Gly Gly Ser Gly Gly Gly Gly Ser
    130                 135                 140

Gly Gly Gly Gly Ser Leu Gln Gly Gln Val Gln Leu Val Glu Thr Gly
145                 150                 155                 160
```

Gly Gly Leu Val Lys Pro Gly Gly Ser Leu Arg Leu Ser Cys Val Val
            165                 170                 175

Ser Gly Phe Thr Phe Asp Asp Tyr Arg Met Ala Trp Val Arg Gln Ala
        180                 185                 190

Pro Gly Lys Glu Leu Glu Trp Val Ser Ser Ile Asp Ser Trp Ser Ile
        195                 200                 205

Asn Thr Tyr Tyr Glu Asp Ser Val Lys Gly Arg Phe Thr Ile Ser Thr
    210                 215                 220

Asp Asn Ala Lys Asn Thr Leu Tyr Leu Gln Met Ser Ser Leu Lys Pro
225                 230                 235                 240

Glu Asp Thr Ala Val Tyr Tyr Cys Ala Ala Glu Asp Arg Leu Gly Val
                245                 250                 255

Pro Thr Ile Asn Ala His Pro Ser Lys Tyr Asp Tyr Asn Tyr Trp Gly
            260                 265                 270

Gln Gly Thr Gln Val Thr Val Ser Ser Glu Pro Lys Thr Pro Lys Pro
        275                 280                 285

Gln

<210> SEQ ID NO 142
<211> LENGTH: 867
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 142
caggtgcagc tggtggagac ggggggagga ttggtgcagg ctgggggctc tctgagactc      60
tcctgtgcag cctctggacg cagttatgcc atgggctggt tccgccaggg tccaggaag      120 gagcgtgagt ttgtagccac tatcagttgg agtagtacta cacatggta tgcagattcc      180 gtgaagggcc gattcaccat ctctagagac aacgccaaga acacggtgta tctgcaaatg      240
aacagcctga aacctgagga cacggctgtt tattactgtg cagcgagcca tcgttttagc      300
gactatccca tgaggtcaga ggacggcatg gactactggg gcaaaggac cctggtcacc      360 gtctcctcag aacccaagac accaaaacca caagcgatcg ctggtggagg cggttcaggc      420
ggaggtggct ctggcggtgg cggttccctg cagggtcagg tgcagctggt ggagactggt      480
ggaggcttgg tgaagcctgg ggttctctg agactctcct gtgtagtctc cggattcact      540
tttgatgatt atcgcatggc ttgggtccgc caggctccag ggaaggagct ggagtgggtg      600
tccagtatag atagttggag tatcaacaca tactatgaag actccgtgaa gggccggttc      660
accatctcca cagacaacgc caagaataca ctgtatctgc aaatgagcag cctgaaacct      720
gaggacacgg ccgtgtatta ctgtgcagca gaggaccgct taggtgtacc gactattaac      780 gcccacctt caaaatatga ttataactac tggggggcagg gacccaggt caccgtctcc      840 tcagaaccca agacaccaaa accacaa                                           867

<210> SEQ ID NO 143
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Leu Gln Leu Val Glu Thr Gly Gly Gly Leu Val Lys Pro Gly Gly

|   | 1 |   |   |   | 5 |   |   |   |   | 10 |   |   |   |   | 15 |
|---|---|---|---|---|---|---|---|---|---|---|---|---|---|---|---|
| Ser | Leu | Arg | Leu | Ser | Cys | Val | Val | Ser | Gly | Phe | Thr | Phe | Asp | Asp | Tyr |

Arg Met Ala Trp Val Arg Gln Ala Pro Gly Lys Glu Leu Glu Trp Val
 35                  40                   45

Ser Ser Ile Asp Ser Trp Ser Ile Asn Thr Tyr Tyr Glu Asp Ser Val
50                   55                   60

Lys Gly Arg Phe Thr Ile Ser Thr Asp Asn Ala Lys Asn Thr Leu Tyr
65                   70                   75                   80

Leu Gln Met Ser Ser Leu Lys Pro Glu Asp Thr Ala Val Tyr Tyr Cys
              85                   90                   95

Ala Ala Glu Asp Arg Leu Gly Val Pro Thr Ile Asn Ala His Pro Ser
             100                  105                  110

Lys Tyr Asp Tyr Asn Tyr Trp Gly Gln Gly Thr Gln Val Thr Val Ser
         115                  120                  125

Ser Glu Pro Lys Thr Pro Lys Pro Gln Ala Ile Ala Gly Gly Gly Gly
     130                  135                  140

Ser Gly Gly Gly Gly Ser Gly Gly Gly Ser Leu Gln Gly Gln Val
145                  150                  155                  160

Gln Leu Val Glu Thr Gly Gly Gly Leu Val Gln Ala Gly Gly Ser Leu
                 165                  170                  175

Arg Leu Ser Cys Ala Ala Ser Gly Arg Thr Phe Ser Tyr Ser Met
             180                  185                  190

Gly Trp Phe Arg Gln Ala Pro Gly Lys Glu Arg Glu Tyr Val Ala Ala
         195                  200                  205

Val Asn Ser Asn Gly Asp Ser Thr Phe Tyr Ala Asp Ser Ile Lys Gly
     210                  215                  220

Arg Phe Thr Val Ser Arg Asp Ala Ala Lys Asn Thr Val Tyr Leu Gln
225                  230                  235                  240

Met Asn Ser Leu Lys Pro Glu Asp Thr Ala Leu Tyr Tyr Cys Ala Ala
                 245                  250                  255

Val Tyr Gly Arg Tyr Thr Tyr Gln Ser Pro Lys Ser Tyr Glu Tyr Trp
             260                  265                  270

Gly Gln Gly Thr Gln Val Thr Val Ser Ser Glu Pro Lys Thr Pro Lys
         275                  280                  285

Pro Gln
    290

<210> SEQ ID NO 144
<211> LENGTH: 870
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
cagttgcagc tcgtggagac tggtggaggc ttggtgaagc tggggggttc tctgagactc       60
tcctgtgtag tctccggatt cacttttgat gattatcgca tggcttgggt ccgccaggct      120
ccagggaagg agctggagtg ggtgtccagt atagatagtt ggagtatcaa cacatactat      180
gaagactccg tgaagggccg gttcaccatc tccacagaca acgccaagaa tacactgtat      240
ctgcaaatga gcagcctgaa acctgaggac acggccgtgt attactgtgc agcagaggac      300
cgcttaggtg taccgactat taacgcccac ccttcaaaat atgattataa ctactggggg      360

```
cagggggaccc aggtcaccgt ctcctcagaa cccaagacac caaaaccaca agcgatcgct    420
ggtggaggcg gttcaggcgg aggtggctct ggcggtggcg gttccctgca gggtcaggtg    480
cagctggtgg agacgggagg aggattggtg caggctgggg gctctctgag actctcgtgt    540
gcagcctctg gacgcacctt cagtagctat ccatgggct ggttccgcca ggctccaggg     600
aaggagcgtg agtatgtagc agcagttaac tccaatggcg acagtacatt ctatgccgac    660
tccattaagg gccgattcac cgtctccaga gacgccgcca agaacacagt ctatctgcaa    720
atgaacagcc tgaaacctga ggacacggcc ctttattact gtgcagctgt ctacggtaga    780
tacacttacc agtccccaaa atcgtatgag tactggggcc aggggaccca ggtcaccgtc    840
tcctcagaac ccaagacacc aaaaccacaa                                     870
```

<210> SEQ ID NO 145
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Gly Ser Gly Gly Gly Gly Ser Gly Gly Gly Gly Ser
1               5                   10                  15

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Asp Ile Cys Leu Pro Arg Trp Gly Cys Leu Trp Glu Asp
1               5                   10

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Gly Gly Ser
1               5

<210> SEQ ID NO 148
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Ser Gly Gly Gly Leu Val Gln Pro Gly Gly Ser Leu Arg Leu Ser Cys
1               5                   10                  15

Ala Ala Ser Gly Ser Ser Phe Ser Arg Tyr Ala Met Arg Trp Tyr Arg
                20                  25                  30

Gln Ala Pro Gly Lys Gln Arg Glu Leu Val Ala Asn Ile Asn Ser Arg
            35                  40                  45

```
Gly Thr Ser Asn Tyr Ala Asp Ser Val Lys Gly Arg Phe Thr Ile Ser
            50                  55                  60

Arg Asp Asn Ala Lys Asn Thr Val Tyr Leu Gln Met Asn Ser Leu Lys
 65                  70                  75                  80

Pro Glu Asp Thr Ala Val Tyr Tyr Cys Asn Ala Glu Trp Leu Gly Arg
                85                  90                  95

Ser Glu Pro Ser Trp Gly Gln Gly Thr Gln Val Thr Val Ser Ser
                100                 105                 110

<210> SEQ ID NO 149
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Ser Gly Gly Gly Leu Val Gln Pro Gly Gly Ser Leu Arg Leu Ser Cys
 1               5                  10                  15

Ala Ala Ser Gly Phe Ile Phe Ser Leu Tyr Thr Met Arg Trp His Arg
                20                  25                  30

Gln Ala Pro Gly Lys Glu Arg Glu Leu Val Ala Thr Ile Thr Ser Ala
                35                  40                  45

Thr Gly Ile Thr Asn Tyr Ala Asp Ser Val Lys Gly Arg Phe Ile Ile
            50                  55                  60

Ser Arg Asp Asp Ala Lys Lys Thr Gly Tyr Leu Gln Met Asn Ser Leu
 65                  70                  75                  80

Lys Pro Glu Asp Thr Ala Val Tyr Tyr Cys Asn Ala Val Arg Thr Thr
                85                  90                  95

Val Ser Arg Asp Tyr Trp Gly Gln Gly Thr Gln Val Thr Val Ser Ser
                100                 105                 110

<210> SEQ ID NO 150
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Ser Gly Gly Gly Leu Val Gln Pro Gly Gly Ser Leu Arg Leu Ser Cys
 1               5                  10                  15

Ala Ala Ser Gly Ile Ile Phe Ser Ile Tyr Thr Met Gly Trp Tyr Arg
                20                  25                  30

Gln Ala Pro Gly Lys Gln Arg Glu Leu Val Ala Ala Ile Pro Ser Gly
                35                  40                  45

Pro Ser Ala Asn Ala Thr Asp Ser Val Gly Gly Arg Phe Thr Ile Thr
            50                  55                  60

Arg Asp Asn Ala Glu Asn Thr Val Tyr Leu Gln Met Asn Asp Leu Lys
 65                  70                  75                  80

Pro Glu Asp Thr Ala Val Tyr Tyr Cys Asn Ala Arg Arg Gly Pro Gly
                85                  90                  95

Ile Lys Asn Tyr Trp Gly Gln Gly Thr Gln Val Thr Val Ser Ser
                100                 105                 110

<210> SEQ ID NO 151
```

<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Ser Gly Gly Gly Leu Val Gln Pro Gly Gly Ser Leu Ser Val Ser Cys
1               5                   10                  15

Ala Ala Ser Gly Ser Ile Ala Arg Pro Gly Ala Met Ala Trp Tyr Arg
            20                  25                  30

Gln Ala Pro Gly Lys Glu Arg Glu Leu Val Ala Ser Ile Thr Pro Gly
        35                  40                  45

Gly Leu Thr Asn Tyr Ala Asp Ser Val Thr Gly Arg Phe Thr Ile Ser
    50                  55                  60

Arg Asp Asn Ala Lys Arg Thr Val Tyr Leu Gln Met Asn Ser Leu Gln
65                  70                  75                  80

Pro Glu Asp Thr Ala Val Tyr Tyr Cys His Ala Arg Ile Ile Pro Leu
                85                  90                  95

Gly Leu Gly Ser Glu Tyr Arg Asp His Trp Gly Gln Gly Thr Gln Val
            100                 105                 110

Thr Val Ser Ser
        115

<210> SEQ ID NO 152
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Thr Gly Gly Leu Val Gln Pro Gly Gly Ser Leu Arg Leu Ser Cys Ala
1               5                   10                  15

Ala Ser Gly Leu Thr Phe Ser Ser Thr Ala Met Ala Trp Phe Arg Gln
            20                  25                  30

Ala Pro Gly Lys Glu Arg Glu Phe Val Ala Arg Ile Ser Gly Ala Gly
        35                  40                  45

Ile Thr Ile Tyr Tyr Ser Asp Ser Val Lys Asp Arg Phe Thr Ile Ser
    50                  55                  60

Arg Asn Asn Val Glu Asn Thr Val Tyr Leu Gln Met Asn Ser Leu Lys
65                  70                  75                  80

Thr Glu Asp Thr Ala Val Tyr Tyr Cys Ala Ala Arg Arg Asn Thr Tyr
                85                  90                  95

Thr Ser Asp Tyr Asn Ile Pro Ala Arg Tyr Pro Tyr Trp Gly Gln Gly
            100                 105                 110

Thr Gln Val Thr Val Ser Ser
        115

<210> SEQ ID NO 153
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Thr Gly Gly Leu Val Gln Pro Gly Gly Ser Leu Arg Leu Ser Cys Ala
1               5                   10                  15

Ala Ser Arg Ser Thr Thr Ala Thr Ile Tyr Ser Met Asn Trp Tyr Arg
            20                  25                  30

Gln Ala Pro Gly Lys Gln Arg Glu Leu Val Ala Gly Met Thr Ser Asp
            35                  40                  45

Gly Gln Thr Asn Tyr Ala Thr Ser Val Lys Gly Arg Phe Thr Ile Ser
        50                  55                  60

Arg Asp Asn Ala Lys Asn Thr Val Tyr Leu Ile Met Asn Ser Leu Lys
65                  70                  75                  80

Leu Glu Asp Thr Ala Val Tyr Tyr Cys Tyr Val Lys Pro Trp Arg Leu
                85                  90                  95

Gln Gly Trp Asp Tyr Trp Gly Gln Gly Thr Gln Val Thr Val Ser Ser
            100                 105                 110

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Ser Gly Gly Gly Leu Val Gln Pro Gly Gly Ser Leu Arg Leu Ser Cys
1               5                   10                  15

Ala Ala Pro Glu Ser Ile Val Asn Ser Arg Thr Met Ala Trp Tyr Arg
            20                  25                  30

Gln Ala Pro Gly Lys Gln Arg Glu Arg Val Ala Thr Ile Thr Thr Ala
            35                  40                  45

Gly Ser Pro Asn Tyr Ala Asp Ser Val Lys Gly Arg Phe Ala Ile Ser
        50                  55                  60

Arg Asp Asn Ala Lys Asn Thr Val Tyr Leu Gln Met Asn Ser Leu Lys
65                  70                  75                  80

Pro Glu Asp Thr Ala Val Tyr Tyr Cys Asn Thr Leu Leu Ser Thr Leu
                85                  90                  95

Pro Tyr Gly Gln Gly Thr Gln Val Thr Val Ser Ser
            100                 105

<210> SEQ ID NO 155
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Ser Gly Gly Gly Leu Val Gln Pro Gly Gly Ser Leu Gly Leu Ser Cys
1               5                   10                  15

Val Val Ala Ser Glu Arg Ser Ile Asn Asn Tyr Gly Met Gly Trp Tyr
            20                  25                  30

Arg Gln Ala Pro Gly Lys Gln Arg Glu Leu Val Ala Gln Ile Ser Ser
            35                  40                  45

Gly Gly Thr Thr Asn Tyr Ala Asp Ser Val Glu Gly Arg Phe Thr Ile
        50                  55                  60

Ser Arg Asp Asn Val Lys Lys Met Val His Leu Gln Val Asn Ser Leu
65                  70                  75                  80

Lys Pro Glu Asp Thr Ala Val Tyr Tyr Cys Asn Ser Leu Leu Arg Thr
                85                  90                  95

Phe Ser Trp Gly Gln Gly Thr Gln Val Thr Val Ser Ser
            100                 105

<210> SEQ ID NO 156
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Thr Gly Gly Gly Leu Val Gln Pro Gly Gly Ser Leu Arg Leu Ser Cys
1               5                   10                  15

Ala Ala Ser Gly Phe Thr Phe Ser Ser Tyr Arg Met Ser Trp Tyr Arg
            20                  25                  30

Gln Ala Ala Gly Lys Glu Arg Asp Val Val Ala Thr Ile Thr Ala Asn
        35                  40                  45

Gly Val Pro Thr Gly Tyr Ala Asp Ser Val Met Gly Arg Phe Thr Ile
    50                  55                  60

Ser Arg Asp Asn Ala Lys Asn Thr Val Tyr Leu Glu Met Asn Ser Leu
65                  70                  75                  80

Asn Pro Glu Asp Thr Ala Val Tyr Tyr Cys Asn Ala Pro Arg Leu His
                85                  90                  95

Thr Ser Val Gly Tyr Trp Gly Gln Gly Thr Gln Val Thr Val Ser Ser
            100                 105                 110

<210> SEQ ID NO 157
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ser Gly Gly Gly Leu Val Gln Ala Gly Asn Ser Leu Arg Leu Ser Cys
1               5                   10                  15

Thr Ala Ser Gly Val Ile Phe Ser Ile Tyr Thr Met Gly Trp Phe Arg
            20                  25                  30

Gln Ala Pro Gly Lys Glu Arg Glu Phe Val Ala Ala Ile Gly Val Ala
        35                  40                  45

Asp Gly Thr Ala Leu Val Ala Asp Ser Val Thr Gly Arg Phe Thr Ile
    50                  55                  60

Ser Arg Asp Asn Ala Lys Asn Thr Val Tyr Leu His Met Asn Ser Leu
65                  70                  75                  80

Lys Pro Glu Asp Thr Ala Val Tyr Ser Cys Ala Ala Tyr Leu Ser Pro
                85                  90                  95

Arg Val Gln Ser Pro Tyr Ile Thr Asp Ser Arg Tyr Gly Leu Trp Gly
            100                 105                 110

Gln Gly Thr Gln Val Thr Val Ser Ser
        115                 120

<210> SEQ ID NO 158
<211> LENGTH: 111
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 158

Thr Gly Gly Gly Leu Val Gln Ala Gly Gly Ser Leu Arg Leu Ser Cys
1               5                   10                  15

Ala Ala Ser Gly Arg Tyr Ala Met Gly Trp Phe Arg Gln Ala Pro Gly
            20                  25                  30

Lys Glu Arg Glu Phe Val Ala Thr Ile Ser Arg Ser Gly Ala Ile Arg
        35                  40                  45

Glu Tyr Ala Asp Ser Val Lys Gly Arg Phe Thr Ile Ser Arg Asp Gly
50                  55                  60

Ala Glu Asn Thr Val Tyr Leu Glu Met Asn Ser Leu Lys Pro Asp Asp
65                  70                  75                  80

Thr Ala Ile Tyr Val Cys Ala Glu Gly Arg Gly Ala Thr Phe Asn Pro
                85                  90                  95

Glu Tyr Ala Tyr Trp Gly Gln Gly Thr Gln Val Thr Val Ser Ser
            100                 105                 110

<210> SEQ ID NO 159
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Thr Gly Gly Gly Leu Val Gln Ala Gly Gly Ser Leu Arg Leu Ser Cys
1               5                   10                  15

Ser Ala Ser Gly Leu Thr Phe Gly Asn Tyr Ala Met Gly Trp Phe Arg
            20                  25                  30

Gln Ala Pro Gly Lys Glu Arg Glu Phe Val Ala Ser Ile Ser Arg Ser
        35                  40                  45

Gly Ser Asn Thr Trp Tyr Ala Glu Pro Leu Lys Gly Arg Phe Ala Ile
    50                  55                  60

Ser Arg Asp Asn Asp Lys Asn Ala Leu Tyr Leu Gln Met Asn Ser Leu
65                  70                  75                  80

Lys Pro Glu Asp Thr Ala Val Tyr Tyr Cys Ala Gly Gly Ser Tyr Asn
                85                  90                  95

Ser Asp Trp Trp Asn Tyr Met Tyr Trp Gly Gln Gly Thr Gln Val Thr
            100                 105                 110

Val Ser Ser
        115

<210> SEQ ID NO 160
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Gly Gly Gly Gly Leu Val Gln Ala Gly Gly Ser Leu Arg Leu Ser
1               5                   10                  15

Cys Ala Ala Ser Gly Arg Thr Phe Ser Gly Tyr Ala Met Gly Trp Phe
            20                  25                  30

Arg Gln Ala Pro Gly Lys Glu Arg Glu Phe Val Ala Asp Ile Ser Trp

```
                    35                  40                  45
Ser Gly His Asn Thr Tyr Tyr Gly Asp Ser Val Lys Gly Arg Phe Thr
 50                  55                  60

Ile Ser Arg Asp Thr Ala Lys Asn Thr Val Tyr Leu Gln Met Asn Ser
 65                  70                  75                  80

Leu Lys Pro Glu Asp Thr Ala Val Tyr Tyr Cys Ala Ala Glu Gly Ala
                 85                  90                  95

Arg Thr His Leu Ser Asp Ser Tyr Tyr Phe Pro Gly Leu Trp Ala Glu
                100                 105                 110

Pro Pro Val Gly Tyr Trp Gly Gln Gly Thr Gln Val Thr Val Ser Ser
                115                 120                 125

<210> SEQ ID NO 161
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Thr Gly Gly Gly Leu Val Gln Ala Gly Gly Thr Leu Arg Leu Ser Cys
 1               5                  10                  15

Ala Ala Ser Gly Arg Thr Phe Thr Ser Tyr Tyr Ile Gly Trp Phe Arg
                 20                  25                  30

Gln Glu Pro Gly Lys Glu Arg Glu Phe Val Ala Ser Ile Gly Trp Thr
                 35                  40                  45

Asp Asp Asn Thr Tyr Tyr Ala Asp Ser Val Lys Gly Arg Phe Thr Ile
                 50                  55                  60

Ser Arg Asp Asn Ala Glu Thr Thr Ala Tyr Leu Gln Met Ser Gly Leu
 65                  70                  75                  80

Lys Pro Glu Asp Thr Ala Val Tyr Tyr Cys Ala Ala Asp Tyr Gly Ser
                 85                  90                  95

Gly Ile Arg Ala Trp Tyr Asn Trp Ile Tyr Trp Gly Gln Gly Thr Gln
                100                 105                 110

Val Thr Val Ser Ser
        115

<210> SEQ ID NO 162
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Thr Gly Gly Gly Leu Val Gln Pro Gly Gly Ser Leu Arg Leu Ser Cys
 1               5                  10                  15

Ala Ala Ser Gly Ala Thr Leu Asp Thr Tyr Ile Ile Thr Trp Phe Arg
                 20                  25                  30

Gln Ala Pro Gly Lys Glu Arg Glu Ala Val Ser Cys Ile Asn Arg Ser
                 35                  40                  45

Gly Ser Thr Thr Tyr Ser Asp Ser Val Lys Gly Arg Phe Thr Ile Ser
                 50                  55                  60

Arg Asp Asn Ala Gln Lys Thr Val Tyr Leu Gln Met Asn Ser Leu Asn
 65                  70                  75                  80

Pro Glu Asp Thr Ala Ile Tyr Tyr Cys Ala Ala Asp Ala Ser Tyr Arg
```

85                  90                  95

Thr Cys Gly Gly Ser Trp Trp Asn Trp Ala Tyr Trp Gly Gln Gly Thr
                100                 105                 110

Gln Val Thr Val Ser Ser
        115

<210> SEQ ID NO 163
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Ser Gly Gly Gly Ser Val Gln Pro Gly Gly Ser Leu Arg Leu Ser Cys
1               5                   10                  15

Ala Ala Ser Gly Phe Thr Phe Ser Ser Tyr Thr Met Ser Trp Val Arg
                20                  25                  30

Gln Ala Pro Gly Lys Gly Ile Glu Trp Val Ser Asp Ile Asn Gly Gly
            35                  40                  45

Gly Asp Arg Thr Asp Tyr Ala Asp Ser Val Lys Gly Arg Phe Thr Ile
        50                  55                  60

Ser Arg Asp Asn Ala Arg Asn Thr Leu Tyr Leu Gln Met Asn Ser Leu
65                  70                  75                  80

Gln Pro Glu Asp Thr Ala Val Tyr Tyr Cys Ala Lys Asp Leu Ser Tyr
                85                  90                  95

Val Ser Gly Thr Tyr Phe Ala Asn Asp Trp Gly Gln Gly Thr Gln Val
                100                 105                 110

Thr Val Ser Ser
        115

<210> SEQ ID NO 164
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Ser Gly Gly Gly Leu Val Gln Pro Gly Gly Ser Leu Arg Leu Ser Cys
1               5                   10                  15

Thr Ala Ser Gly Ile Ile Phe Asp Tyr Tyr Ser Val Asp Trp Tyr Arg
                20                  25                  30

Gln Ala Pro Gly Lys Glu Arg Glu Leu Val Ala Thr Ile Thr Gly Asp
            35                  40                  45

Gly Ser Pro Asn Tyr Ala Asp Ser Val Lys Gly Arg Phe Thr Ile Ser
        50                  55                  60

Arg Asp Asn Ala Lys Lys Thr Val Tyr Leu Gln Met Asn Gly Leu Lys
65                  70                  75                  80

Pro Glu Glu Thr Ala Val Tyr Tyr Cys His Ala Lys Arg Thr Ile Gly
                85                  90                  95

Thr Lys Ser Glu Tyr Trp Gly Gln Gly Thr Gln Val Thr Val Ser Ser
                100                 105                 110

<210> SEQ ID NO 165
<211> LENGTH: 109
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 165

Thr Gly Gly Leu Val Gln Ala Gly Gly Ser Leu Arg Leu Ser Cys
1               5                   10                  15

Leu Ala Ser Arg Met Ser Phe Ser Arg Arg Pro Met Ala Trp Tyr Arg
            20                  25                  30

Gln Ala Pro Gly Lys Gln Arg Glu Arg Val Ala Thr Ile Ser Ser Phe
        35                  40                  45

Gly Asp Thr Thr Asn Tyr Thr Asp Ser Val Glu Gly Arg Phe Thr Ile
    50                  55                  60

Ser Arg Asp Asn Ala Lys Asn Thr Met Tyr Leu Gln Met Asn Ser Leu
65                  70                  75                  80

Lys Pro Asp Asp Thr Ala Val Tyr Tyr Cys Asn Thr Leu Leu Ala Thr
                85                  90                  95

Tyr Ala Trp Gly Gln Gly Thr Gln Val Thr Val Ser Ser
            100                 105

<210> SEQ ID NO 166
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Ser Gly Gly Gly Leu Val Gln Ala Gly Gly Ser Leu Arg Leu Ser Cys
1               5                   10                  15

Ala Ala Ser Gly Arg Thr Phe Ser Ser Tyr Val Met Gly Trp Phe Arg
            20                  25                  30

Gln Ala Pro Gly Lys Glu Arg Glu Phe Val Ala Ala Ile Ser Arg Asn
        35                  40                  45

Gly Gly Lys Thr Tyr Tyr Ala Asp Ser Val Lys Gly Arg Phe Thr Ile
    50                  55                  60

Ser Arg Asp Gly Thr Glu Asn Thr Val Tyr Leu Gln Met Asn Ser Leu
65                  70                  75                  80

Lys Pro Glu Asp Thr Ala Val Tyr Tyr Cys Ala Ala Val Ala Ala
                85                  90                  95

Ser Ala Glu Phe Val Thr Ala Arg Ser Asn Phe Glu Tyr Trp Gly
            100                 105                 110

Gln Gly Thr Gln Val Thr Val Ser Ser
        115                 120

<210> SEQ ID NO 167
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

```
Cys Gly Pro Cys Lys Met Ile Ala Pro Ile Leu Asp Glu Ile Ala Asp
         35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
                100                 105                 110

Ser Gly His Met His His His His His His Ser Ser Gly Leu Val Pro
             115                 120                 125

Arg Gly Ser Gly Met Lys Glu Thr Ala Ala Lys Phe Glu Arg Gln
         130                 135                 140

His Met Asp Ser Pro Asp Leu Gly Thr Asp Asp Asp Lys Ala Met
145                 150                 155                 160

Ala Ile Ser Asp Pro Asn Ser Gly Ala Pro Val Pro Tyr Pro Asp Pro
                165                 170                 175

Leu Glu Pro Arg Ala Ala Ala Gln Val Gln Leu Ala Glu Ser Gly Gly
            180                 185                 190

Gly Leu Val Gln Pro Gly Gly Ser Leu Gly Leu Ser Cys Val Val Ala
            195                 200                 205

Ser Glu Arg Ser Ile Asn Asn Tyr Gly Met Gly Trp Tyr Arg Gln Ala
210                 215                 220

Pro Gly Lys Gln Arg Glu Leu Val Ala Gln Ile Ser Ser Gly Gly Thr
225                 230                 235                 240

Thr Asn Tyr Ala Asp Ser Val Glu Gly Arg Phe Thr Ile Ser Arg Asp
                245                 250                 255

Asn Val Lys Lys Met Val His Leu Gln Val Asn Ser Leu Lys Pro Glu
            260                 265                 270

Asp Thr Ala Val Tyr Tyr Cys Asn Ser Leu Leu Arg Thr Phe Ser Trp
            275                 280                 285

Gly Gln Gly Thr Gln Val Thr Val Ser Ser Glu Pro Lys Thr Pro Lys
290                 295                 300

Pro Gln Ala Ile Ala Gly Gly Gly Ser Gly Gly Gly Ser Gly
305                 310                 315                 320

Gly Gly Gly Ser Leu Gln Gly Gln Val Gln Leu Val Glu Ser Gly Gly
                325                 330                 335

Gly Leu Val Gln Pro Gly Gly Ser Leu Ser Val Ser Cys Ala Ala Ser
            340                 345                 350

Gly Ser Ile Ala Arg Pro Gly Ala Met Ala Trp Tyr Arg Gln Ala Pro
            355                 360                 365

Gly Lys Glu Arg Glu Leu Val Ala Ser Ile Thr Pro Gly Gly Leu Thr
            370                 375                 380

Asn Tyr Ala Asp Ser Val Thr Gly Arg Phe Thr Ile Ser Arg Asp Asn
385                 390                 395                 400

Ala Lys Arg Thr Val Tyr Leu Gln Met Asn Ser Leu Gln Pro Glu Asp
                405                 410                 415

Thr Ala Val Tyr Tyr Cys His Ala Arg Ile Ile Pro Leu Gly Leu Gly
            420                 425                 430

Ser Glu Tyr Arg Asp His Trp Gly Gln Gly Thr Gln Val Thr Val Ser
            435                 440                 445
```

```
Ser Ala His His Ser Glu Asp Pro Ser Ala Arg Gln Gly Ala Pro Val
    450                 455                 460
Pro Tyr Pro Asp Pro Leu Glu Pro Arg Gly Gly Gly Ser Asp Ile Cys
465                 470                 475                 480
Leu Pro Arg Trp Gly Cys Leu Trp Glu Asp
                485                 490

<210> SEQ ID NO 168
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Met Ser Asp Lys Ile Ile His Leu Thr Asp Ser Phe Asp Thr Asp
1               5                   10                  15
Val Leu Lys Ala Asp Gly Ala Ile Leu Val Asp Phe Trp Ala Glu Trp
                20                  25                  30
Cys Gly Pro Cys Lys Met Ile Ala Pro Ile Leu Asp Glu Ile Ala Asp
            35                  40                  45
Glu Tyr Gln Gly Lys Leu Thr Val Ala Lys Leu Asn Ile Asp Gln Asn
    50                  55                  60
Pro Gly Thr Ala Pro Lys Tyr Gly Ile Arg Gly Ile Pro Thr Leu Leu
65                  70                  75                  80
Leu Phe Lys Asn Gly Glu Val Ala Ala Thr Lys Val Gly Ala Leu Ser
                85                  90                  95
Lys Gly Gln Leu Lys Glu Phe Leu Asp Ala Asn Leu Ala Gly Ser Gly
            100                 105                 110
Ser Gly His Met His His His His His Ser Ser Gly Leu Val Pro
    115                 120                 125
Arg Gly Ser Gly Met Lys Glu Thr Ala Ala Ala Lys Phe Glu Arg Gln
130                 135                 140
His Met Asp Ser Pro Asp Leu Gly Thr Asp Asp Asp Asp Lys Ala Met
145                 150                 155                 160
Ala Ile Ser Asp Pro Asn Ser Gly Ala Pro Val Pro Tyr Pro Asp Pro
                165                 170                 175
Leu Glu Pro Arg Ala Ala Ala Gln Val Gln Leu Ala Glu Ser Gly Gly
            180                 185                 190
Gly Leu Val Gln Pro Gly Gly Ser Leu Gly Leu Ser Cys Val Val Ala
        195                 200                 205
Ser Glu Arg Ser Ile Asn Asn Tyr Gly Met Gly Trp Tyr Arg Gln Ala
210                 215                 220
Pro Gly Lys Gln Arg Glu Leu Val Ala Gln Ile Ser Ser Gly Gly Thr
225                 230                 235                 240
Thr Asn Tyr Ala Asp Ser Val Glu Gly Arg Phe Thr Ile Ser Arg Asp
                245                 250                 255
Asn Val Lys Lys Met Val His Leu Gln Val Asn Ser Leu Lys Pro Glu
            260                 265                 270
Asp Thr Ala Val Tyr Tyr Cys Asn Ser Leu Leu Arg Thr Phe Ser Trp
        275                 280                 285
Gly Gln Gly Thr Gln Val Thr Val Ser Ser Glu Pro Lys Thr Pro Lys
    290                 295                 300
Pro Gln Ala Ile Ala Gly Gly Gly Ser Gly Gly Gly Gly Ser Gly
305                 310                 315                 320
```

Gly Gly Gly Ser Leu Gln Gly Gln Val Gln Leu Ala Glu Ser Gly Gly
            325                 330                 335
Gly Gly Leu Val Gln Ala Gly Gly Ser Leu Arg Leu Ser Cys Ala Ala
            340                 345                 350
Ser Gly Arg Thr Phe Ser Gly Tyr Ala Met Gly Trp Phe Arg Gln Ala
            355                 360                 365
Pro Gly Lys Glu Arg Glu Phe Val Ala Asp Ile Ser Trp Ser Gly His
        370                 375                 380
Asn Thr Tyr Tyr Gly Asp Ser Val Lys Gly Arg Phe Thr Ile Ser Arg
385                 390                 395                 400
Asp Thr Ala Lys Asn Thr Val Tyr Leu Gln Met Asn Ser Leu Lys Pro
            405                 410                 415
Glu Asp Thr Ala Val Tyr Tyr Cys Ala Ala Glu Gly Ala Arg Thr His
            420                 425                 430
Leu Ser Asp Ser Tyr Tyr Phe Pro Gly Leu Trp Ala Glu Pro Pro Val
            435                 440                 445
Gly Tyr Trp Gly Gln Gly Thr Gln Val Thr Val Ser Ser Glu Pro Lys
        450                 455                 460
Thr Pro Lys Pro Gln Pro Ala Arg Gln Gly Ala Pro Val Pro Tyr Pro
465                 470                 475                 480
Asp Pro Leu Glu Pro Arg Gly Gly Ser Asp Ile Cys Leu Pro Arg
            485                 490                 495
Trp Gly Cys Leu Trp Glu Asp
            500

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 169

His His His His His His
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ser Gly Ser Ile Ala Arg Pro Gly Ala
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ser Ile Thr Pro Gly Gly Leu Thr Asn
1               5

<210> SEQ ID NO 172
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

His Ala Arg Ile Ile Pro Leu Gly Leu Gly Ser Glu Tyr Arg Asp His
1               5                   10                  15

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Ser Glu Arg Ser Ile Asn Asn Tyr Gly
1               5                   10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Ile Ser Ser Gly Gly Thr Thr Asn
1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asn Ser Leu Leu Arg Thr Phe Ser
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Gly Leu Thr Phe Gly Asn Tyr Ala
1               5

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 177

Ser Ile Ser Arg Ser Gly Ser Asn Thr Trp
1               5                   10

<210> SEQ ID NO 178
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ala Gly Gly Ser Tyr Asn Ser Asp Trp Trp Asn Tyr Met Tyr
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Gly Arg Thr Phe Ser Gly Tyr Ala
1               5

<210> SEQ ID NO 180
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Ile Ser Trp Ser Gly His Asn Thr Tyr
1               5                   10

<210> SEQ ID NO 181
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ala Glu Gly Ala Arg Thr His Leu Ser Asp Ser Tyr Tyr Phe Pro Gly
1               5                   10                  15

Leu Trp Ala Glu Pro Pro Val Gly Tyr
            20                  25

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Gly Arg Thr Phe Thr Ser Tyr Tyr
1               5
```

```
<210> SEQ ID NO 183
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Ile Gly Trp Thr Asp Asp Asn Thr Tyr
1               5                   10

<210> SEQ ID NO 184
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ala Ala Asp Tyr Gly Ser Gly Ile Arg Ala Trp Tyr Asn Trp Ile Tyr
1               5                   10                  15

<210> SEQ ID NO 185
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Gly Ala Thr Leu Asp Thr Tyr Ile Ile
1               5                   10

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Ile Asn Arg Ser Gly Ser Thr Thr
1               5

<210> SEQ ID NO 187
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ala Ala Asp Ala Ser Tyr Arg Thr Cys Gly Gly Ser Trp Trp Asn Trp
1               5                   10                  15

Ala Tyr

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 188

Ser Gly Phe Thr Phe Ser Ser Tyr Thr
1               5

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Asp Ile Asn Gly Gly Gly Asp Arg Thr Asp
1               5                   10

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Lys Asp Leu Ser Tyr Val Ser Gly Thr Tyr Phe Ala Asn Asp
1               5                   10                  15

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Gly Ile Ile Phe Asp Tyr Tyr Ser Val
1               5                   10

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Thr Ile Thr Gly Asp Gly Ser Pro Asn
1               5

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

His Ala Lys Arg Thr Ile Gly Thr Lys Ser Glu Tyr
1               5                   10

<210> SEQ ID NO 194
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Arg Met Ser Phe Ser Arg Arg Pro
1               5

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Ile Ser Ser Phe Gly Asp Thr Thr Asn
1               5                   10

<210> SEQ ID NO 196
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asn Thr Leu Leu Ala Thr Tyr Ala
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Gly Arg Thr Phe Ser Ser Tyr Val
1               5

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ala Ile Ser Arg Asn Gly Gly Lys Thr Tyr
1               5                   10

<210> SEQ ID NO 199
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ala Ala Ala Val Ala Ala Ser Ala Glu Phe Val Thr Ala Arg Ser Asn
```

```
1               5                   10                  15
Phe Tyr Glu Tyr
            20

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Gln Gly Thr Gln Val Thr Val Ser Ser
1               5                   10

<210> SEQ ID NO 204
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Gly Gly Gly Gly Leu Val Gln Ala Gly Gly Ser Leu Arg Leu Ser
1               5                   10                  15

Cys Ala

<210> SEQ ID NO 205
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Gly Trp Phe Arg Gln Ala Pro Gly Lys Glu Arg Glu Phe Val
1               5                   10

<210> SEQ ID NO 206
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 206

Tyr Gly Asp Ser Val Lys Gly Arg Phe Thr Ile Ser Arg Asp Thr Ala
1               5                   10                  15

Lys Asn Thr Val Tyr Leu Gln Met Asn Ser Leu Lys Pro Glu Asp Thr
            20                  25                  30

Ala Val Tyr Tyr
        35

<210> SEQ ID NO 207
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Gly Gly Gly Leu Val Gln Pro Gly Gly Ser Leu Ser Val Ser Cys
1               5                   10                  15

Ala

<210> SEQ ID NO 208
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Gly Gly Gly Leu Val Gln Pro Gly Gly Ser Leu Gly Leu Ser Cys
1               5                   10                  15

Val

<210> SEQ ID NO 209
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Thr Gly Gly Gly Leu Val Gln Ala Gly Gly Ser Leu Arg Leu Ser Cys
1               5                   10                  15

Ser

<210> SEQ ID NO 210
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Thr Gly Gly Gly Leu Val Gln Ala Gly Gly Thr Leu Arg Leu Ser Cys
1               5                   10                  15

Ala

<210> SEQ ID NO 211
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 211

Thr Gly Gly Gly Leu Val Gln Pro Gly Gly Ser Leu Arg Leu Ser Cys
1               5                   10                  15

Ala

<210> SEQ ID NO 212
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Gly Gly Gly Ser Val Gln Pro Gly Gly Ser Leu Arg Leu Ser Cys
1               5                   10                  15

Ala

<210> SEQ ID NO 213
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Gly Gly Gly Leu Val Gln Pro Gly Gly Ser Leu Arg Leu Ser Cys
1               5                   10                  15

Thr

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Thr Gly Gly Gly Leu Val Gln Ala Gly Gly Ser Leu Arg Leu Ser Cys
1               5                   10                  15

Leu

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Gly Gly Gly Leu Val Gln Ala Gly Gly Ser Leu Arg Leu Ser Cys
1               5                   10                  15

Ala

<210> SEQ ID NO 216
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ala Trp Tyr Arg Gln Ala Pro Gly Lys Glu Arg Glu Leu Val
1               5                   10

<210> SEQ ID NO 217
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Trp Tyr Arg Gln Ala Pro Gly Lys Gln Arg Glu Leu Val
1               5                   10

<210> SEQ ID NO 218
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Trp Phe Arg Gln Glu Pro Gly Lys Glu Arg Glu Phe Val
1               5                   10

<210> SEQ ID NO 219
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Trp Phe Arg Gln Ala Pro Gly Lys Glu Arg Glu Ala Val
1               5                   10

<210> SEQ ID NO 220
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Trp Val Arg Gln Ala Pro Gly Lys Gly Ile Glu Trp Val
1               5                   10

<210> SEQ ID NO 221
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Asp Trp Tyr Arg Gln Ala Pro Gly Lys Glu Arg Glu Leu Val
```

```
1               5                   10

<210> SEQ ID NO 222
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ala Trp Tyr Arg Gln Ala Pro Gly Lys Gln Arg Glu Arg Val
1               5                   10

<210> SEQ ID NO 223
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Tyr Ala Asp Ser Val Thr Gly Arg Phe Thr Ile Ser Arg Asp Asn Ala
1               5                   10                  15

Lys Arg Thr Val Tyr Leu Gln Met Asn Ser Leu Gln Pro Glu Asp Thr
            20                  25                  30

Ala Val Tyr Tyr
        35

<210> SEQ ID NO 224
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Tyr Ala Asp Ser Val Glu Gly Arg Phe Thr Ile Ser Arg Asp Asn Val
1               5                   10                  15

Lys Lys Met Val His Leu Gln Val Asn Ser Leu Lys Pro Glu Asp Thr
            20                  25                  30

Ala Val Tyr Tyr
        35

<210> SEQ ID NO 225
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Tyr Ala Glu Pro Leu Lys Gly Arg Phe Ala Ile Ser Arg Asp Asn Asp
1               5                   10                  15

Lys Asn Ala Leu Tyr Leu Gln Met Asn Ser Leu Lys Pro Glu Asp Thr
            20                  25                  30

Ala Val Tyr Tyr
        35

<210> SEQ ID NO 226
<211> LENGTH: 36
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Tyr Ala Asp Ser Val Lys Gly Arg Phe Thr Ile Ser Arg Asp Asn Ala
1               5                   10                  15

Glu Thr Thr Ala Tyr Leu Gln Asn Ser Gly Leu Lys Pro Glu Asp Thr
            20                  25                  30

Ala Val Tyr Tyr
        35

<210> SEQ ID NO 227
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Tyr Ser Asp Ser Val Lys Gly Arg Phe Thr Ile Ser Arg Asp Asn Ala
1               5                   10                  15

Gln Lys Thr Val Tyr Leu Gln Met Asn Ser Leu Asn Pro Glu Asp Thr
            20                  25                  30

Ala Ile Tyr Tyr
        35

<210> SEQ ID NO 228
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Tyr Ala Asp Ser Val Lys Gly Arg Phe Thr Ile Ser Arg Asp Asn Ala
1               5                   10                  15

Arg Asn Thr Leu Tyr Leu Gln Met Asn Ser Leu Gln Pro Glu Asp Thr
            20                  25                  30

Ala Val Tyr Tyr
        35

<210> SEQ ID NO 229
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Tyr Ala Asp Ser Val Lys Gly Arg Phe Thr Ile Ser Arg Asp Asn Ala
1               5                   10                  15

Lys Lys Thr Val Tyr Leu Gln Met Asn Gly Leu Lys Pro Glu Glu Thr
            20                  25                  30

Ala Val Tyr Tyr
        35

<210> SEQ ID NO 230
```

```
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Tyr Thr Asp Ser Val Glu Gly Arg Phe Thr Ile Ser Arg Asp Asn Ala
1               5                   10                  15

Lys Asn Thr Met Tyr Leu Gln Met Asn Ser Leu Lys Pro Asp Asp Thr
            20                  25                  30

Ala Val Tyr Tyr
        35

<210> SEQ ID NO 231
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Tyr Ala Asp Ser Val Lys Gly Arg Phe Thr Ile Ser Arg Asp Gly Thr
1               5                   10                  15

Glu Asn Thr Val Tyr Leu Gln Met Asn Ser Leu Lys Pro Glu Asp Thr
            20                  25                  30

Ala Val Tyr Tyr
        35

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Ser Gly Ser Ser Phe Ser Arg Tyr Ala
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Gly Phe Ile Phe Ser Leu Tyr Thr
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Gly Ile Ile Phe Ser Ile Tyr Thr
1               5
```

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Gly Leu Thr Phe Ser Ser Thr Ala
1               5

<210> SEQ ID NO 236
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Arg Ser Thr Thr Ala Thr Ile Tyr Ser
1               5                   10

<210> SEQ ID NO 237
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Pro Glu Ser Ile Val Asn Ser Arg Thr
1               5

<210> SEQ ID NO 238
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Gly Phe Thr Phe Ser Ser Tyr Arg
1               5

<210> SEQ ID NO 239
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Gly Val Ile Phe Ser Ile Tyr Thr
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 240

Ser Gly Arg Tyr Ala
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Asn Ile Asn Ser Arg Gly Thr Ser Asn
1               5

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Thr Ile Thr Ser Ala Thr Gly Ile Thr Asn
1               5                   10

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ala Ile Pro Ser Gly Pro Ser Ala Asn
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Arg Ile Ser Gly Ala Gly Ile Thr Ile Tyr
1               5                   10

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gly Met Thr Ser Asp Gly Gln Thr Asn
1               5

<210> SEQ ID NO 246
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Ile Thr Thr Ala Gly Ser Pro Asn
1               5

<210> SEQ ID NO 247
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Ile Thr Ala Asn Gly Val Pro Thr Gly
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Ala Ile Gly Val Ala Asp Gly Thr Ala Leu
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Ile Ser Arg Ser Gly Ala Ile Arg Glu
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Asn Ala Glu Trp Leu Gly Arg Ser Glu Pro Ser
1               5                   10

<210> SEQ ID NO 251
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Asn Ala Val Arg Thr Thr Val Ser Arg Asp Tyr
```

```
<210> SEQ ID NO 252
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asn Ala Arg Arg Gly Pro Gly Ile Lys Asn Tyr
1               5                   10

<210> SEQ ID NO 253
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Ala Ala Arg Arg Asn Thr Tyr Thr Ser Asp Tyr Asn Ile Pro Ala Arg
1               5                   10                  15

Tyr Pro Tyr

<210> SEQ ID NO 254
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Tyr Val Lys Pro Trp Arg Leu Gln Gly Trp Asp Tyr
1               5                   10

<210> SEQ ID NO 255
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Asn Thr Leu Leu Ser Thr Leu Pro
1               5

<210> SEQ ID NO 256
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Asn Ala Pro Arg Leu His Thr Ser Val Gly Tyr
1               5                   10

<210> SEQ ID NO 257
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 257

Ala Ala Tyr Leu Ser Pro Arg Val Gln Ser Pro Tyr Ile Thr Asp Ser
1               5                   10                  15

Arg Tyr Gln Leu
            20

<210> SEQ ID NO 258
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Glu Gly Arg Gly Ala Thr Phe Asn Pro Glu Tyr Ala Tyr
1               5                   10

<210> SEQ ID NO 259
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ala Ala Glu Gly Ala Arg Thr His Leu Ser Asp Ser Tyr Tyr Phe Pro
1               5                   10                  15

Gly Leu Trp Ala Glu Pro Pro Val Gly Tyr
            20                  25
```

VHH BASED BINDING ANTIBODIES FOR ANTHRAX AND BOTULINUM TOXINS AND METHODS OF MAKING AND USING THEREFOR

RELATED APPLICATION

This application claims priority to U.S. provisional application Ser. No. 62/089,949 filed Dec. 10, 2014 entitled "VHH based neutralizing antibodies for Anthrax and Botulinum toxins", inventor Charles 3. Shoemaker, which is incorporated by reference herein in its entirety.

GOVERNMENT SUPPORT

This invention was made with government support under grant numbers AI057159 and AI093467 awarded by the National Institutes of Health. The government has certain rights in the invention.

SEQUENCE LISTING

The application contains a Sequence Listing which has been submitted electronically in ASCII format and is hereby incorporated by reference in its entirety. The ASCII copy, created on Dec. 23, 2020, is named 167774_011402_US_SL.txt and is 216,354 bytes in size.

TECHNICAL FIELD

The present invention generally relates to compositions and methods to prevent or treat exposure to Anthrax toxin or to Botulinum toxins by VHH based neutralizing antibodies.

BACKGROUND

The disease, Anthrax is caused by the gram-positive bacterium *Bacillus anthracis* and is a major bioterror concern. Following introduction into a host in spore form and germination of the spore, the bacterium divides and manifests disease and lethality primarily through the action of two toxins, anthrax lethal toxin (LT) and edema toxin (ET). Anthrax toxins have a common receptor-binding component, protective antigen (PA), which is responsible for transport of the lethal factor metalloprotease (LF) or edema factor adenylate cyclase (EF) or both into the host cell cytosol. Injection of the toxins into animals replicates symptoms of anthrax disease.

PA acts as a 'gateway' that allows translocation and action of both LT and ET toxins and hence PA has been the primary target of therapeutics including antibodies developed for treatment of anthrax. PA binds to two cellular receptors as an 83 kDa polypeptide (PA83) and is rapidly cleaved by cell surface proteases such as furin to a 63 kDa (PA63) form which associates as heptamers or octamers that provide the binding sites for LF or EF. The oligomer bound to one or more molecules of LF/EF is then rapidly translocated. PA63 form of the Anthrax toxin is competent for endocytosis. When PA is cleaved prior to exposure to cells, or produced as PA63, it rapidly oligomerizes and the pre-formed oligomer binds and transports LF/EF into cells. The PA63 oligomer undergoes a conformational change in acidic endosomes to a heat and SDS-stable form, which allows the translocation of LF and EF through a central pore into the cytosol. LF and EF then act on their substrates and manifest toxic effects.

During anthrax infection, the accumulation of anthrax toxins in the blood leads to lethality. Antibodies against PA are considered a primary therapeutic for treatment of the disease. The majority of neutralizing antibodies developed against PA act on the receptor-binding domain to inhibit interaction of the toxin with cells. A few antibodies have been identified which neutralize PA by other mechanisms.

Botulinum toxin is a neurotoxin produced by the bacterium *Clostridium botulinum*. Botulinum toxin is released by *C. botulinum* spores, which are commonly found in soil and water. The *C. botulinum* spores produce botulinum toxin on exposure to low oxygen levels and certain temperatures. Botulinum toxin can cause Botulism, which is a serious and life-threatening paralytic illness in humans and animals. The early symptoms of Botulism are weakness, trouble seeing, feeling tired, and trouble speaking followed by weakness of the arms, chest muscles and legs. Botulinum toxin is an acute lethal toxin with an estimated human median lethal dose (LD-50) of 1.3-2.1 ng/kg intravenously or intramuscularly and 10-13 ng/kg when inhaled. Antibodies against Botulinum toxins are considered a primary therapeutic for treatment of the disease.

A need exists for generating high affinity binding agents that treat both routine incidents of disease and toxicity. The production of antibodies and their storage is a costly and lengthy process. In fact, development of a single antibody therapeutic agent often requires years of clinical study. Yet multiple, different therapeutic antibodies are necessary for the effective treatment of patients exposed to a bio-terrorist assault with a potential weapon such as Anthrax or Botulism. Developing and producing multiple antibodies each of which can bind to a different target (e.g. microbial pathogens, viral pathogens, and toxins) is often a difficult task because it involves separately producing, storing and transporting each of the multiplicity of antibodies of which each is specific for one pathogen or toxin. Production and stockpiling a sufficient amount of antibodies to protect large populations is a challenge and has not currently been achieved. The shelf life of antibodies is often relatively short (e.g., weeks or months), and accordingly freshly prepared batches of present therapeutic antibodies have to be produced to replace expiring antibodies.

Accordingly, there is a need for a cost effective and efficient way to provide alternatives to current therapeutic agents. Further a need exists for alternative therapeutics that are easier to develop and produce, have a longer shelf life, and bind as a single agent to multiple targets on the same disease agent, as well as to different disease agents.

SUMMARY

An aspect of invention provides a pharmaceutical composition for treating a subject at risk for exposure to or exposed to at least one disease agent, the pharmaceutical composition including: at least one recombinant binding protein that neutralizes the disease agent and treats the subject for exposure to the disease agent, the binding protein including at least one amino acid sequence selected from the group of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143.

In some embodiments of the composition, the recombinant binding protein is encoded by at least one nucleotide sequence selected from the group of: SEQ ID NO: 2, SEQ ID NO: 4 SEQ ID NO: 6, SEQ ID NO: 8, SEQ ID NO: 10, SEQ ID NO: 12, SEQ ID NO: 14 SEQ ID NO: 16, SEQ ID NO: 18, SEQ ID NO: 20, SEQ ID NO: 22, SEQ ID NO: 24 SEQ ID NO: 26, SEQ ID NO: 28, SEQ ID NO: 30, SEQ ID NO: 32, SEQ ID NO: 34 SEQ ID NO: 36, SEQ ID NO: 38, SEQ ID NO: 40, SEQ ID NO: 42, SEQ ID NO: 44 SEQ ID NO: 46, SEQ ID NO: 48, SEQ ID NO: 50, SEQ ID NO: 52, SEQ ID NO: 54 SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144. In an embodiment of the composition, the binding protein is heteromultimeric and has a plurality of binding regions. In another embodiment of the composition, the binding regions are not identical and each binding region has affinity to specifically bind and neutralize a non-overlapping portion of the disease agent.

In an embodiment of the composition, the binding protein further includes at least one of: a tag epitope that has affinity to bind an antibody; and a linker that separates the binding regions, and the linker including at least one selected from the group of: a peptide, a protein, a sugar, and a nucleic acid. In an embodiment of the composition, the disease agent is a toxin selected from a plant lectin and a bacterial toxin. In some embodiments, the bacterial toxin is at least one selected from a *B. anthracis* toxin, a *C. botulinum* B toxin, and a *C. botulinum* E toxin. In an embodiment of the composition, the bacterial toxin is a *B. anthracis* toxin and the binding protein binds to and neutralizes at least one selected from: an Anthrax protective antigen, an Anthrax lethal toxin, and an Anthrax edema toxin. In some embodiments, the binding protein inhibits or prevents endocytosis of the toxin. In some embodiments, the Anthrax protective antigen is a cell surface generated antigen.

In various embodiments of the composition, the amino acid sequence is substantially identical and has at least 50% identity, at least 60% identity, at least 65% identity, at least 70% identity, at least 75% identity, at least 80% identity, at least 85% identity, at least 90% identity, or and at least 95% identity to the amino acid sequence. In some embodiments, the nucleotide sequence is substantially identical and has at least 50% identity, at least 60% identity, at least 65% identity, at least 70% identity, at least 75% identity, at least 80% identity, at least 85% identity, at least 90% identity, or and at least 95% identity to the nucleotide sequence.

An aspect of the invention provides a method for treating a subject at risk for exposure to or exposed to at least one disease agent, the method including: administering to the subject at least one binding protein having at least one binding region including an amino acid sequence selected from: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143, and measuring a decrease in at least one symptom associated with exposure to disease agent.

In an embodiment of the method, measuring the symptom further comprises analyzing an amount of remediation of at least one symptom selected from fever, chills, swelling of neck, soreness of neck glands, sore throat, painful swallowing, hoarseness, nausea, vomiting, bloody vomiting, diarrhea, bloody diarrhea, constipation, headache, flushing, red eyes, stomach pain, fainting, swelling of abdomen, double vision, blurred vision, drooping eyelids, slurred speech, dry mouth, and muscle weakness.

An aspect of the invention provides a method of identifying a therapeutic binding protein for treating a subject at risk for exposure to or exposed to at least one disease agent, the method including: contacting a first sample of a disease agent with a test protein and measuring an amount of binding of the disease agent to the test protein under conditions for the disease agent to interact with the test protein; and comparing the amount of binding to that of a second sample of the disease agent not contacted by the test protein and otherwise identical, such that presence of the therapeutic binding protein is identified by an increase of binding of the disease agent in the first sample compared to the second sample.

In an embodiment of the method, the test protein is a plurality of proteins. In some embodiments, the disease agent is in vitro. In other embodiments, the disease agent is in a cell.

An embodiment of the method further includes contacting the disease agent to a mammalian subject and measuring a decrease in at least one symptom of the disease agent. In some embodiments, the disease agent is a toxin selected from a plant lectin and a bacterial toxin. In some embodiments, the bacterial toxin is at least one selected from a *B. anthracis* toxin, a *C. botulinum* B toxin, and a *C. botulinum* E toxin. In some embodiments, the bacterial toxin is a *B. anthracis* toxin and the binding protein binds to and neutralizes Anthrax protective antigen. In an embodiment, the binding protein inhibits or prevents endocytosis of the toxin. In an embodiment of the method, the Anthrax protective antigen is a cell surface generated antigen.

An aspect of the invention provides a method for treating a subject at risk for exposure to or exposed to at least one disease agent, the method including: administering to the subject a source of expression of a binding protein having a nucleotide sequence encoding the binding protein, such that the nucleotide sequence comprises at least one selected from the group consisting of: a naked nucleic acid vector, bacterial vector, and a viral vector, such that the nucleotide sequence includes at least one selected from the group of: SEQ ID NO: 2, SEQ ID NO: 4 SEQ ID NO: 6, SEQ ID NO: 8, SEQ ID NO: 10, SEQ ID NO: 12, SEQ ID NO: 14 SEQ ID NO: 16, SEQ ID NO: 18, SEQ ID NO: 20, SEQ ID NO: 22, SEQ ID NO: 24 SEQ ID NO: 26, SEQ ID NO: 28, SEQ ID NO: 30, SEQ ID NO: 32, SEQ ID NO: 34 SEQ ID NO: 36, SEQ ID NO: 38, SEQ ID NO: 40, SEQ ID NO: 42, SEQ ID NO: 44 SEQ ID NO: 46, SEQ ID NO: 48, SEQ ID NO: 50, SEQ ID NO: 52, SEQ ID NO: 54 SEQ ID NO: 56, SEQ ID NO: 58, SEQ ID NO: 60, SEQ ID NO: 62, SEQ ID NO: 64 SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144.

An aspect of the invention provides a kit for treating a subject exposed to or at risk for exposure to a disease agent including: a unit dosage of a pharmaceutical composition for treating a subject at risk for exposure to or exposed to at least one disease agent, the pharmaceutical composition including: at least one recombinant binding protein that neutralizes the disease agent thereby treating the subject for exposure to the disease agent, such that the binding protein includes at least one amino acid sequence selected from the group of: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143.

In an embodiment of the kit, the recombinant binding protein is encoded by at least one nucleotide sequence selected from the group of: SEQ ID NO: 2, SEQ ID NO: 4 SEQ ID NO: 6, SEQ ID NO: 8, SEQ ID NO: 10, SEQ ID NO: 12, SEQ ID NO: 14 SEQ ID NO: 16, SEQ ID NO: 18, SEQ ID NO: 20, SEQ ID NO: 22, SEQ ID NO: 24 SEQ ID NO: 26, SEQ ID NO: 28, SEQ ID NO: 30, SEQ ID NO: 32, SEQ ID NO: 34 SEQ ID NO: 36, SEQ ID NO: 38, SEQ ID NO: 40, SEQ ID NO: 42, SEQ ID NO: 44 SEQ ID NO: 46, SEQ ID NO: 48, SEQ ID NO: 50, SEQ ID NO: 52, SEQ ID NO: 54 SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, SEQ ID NO: 102, SEQ ID NO: 104, SEQ ID NO: 106, SEQ ID NO: 108, SEQ ID NO: 110, SEQ ID NO: 112, SEQ ID NO: 114, SEQ ID NO: 116, SEQ ID NO: 118, SEQ ID NO: 120, SEQ ID NO: 122, SEQ ID NO: 124, SEQ ID NO: 126, SEQ ID NO: 128, SEQ ID NO: 130, SEQ ID NO: 132, SEQ ID NO: 134, SEQ ID NO: 136, SEQ ID NO: 138, SEQ ID NO: 140, SEQ ID NO: 142, and SEQ ID NO: 144.

An aspect of the invention provides a method for detecting a presence of a toxin in a sample, the method including: contacting and incubating an aliquot of the sample to an amount of at least one binding protein that specifically binds the toxin, such that the binding protein includes a binding region having an amino acid sequence selected from: SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 127, SEQ ID NO: 129, SEQ ID NO: 131, SEQ ID NO: 133, SEQ ID NO: 135, SEQ ID NO: 137, SEQ ID NO: 139, SEQ ID NO: 141, and SEQ ID NO: 143, such that the toxin is selected from the group of: a *B. anthracis* toxin, a *C. botulinum* B toxin and a *C. botulinum* E toxin, and SEQ ID NO: 1, SEQ ID NO: 3 SEQ ID NO: 5, SEQ ID NO: 7, SEQ ID NO: 9, SEQ ID NO: 11, SEQ ID NO: 13, SEQ ID NO: 15, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, and SEQ ID NO: 105 are amino acid sequences of binding proteins that specifically bind a *B. anthracis* toxin, and SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 107, SEQ ID NO: 109, SEQ ID NO: 111, SEQ ID NO: 113, SEQ ID NO: 115, SEQ ID NO: 117, SEQ ID NO: 119, SEQ ID NO: 121, SEQ ID NO: 123, SEQ ID NO: 125, SEQ ID NO: 131, SEQ ID NO: 133, SEQ ID NO: 135, and SEQ ID NO: 137 are amino acid sequences of binding proteins that specifically bind a *B. botulinum* B toxin, and SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 127, SEQ ID NO: 129, SEQ ID NO: 139, SEQ ID NO: 141, and SEQ ID NO: 143 are amino acid sequences of binding proteins that specifically bind a *B. botulinum* E toxin under conditions to form a complex; separating the complex from unbound binding protein; and measuring amount of complex formed.

In an embodiment of the method, the sample is at least one selected from: a medical sample, a food sample, a beverage sample, a water sample, and an environmental sample. In another embodiment of the invention, the medical sample is at least one selected from: blood, plasma, tissue, stool, urine, perspiration, serum, semen, breast milk, cerebrospinal fluid, skin and hair. An embodiment of the method further includes, analyzing the extent of complex formation, such that the extent of complex formation is a function of extent of toxin present in the sample.

BRIEF DESCRIPTION OF THE DRAWINGS

FIG. 1C shows a single group (POST) received antibody 2 hours after toxin was administered. Control groups were injected with PBS instead of antibody. Heterodimers JKC-5 and VNA1 (JKD-11) contain the VHHs JIK-B8 and JIJ-B8, both with high affinity for PA but only JIK-B8 having anthrax neutralizing properties. VNA2 contains JIK-B8 and JKH-C7, both potent anthrax neutralizing VHHs. Heterodimers VNA1 and VNA2 also contain a carboxyl albumin-binding-peptide (ABP) which prolongs in vivo serum persistence of similar VNAs in mice. Antibody 14B7 is a previously described neutralizing monoclonal antibody, which binds to the same receptor-interacting domain as JIK-B8. Animals were monitored for 10 days post for signs of malaise and survival.

FIG. 2A shows data obtained using C57BL/6J mice treated with VNA2 heterodimeric VNA or 14B7 mAb control (15 μg/injection/IV) at indicated times before or after spore infection. FIG. 2D shows data from C57BL/6J mice (n=5/group, except PBS controls, n=15), treated with heterodimeric VNA2-PA subcutaneously (SC) at indicated times and doses before or after spore infection ($2\times10^7$ spores, also SC at a distal site). Control mice were treated with PBS at 15 min, one hour and four hours post infection (n=5) or at five minutes (n=5) and eight hours (n=5) post infection. Neutralizing mAb 14B7 was used as a positive control in these studies. Mice were monitored for survival and signs of malaise for 10 days.

FIG. 3 shows amino acid sequences SEQ ID NOS 148-166 of VHHs selected for binding to anthrax PA. Sequences shown begin within framework 1 (FR1) at the site of the primer binding employed in coding sequence DNA amplification from the immune alpaca cDNA and continue through the end of framework 4 (FR4). The expression in parentheses at the right end indicates that the VHH contains a long hinge (lh) or a short hinge (sh). The locations of each of the three complementarity determining regions (CDRs) are indicated at the top end. FIG. 3 includes the following VHHs containing complementarity determining regions (CDRs), CDR1, CDR2 and CDR3: JIJ B8 (SEQ ID NO: 151) comprises CDR 1: SGSIARPGA (SEQ ID NO: 170); CDR2: SITPGGLTN (SEQ ID NO: 171); and CDR3: HARIIPLGLGSEYRDH (SEQ ID NO: 172); JIK-B8 (SEQ ID NO: 155) comprises CDR 1: ASERSINNYG (SEQ ID NO: 173); CDR2: QISSGGTTN (SEQ ID NO: 174); and CDR3: NSLLRTFS (SEQ ID NO: 175); JKH-A4 (SEQ ID NO: 159) comprises CDR 1: SGLTFGNYA (SEQ ID NO: 176); CDR2: SISRSGSNTW (SEQ ID NO: 177); and CDR3: AGGSYNSDWWNYMY (SEQ ID NO: 178); JHK-C7 (SEQ ID NO: 160) comprises CDR 1: SGRTFSGYA (SEQ ID NO: 179); CDR2: DISWSGHNTY (SEQ ID NO: 180); and CDR3: AEGARTHLSDSYYFPGLWAEPPVGY (SEQ ID NO: 181); JKH-D12 (SEQ ID NO: 161) comprises CDR 1: SGRTFTSYY (SEQ ID NO: 182); CDR2: SIGWTDDNTY (SEQ ID NO: 183); and CDR3: AADYGS-GIRAWYNWIY (SEQ ID NO: 184); JKM-A6 (SEQ ID NO: 162) comprises CDR 1: SGATLDTYII (SEQ ID NO: 185); CDR2: CINRSGSTT (SEQ ID NO: 186); and CDR3: AADASYRTCGGSWWNWAY (SEQ ID NO: 187); JKO-A4 (SEQ ID NO: 163) comprises CDR 1: SGFTFSSYT (SEQ ID NO: 188); CDR2: DINGGGDRTD (SEQ ID NO: 189); and CDR3: AKDLSYVSGTYFAND (SEQ ID NO: 190); JKO-B8 (SEQ ID NO: 164) comprises CDR 1: SGIIFDYYSV (SEQ ID NO: 191); CDR2: TITGDGSPN (SEQ ID NO: 192); and CDR3: HAKRTIGTKSEY (SEQ ID NO: 193); JKO-E12 (SEQ ID NO: 165) comprises CDR 1: SRMSFSRRP (SEQ ID NO: 194); CDR2: TISSFGDTTN (SEQ ID NO: 195); and CDR3: NTLLATYA (SEQ ID NO: 196); and JKO-H2 (SEQ ID NO: 166) comprises CDR 1: SGRTFSSYV (SEQ ID NO: 197); CDR2: AISRNGGKTY (SEQ ID NO: 198); and CDR3: AAAVAASAEFVTARS-NFYEY (SEQ ID NO: 199). FIG. 3 includes the VHH polypeptides containing framework regions (FRs), FR1, FR2, FR3 and FR4, the sequences of which are identified by SEQ ID NOs: as follows:

Figure 1A:
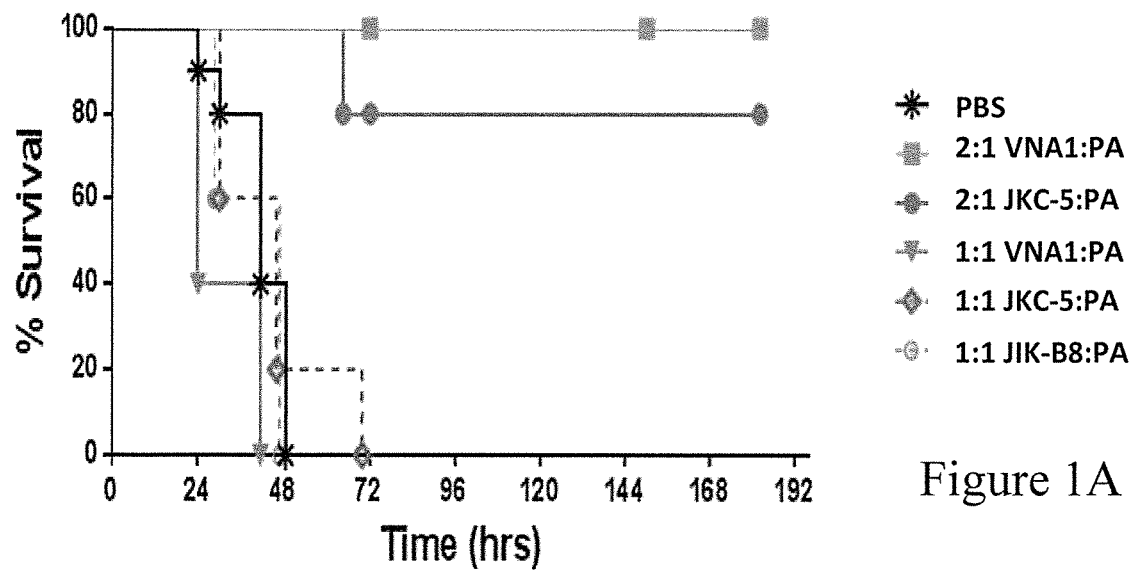
FIG. 1A-FIG. 1C are Meyer-Kaplan survival plots showing percent survival (% survival, ordinate) of subjects as a function of time in days (abscissa) following contact with LT and VHH binding/neutralizing agents as indicated. Balb/cJ mice were injected intravenously with antibody (Ab) at indicated molar ratios (Ab: toxin) 10 min prior to injection with LT (45 μg for each toxin component, IV).
Figure 1B:
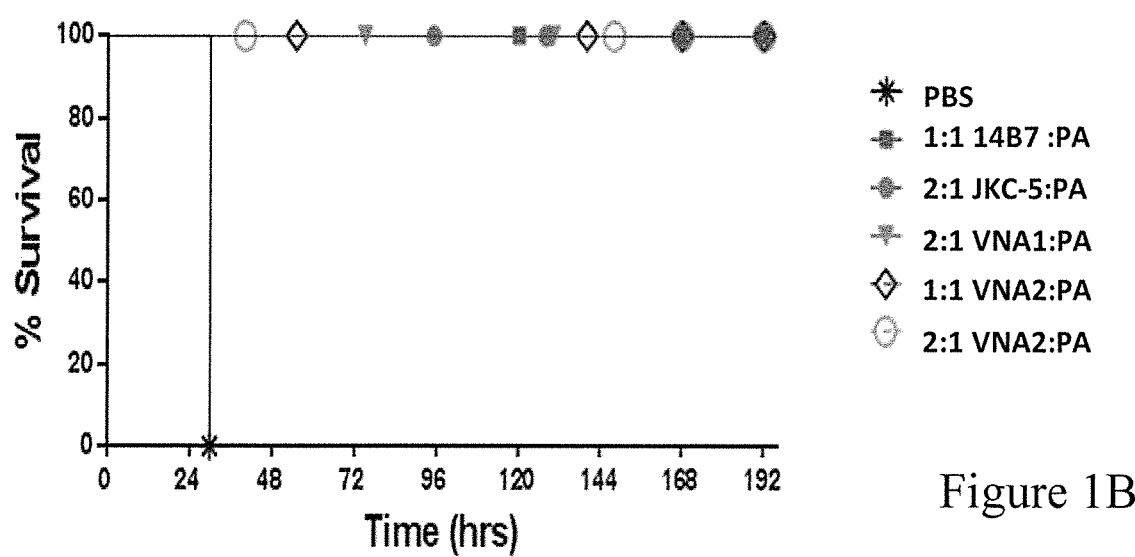

FRI
JIJ-B8 SGGG-LVQPGGSLSVSCA (SEQ ID NO: 207)
JIK-B8 SGGG-LVQPGGSLGLSCV (SEQ ID NO: 208)
JKH-A4 TGGG-LVQAGGSLRLSCS (SEQ ID NO: 209)
JKH-C7 SGGGGLVQAGGSLRLSCA (SEQ ID NO: 204)
JKH-D12 TGGG-LVQAGGTLRLSCA (SEQ ID NO: 210)
JKM-A6 TGGG-LVQPGGSLRLSCA (SEQ ID NO: 211)
JKO-A4 SGGG-SVQPGGSLRLSCA (SEQ ID NO: 212)
JKO-B8 SGGG-LVQPGGSLRLSCT (SEQ ID NO: 213)
JKO-E12 TGGG-LVQAGGSLRLSCL (SEQ ID NO: 214)
JKO-H2 SGGG-LVQAGGSLRLSCA (SEQ ID NO: 215);
FR2

JIJ-B8 AWYRQAPGKERELV (SEQ ID NO: 216)
JIK-B8 GWYRQAPGKQRELV (SEQ ID NO: 217)
JKH-A4 GWFRQAPGKEREFV (SEQ ID NO: 205)
JKH-C7 GWFRQAPGKEREFV (SEQ ID NO: 205)
JKH-D12 GWFRQEPGKEREFV (SEQ ID NO: 218)
JKM-A6 TWFRQAPGKEREAV (SEQ ID NO: 219)
JKO-A4 SWVRQAPGKGIEWV (SEQ ID NO: 220)
JKO-B8 DWYRQAPGKERELV (SEQ ID NO: 221)
JKO-E12 AWYRQAPGKQRERV (SEQ ID NO: 222)
JKO-H2 GWFRQAPGKEREFV (SEQ ID NO: 205);
FR3
JIJ-B8 YADSVTGRFTISRDNAKRTVYLQMNSLQPEDTAVYY (SEQ ID NO: 223)
JIK-B8 YADSVEGRFTISRDNVKKMVHLQVNSLKPEDTAVYY (SEQ ID NO: 224)
JKH-A4 YAEPLKGRFAISRDNDKNALYLQMNSLKPEDTAVYY (SEQ ID NO: 225)
JKH-C7 YGDSVKGRFTISRDTAKNTVYLQMNSLKPEDTAVYY (SEQ ID NO: 206)
JKH-D12 YADSVKGRFTISRDNAETTAYLQNSGLKPEDTAVYY (SEQ ID NO: 226)
JKM-A6 YSDSVKGRFTISRDNAQKTVYLQMNSLNPEDTAIYY (SEQ ID NO: 227)
JKO-A4 YADSVKGRFTISRDNARNTLYLQMNSLQPEDTAVYY (SEQ ID NO: 228)
JKO-B8 YADSVKGRFTISRDNAKKTVYLQMNGLKPEETAVYY (SEQ ID NO: 229)
JKO-E12 YTDSVEGRFTISRDNAKNTMYLQMNSLKPDDTAVYY (SEQ ID NO: 230)
JKO-H2 YADSVKGRFTISRDGTENTVYLQMNSLKPEDTAVYY (SEQ ID NO: 231);
FR4
JIJ-B8 GQGTQVTVSS (SEQ ID NO: 203)
JIK-B8 GQGTQVTVSS (SEQ ID NO: 203)
JKH-A4 GQGTQVTVSS (SEQ ID NO: 203)
JKH-C7 GQGTQVTVSS (SEQ ID NO: 203)
JKH-D12 GQGTQVTVSS (SEQ ID NO: 203)
JKM-A6 GQGTQVTVSS (SEQ ID NO: 203)
JKO-A4 GQGTQVTVSS (SEQ ID NO: 203)
JKO-B8 GQGTQVTVSS (SEQ ID NO: 203)
JKO-E12 GQGTQVTVSS (SEQ ID NO: 203)
JKO-H2 GQGTQVTVSS (SEQ ID NO: 203).

FIG. 4A and FIG. 4B are amino acid sequences of fusion proteins that contain partial translation products of the two VNAs SEQ ID NOs: 103 and 105. FIG. 4A (SEQ ID NO: 167) shows a fusion protein containing VNA1-PA (SEQ ID NO: 103), and FIG. 4B (SEQ ID NO: 168) shows a fusion protein containing VNA2-PA (SEQ ID NO: 105). The proteins are expressed in E. coli and tested as anthrax antitoxins. Proteins VNA1-PA (SEQ ID NO: 103) and VNA2-PA (SEQ ID NO: 105), respectively, are the same as previously named JKD-11 and JKU-1, respectively, in U.S. provisional application Ser. No. 62/089,949 filed Dec. 10, 2014. Both VNA fusion proteins shown in FIGS. 4A and 4B contain an amino terminal thioredoxin fusion partner and hexahistidine (SEQ ID NO: 169) encoded by the pET32b expression vector. In FIGS. 4A and 4B, the VHH sequences are flanked by E-tag peptides (underlined) and separated by the unstructured spacer ((GGGGS)$_3$) (SEQ ID NO: 145). The amino acid albumin-binding-peptide (ABP), DICLPRWGCLWED (SEQ ID NO: 146) described in Nguyen A, et al. (2006) Protein engineering, Design & Selection: PEDS 19: 291-297 is located at the carboxyl end of the fusion protein, separated from the second E-tag by a GGGGS (SEQ ID NO: 147) spacer.

FIG. 5A-FIG. 5D, respectively, are Meyer-Kaplan survival plots showing percent survival (% survival, ordinate) after BoNT/B toxin exposure of each of four amounts, respectively, subjects as a function of time in days (abscissa) following treatment with a 25 preparation of BoNT/B neutralizing VHH heterodimers as indicated. In FIG. 5A-FIG. 5D, an amount of BoNT/B, toxin of 10, 40, 100 and 500 LD50, respectively, was administered by intraperitoneal injection to groups of five C57BL/6J mice. The mice receiving the toxin were treated with 2 g of one of BoNT/B neutralizing VHH heterodimers (SEQ ID NO: 131, SEQ ID NO: 133, SEQ ID NO: 135, or SEQ ID NO: 137). Mice were monitored at least five times per day for survival and symptoms of botulism for seven days.

FIG. 6 is a table of the VHH names and binding properties. The first eleven VHHs were obtained by panning using PA83 bound to plastic, after which the $K_D$ values for these VHHs were assessed by SPR-PROTEON. The second group of nine VHHs were obtained by panning using 14B7-bound PA83, and the $K_D$ values were assessed by SPR-Biacore. The $K_D$ for JIK-B8, obtained as an internal reference for SPR-Biacore group, was observed to be 1±0.7. $EC_{50}$s were assessed by dilution ELISAs, and $IC_{50}$s were assessed by toxin neutralization assays on macrophages and competition groups (C-groups) by competition ELISA. N/A refers to antibodies that were observed to not neutralize toxin and thus have no measurable $IC_{50}$.

Figures 7A, 7B, 7C:
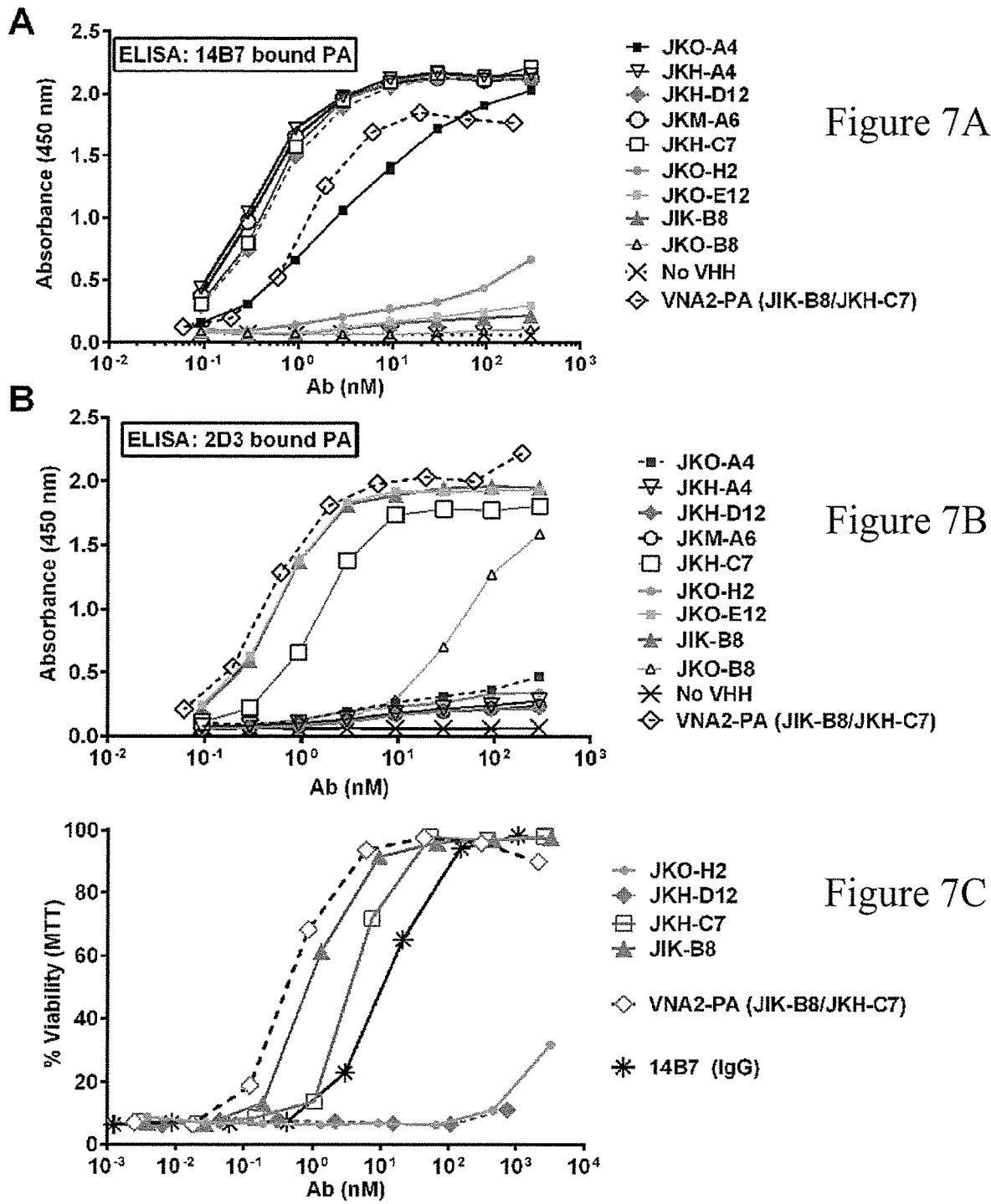

FIG. 7A-FIG. 7C are graphs showing the results of competition ELISAs and neutralization assays. Data in FIG. 7A and FIG. 7B were obtained using 14B7- or 2D3-captured PA which was bound to plates and an increasing concentration per plate of each VHH was then added and binding was assessed with an HRP-conjugated anti-Hisx6 or E-tag antibody using standard ELISA protocols. FIG. 7C shows representative neutralization assays for each of the four VHHs representing the four competition groups, a heteromultimer of two neutralizing VHHs, and mAb 14B7, with viability of the ordinate as a function of antibody concentration. All data were obtained from assays are representative of at least two separate repetitions.

DETAILED DESCRIPTION

Anthrax is a toxigenic disease, which rapidly progresses to lethality for the host if left untreated. The bioterrorist attacks utilizing Bacillus anthracis spores highlighted the need for cost-effective treatments that could be produced on a large scale if necessary. Almost all the therapeutics developed against the disease focus on the anthrax toxins, which have been demonstrated to be the primary virulence determinants. Examples herein describe a novel recombinant anti-toxin consisting of a heterodimer of two camelid anti-anthrax PA heavy chain VHH binding domains as an efficient therapeutic agent. A number of antibodies have been produced against the PA receptor-binding component of the tripartite toxin, and protection in animal models is demonstrated by data herein. Most antibodies target the same epitope of the toxin, which is the dominant neutralizing antigenic region, and only differ in varying affinities and clearance rates.

Anthrax disease is caused by a complex toxin that contains a protective antigen (PA), a lethal factor (LF) and an edema factor (EF). Recombinant engineered proteins as antibodies against PA are described herein which are protective against the disease. Heavy-chain-only Ab $V_H$ (VHH) domains with affinity for PA were obtained from immunized alpacas and were screened for anthrax neutralizing activity in macrophage toxicity assays.

Two classes of neutralizing VHHs were identified that recognized distinct and non-overlapping epitopes. One class of VHHs recognized were observed that domain 4 of PA at a neutralizing site that blocks PA binding to cells. Another class of VHHs recognized a novel, conformational epitope. A VHH antibody described herein was observed to inhibit conversion of the PA63 oligomer from "pre-pore" conformation to a SDS and heat-resistant "pore" conformation. The antibody described herein was observed to prevent endocytosis of cell surface generated PA63 subunit. The monomer neutralizing VHHs administered at 2:1 molar ratio to PA were observed to be effective in protecting mice from a lethal anthrax toxin challenge. The highest affinity members of different anti-PA VHH classes were expressed as two heterodimeric VHH-based neutralizing agents (VNAs). VNAs were observed to have improved neutralizing potency in cell assays and to have protected mice from anthrax toxin challenge with better efficacy than their corresponding monomer VHHs. The VNA2-PA (JKU-1) which was observed to be most efficient consists of a heterodimer of the novel oligomer-inhibiting VHH (JKH-C7) and a receptor blocking VHH (JIK-B8). This VNA2-PA was observed to protect mice against toxin challenge at 1:1 molar ratio to toxin and increased survival times were observed at submolar ratios. Furthermore, the antibody also provided protection against A35 spore challenge. VNA2-PA (JKU-1) has potential as an anthrax therapeutic, and its simple and stable nature is amenable to administration by genetic delivery or by respiratory routes.

The novel VHH-based VNA described herein consists of two anti-toxin VHHs targeting independent epitopes of PA and inhibiting the action of the toxin at two different functional steps. The VHH based VNA agent described herein is more effective in vivo by a factor of at least about 20-50 fold compared to the well-characterized neutralizing antibody 14B7 which acts on the same epitope as the approved human anti-PA antibody, RAXIBACUMAB (Abthrax) in protecting against anthrax toxin challenge and spore infection. The affinity is 0.07 nM in contrast to the 2.78 nM affinity of Abthrax, a commercially available monoclonal antibody, RAXIBACUMAB, that neutralizes toxins produced by *B. anthracis* (Human Genome Sciences, Rockville, Md.).

An antitoxin strategy herein uses VNAs consisting of two or more, linked, toxin neutralizing, VHHs recognizing non-overlapping epitopes on PA. An advantage of covalently linking VHHs together is a resulting increased toxin binding affinity and increase in potency of neutralization through targeting of two different steps in the interaction of the toxin with cells. A benefit of the conformational epitope of the VNA, JKH-C7 arm is the extremely low likelihood of easily circumventing the PA-antibody interaction through a small number of mutations in genes encoding PA. The bulk of previously available anti-PA neutralizing antibodies target the same receptor-binding epitope that the JIK-B8 arm of the VNA targets, and the receptor-binding epitope can be destroyed by genetic manipulation of the PA antigen to eliminate reactivity with these neutralizing antibodies. The complex conformational epitope for the JKH-C7 VHH arm of the antibody described herein is unlikely to be easily disrupted without impact on PA function.

The presence of toxins in the circulation causes a wide variety of human and animal illnesses. Antitoxins are therapeutic agents that prevent toxin infection or reduce further development of negative symptoms in patients that have been exposed to a toxin (a process referred to as "intoxication"). Typically, antitoxins are antisera obtained from large animals (e.g., sheep, horse, and pig) that were immunized with inactivated or non-functional toxin. More recently, antitoxin therapies have been developed using combinations of antitoxin monoclonal antibodies including yeast-displayed single-chain variable fragment antibodies generated from vaccinated humans or mice. See Nowakowski et al. 2002. Proc Natl Acad Sci USA 99: 11346-11350; Mukherjee et al. 2002. Infect Immun 70: 612-619; Mohamed et al. 2005 Infect Immun 73: 795-802; Walker, K. 2010 Interscience Conference on Antimicrobial Agents and Chemotherapy—50th Annual Meeting—Research on Promising New Agents: Part 1. IDrugs 13: 743-745. Antisera and monoclonal antibodies are difficult to produce economically at scale, usually requiring long development times and resulting in problematic quality control, shelf-life and safety issues. New therapeutic strategies to develop and prepare antitoxins are needed.

Antitoxins function through two key mechanisms, neutralization of toxin function and clearance of the toxin from the body. Toxin neutralization occurs through biochemical processes including inhibition of enzymatic activity and prevention of binding to cellular receptors. Antibody mediated serum clearance occurs subsequent to the binding of multiple antibodies to the target antigen (Daeron M. 1997 Annu Rev Immunol 15: 203-234; Davies et al. 2002 Arthritis Rheum 46: 1028-1038; Johansson et al. 1996 Hepatology 24: 169-175; and Lovdal et al. 2000 J Cell Sci 113 (Pt 18): 3255-3266). Multimeric antibody decoration of the target is necessary to permit binding to the Fc receptors which have only low affinity (Davies et al. 2002 Arthritis Rheum 46: 1028-1038 and Lovdal et al. 2000 J Cell Sci 113 (Pt 18): 3255-3266). Without being limited by any particular theory or mechanism of action, it is here envisioned that an ideal antitoxin therapeutic would both promote toxin neutralization to immediately block further toxin activity and would also accelerate toxin clearance to eliminate future pathology if neutralization becomes reversed.

Effective clearance of botulinum neurotoxin (BoNT), a National Institute of Allergy and Infectious Diseases (NIAID) Category A priority pathogen, is believed by some researchers to require three or more antibodies bound to the toxin. Nowakowski et al. 2002. Proc Natl Acad Sci USA 99: 11346-11350 determined that effective protection of mice against high dose challenge of BoNT serotype A (BoNT/A) requires co-administration of three antitoxin monoclonal antibodies, and that all three antibodies presumably promote clearance. Administration of a pool of three or more small binding agents, each produced with a common epitopic tag, reduced serum levels of a toxin when co-administered with an anti-tag monoclonal antibody (Shoemaker et al. U.S. published application 2010/0278830 A1 published Nov. 4, 2010 and Sepulveda et al. 2009 Infect Immun 78: 756-763, each of which is incorporated herein in its entirety). The tagged binding agents directed the binding of anti-tag monoclonal antibody to multiple sites on the toxin, thus indirectly decorating the toxin with antibody Fc domains and leading to clearance of the toxin through the liver.

Pools of scFv domain binding agents with specificity for BoNT/A and each containing a common epitopic tag (E-tag), had been shown to be effective for decorating the botulinum toxin with multiple anti-tag antibodies (Shoemaker et al. U.S. utility patent publication number 2010/0278830 published Nov. 4, 2010 and U.S. continuation-in-part patent publication number 2011/0129474 published Jun. 2, 2011, each of which is incorporated herein by reference in its entirety). Administration of binding agents and clearance antibodies to subjects resulted in clearance via the liver with an efficacy in mouse assays equivalent to conventional polyclonal antitoxin sera. Ibid. and Sepulveda et al. 2009 Infect Immun 78: 756-763. The tagged scFvs toxin targeting agents and the anti-tag monoclonal antibodies were effective to treat subjects at risk for or having been contacted with a disease agent.

The use of small binding agents to direct the decoration of toxin with antibody permits new strategies for the development of agents with improved therapeutic and commercial properties. Examples herein show that a single recombinant heterodimeric binding protein/agent which contains two or more high-affinity BoNT binding agents (camelid heavy-chain-only Ab VH (VHH) domains) and two epitopic tags, co-administered with an anti-tag mAb, protected subjects from negative symptoms and lethality caused by botulism. Further, the binding protein was observed to have antitoxin efficacy equivalent to and greater than conventional BoNT antitoxin serum in two different in vivo assays. Examples herein compare neutralizing or non-neutralizing binding agents administered with or without clearing antibody, and show the relative contributions of toxin neutralization and toxin clearance to antitoxin efficacy. Examples herein show that both toxin neutralization and toxin clearance contribute significantly to antitoxin efficacy in subjects. Toxin neutralization or toxin clearance using heterodimer binding protein antitoxins was observed herein to sufficiently protect subjects from BoNT lethality in a therapeutically relevant, post-intoxication assay. Methods in further Examples herein include an optional clearing antibody for example a monoclonal anti-E-tag antibody.

It was observed in Examples herein that VHH binding agents that neutralized toxin function significantly improved the antitoxin efficacy and even obviated the need for clearing antibody in a clinically relevant post-intoxication BoNT/A assay.

Pharmaceutical Compositions

An aspect of the present invention provides pharmaceutical compositions, wherein these compositions comprise an antigen from a toxin of *B. anthracis* or *C. botulinum* peptide or protein, and optionally further include an adjuvant, and optionally further include a pharmaceutically acceptable carrier. In various embodiments, the compositions include at least one atoxic protein or a source of expression of the protein, such that the protein elicits an immune response specific for a *B. anthracis* or *C. botulinum* toxin.

In certain embodiments, these compositions optionally further comprise one or more additional therapeutic agents. In certain embodiments, the additional therapeutic agent or agents are selected from the group consisting of antibiotics particularly antibacterial compounds, anti-viral compounds, anti-fungals, and include one or more of growth factors, anti-inflammatory agents, vasopressor agents, collagenase inhibitors, topical steroids, matrix metalloproteinase inhibitors, ascorbates, angiotensin II, angiotensin III, calreticulin, tetracyclines, fibronectin, collagen, thrombospondin, transforming growth factors (TGF), keratinocyte growth factor (KGF), fibroblast growth factor (FGF), insulin-like growth factors (IGF), epidermal growth factor (EGF), platelet derived growth factor (PDGF), neu differentiation factor (NDF), hepatocyte growth factor (HGF), and hyaluronic acid.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's The Science and Practice of Pharmacy Ed.* by LWW 21$^{st}$ EQ. PA, 2005 discloses various carriers used in formulating pharmaceutical compositions and known techniques for the preparation thereof. Carriers are selected to prolong dwell time for example following any route of administration, including IP, IV, subcutaneous, mucosal, sublingual, inhalation or other form of intranasal administration, or other route of administration.

Some examples of materials that can serve as pharmaceutically acceptable carriers include, but are not limited to, sugars such as glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, according to the methods of treatment of the present invention, the immunization is promoted by contacting the subject with a pharmaceutical composition, as described herein. Thus, the invention provides methods for immunization comprising administering a therapeutically effective amount of a pharmaceutical composition comprising active agents that include an immunogenic toxin protein of *B. anthracis* or *C. botulinum* to a subject in need thereof, in such amounts and for such time as is necessary to achieve the desired result. It will be appreciated that this encompasses administering an inventive vaccine as described herein, as a preventive or therapeutic measure to promote immunity to infection by *B. anthracis* or *C. botulinum*, to minimize complications associated with the slow development of immunity (especially in compromised patients such as those who are nutritionally challenged, or at risk patients such as the elderly or infants).

In certain embodiments of the present invention a "therapeutically effective amount" of the pharmaceutical composition is that amount effective for promoting production of antibodies and activity in serum specific for the toxins of *B. anthracis* or *C. botulinum*, or disappearance of disease symptoms, such as amount of antigen or toxin or bacterial cells in feces or in bodily fluids or in other secreted products. The compositions, according to the method of the present invention, may be administered using any amount and any route of administration effective for generating an antibody response. Thus, the expression "amount effective for promoting immunity", as used herein, refers to a sufficient amount of composition to result in antibody production or remediation of a disease symptom characteristic of infection by *B. anthracis* or *C. botulinum*.

The exact dosage is chosen by the individual physician in view of the patient to be treated. Dosage and administration are adjusted to provide sufficient levels of the active agent(s) or to maintain the desired effect. Additional factors which may be taken into account include the severity of the disease state; contact to infectious agent in the past or potential future contact; age, weight and gender of the patient; diet, time and frequency of administration; drug combinations;

reaction sensitivities; and tolerance/response to therapy. Long acting pharmaceutical compositions might be administered every three to four days, every week, or once every two weeks depending on half-life and clearance rate of the particular composition.

The active agents of the invention are preferably formulated in dosage unit form for ease of administration and uniformity of dosage. The expression "dosage unit form" as used herein refers to a physically discrete unit of active agent appropriate for one dose to be administered to the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, usually mice, rabbits, dogs, or pigs or piglets or other suitable animals. The animal models described herein including that of chronic or recurring infection by *B. anthracis* or *C. botulinum* is also used to achieve a desirable concentration range and route of administration. Such information can then be used to determine useful doses and routes for administration in humans.

A therapeutically effective dose refers to that amount of active agent which ameliorates at least one symptom or condition. Therapeutic efficacy and toxicity of active agents can be determined by standard pharmaceutical procedures in cell cultures or experimental animals, e.g., ED50 (the dose is therapeutically effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and from animal studies are used in formulating a range of dosage for human use.

The therapeutic dose shown in examples herein is at least about 1 g per kg, at least about 5, 10, 50, 100, 500 g per kg, at least about 1 mg/kg, 5, 10, 50 or 100 mg/kg body weight of the purified toxin vaccine per body weight of the subject, although the doses may be more or less depending on age, health status, history of prior infection, and immune status of the subject as would be known by one of skill in the art of immunization. Doses may be divided or unitary per day and may be administered once or repeated at appropriate intervals.

Administration of Pharmaceutical Compositions

After formulation with an appropriate pharmaceutically acceptable carrier in a desired dosage, the pharmaceutical compositions of this invention can be administered to humans and other mammals topically (as by powders, ointments, or drops), orally, rectally, mucosally, sublingually, parenterally, intracisternally, intravaginally, intraperitoneally, bucally, sublingually, ocularly, or intranasally, depending on preventive or therapeutic objectives and the severity and nature of a pre-existing infection.

In various embodiments of the invention herein, it was observed that high titers of antibodies, sufficient for protection against a lethal dose of *B. anthracis* or *C. botulinum* toxin, were produced after administration of the engineered atoxic toxin proteins provided herein. Liquid dosage forms for oral administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. Administration may be therapeutic or it may be prophylactic.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables. The injectable formulations can be sterilized prior to addition of spores, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral, mucosal or sublingual administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

Substantially Identical Amino Acid and Nucleotide Sequences for VHHs

There is a large body of information in the literature supporting the fact that closely related antibody (Ab) sequences are capable of performing the same binding and therapeutic functions such that this is now generally accepted by those with ordinary skill in immunological sciences and is even a dogma. The creation of Abs with small numbers of amino acid sequence variations occurs naturally within mammals and other some other animal species during the process of 'affinity maturation' in which cells producing Abs that bind a newly encountered antigen (Ag) are expanded such that progeny cells contain random mutations within portions of the Ab coding DNA that results in new, related Ab sequences. The cells expressing Abs that have gained improved binding properties for the new Ag are then selected and expanded, increasing the amount of the improved antibody in the animal. This process continues through multiple generations of mutation and selection until Abs with greatly improved binding properties result, thus providing, for example, better immunity against pathogens possessing the new Ag. This process of Ab affinity maturation is widely accepted in the literature and clearly demonstrates that related Ab amino acid sequences can possess similar target binding properties and perform similar therapeutic functions in vivo.

In examples herein, there are numerous examples of related Ab sequences performing similar functions and providing similar therapeutic benefits. The Abs described herein are mostly heavy-chain only Abs (HcAbs) from Camelids. The VH region from the DNA is isolated encoding these Abs and expressed as single-domain Abs called VHHs. Alpacas are immunized with a selected Ag multiple times to permit the animal to undergo affinity maturation of the HcAbs they produce recognizing this Ag. The HcAbs are then isolated and the DNA encoding the VHH regions are closed for expression of soluble VHHs that bind the Ag and have potential therapeutic or diagnostic properties. During this process, many examples of closely related VHHs are isolated presumably different which are intermediates resulting from the alpacas' affinity maturation process. These related VHHs are screened and most promising members of each homology group is identified, and becomes a lead candidate for further development.

VHHs, like all mammalian antibodies, consist of four well-conserved 'framework' regions (FRs) which are important to form the antibody structure. Between the FRs (FR1, FR2, FR3 and FR4) are three much less well-conserved 'complementarity determining regions' or CDRs which form the interactions with the Ags. These binding regions must bind to widely varying structures (epitopes) on different Ags, therefore, the CDRs must also vary widely so as to interact and bind to these Ags. The third CDR, CDR3, is generally the longest and most diverse of the CDRs within VHHs, both in size and sequence. CDR3 in VHHs can range in size from about 7 to about 28 amino acid residues [1]. The CDR3 regions of VHHs from the same alpacas selected for their binding to a common target Ag, prove to be very similar in their size and have many amino acid identities; the chance that this occurred by random chance are astronomical. Therefore, these VHHs resulted from affinity maturation of a common precursor VHH within the animal and are classified as being a 'homology group'. The individual VHHs within a homology group are classified for binding to a target the members of the VHH homology group 'compete' with each other for binding, thus demonstrating that they bind to the same region on the target.

Since the FRs are critical for sustaining the structure of the VHH and the positioning of the CDRs for binding to their target Ag, the FRs must not vary too much in sequence. Some variation, particular when replacement amino acids are related in properties, is permissible and these changes can often be found naturally within VHHs that have undergone affinity maturation in an animal. In addition to the FRs, the CDRs also must not vary too much in sequence or their Ag binding affinity will be compromised. An excellent way to estimate how much amino acid sequence variation is tolerated within VHHs without compromising their Ag binding character is to observe the variation that occurs naturally within affinity matured homology groups of VHHs isolated from the same animals and shown to bind to the same Ag.

An example of VHH sequence relatedness necessary to retain common Ag binding properties is described in U.S. Pat. No. 8,349,326, issued Jan. 8, 2014 and represented in FIG. 5. In this example, the substantial identity of five different VHH sequences shown in the patent, JDO-E9, JDQ-B2, JDQ-B5, JDQ-C5, and JDQ-F9 is represented as a phylogenic tree. These sequences are substantially different from each other and form a clear homology group when their sequences are compared to the sequences of seven random VHHs. All five members of this homology group had been selected for their binding to Botulinum neurotoxin serotype A (BoNT/A), all had clearly related CDR3 regions, and all were found to compete with each other for binding to BoNT/A. Therefore, these sequences had a common binding site. Despite their common clonal origin and common Ag binding sites, these VHHs of 108 amino acid length contained as many as 26 amino acid differences. This implied that VHHs containing up to 24% amino acid sequence variation had retained their ability to bind to the same region of BoNT/A.

Another example that describes acceptable amount of VHH sequence variation within related VHHs having the same Ag binding character is described in Tremblay et al., 2013 Infect Immun 81: 4592-4603. Proteins in large homology group are described containing 11 VHH sequences, Stx-A3, A4, A5, D4, F1, G6, H3, H5, H9, H10, and H12 with closely related CDR3 sequences of identical size, and the unusual property of cross-specific binding to two different Shiga toxins, Stx1 and Stx2. Two of the more distantly related members of this homology group, VHHs Stx-A4, Stx-A5 are characterized as having common Ag binding character. These two related VHHs have 32 amino acid changes in their full 120 or 121 residue VHH sequence. Therefore, 26% amino acid variation in sequence does not result in the loss of their common Ag binding property.

A portion of the data herein was published as follows, "Prolonged prophylactic protection from botulism with a single adenovirus treatment promoting serum expression of a VHH-based antitoxin protein" by co-authors Mukherjee J, Dmitriev I, Debatis M, Tremblay JM, Beamer G, Kashentseva E A, Curiel D T, Shoemaker C B, in the journal PLoS ONE 9(8): e106422 2014 Aug. doi:10.1371/journal.pone.0106422; "Adenovirus vector expressing Stx1/2-neutralizing agent protects piglets infected with *E. coli* O157: H7 against fatal systemic intoxication" by co-authors Sheoran A S, Dmitriev I P, Kashentseva E A, Cohen O, Mukherjee J, Debatis M, Shearer J, Tremblay J M, Beamer G, Curiel D T, Shoemaker C B, Tzipori S, in the journal Infect Immun. 2014 Nov. 3. pii: IAI.02360-14; and "A heterodimer of a VHH (variable domains of camelid heavy chain-only) antibody that inhibits anthrax toxin cell binding linked to a VHH antibody that blocks oligomer formation is highly protective in an anthrax spore challenge model" by co-authors Moayeri M, Leysath C E, Tremblay J M, Vrentas C, Crown D, Leppla S H, Shoemaker C B, in the journal J Biol Chem. 2015 Mar. 6; 290(10):6584-95 which appeared online Jan. 6, 2015. These papers are hereby incorporated in their entireties herein.

The invention now having been fully described, it is further exemplified by the following claims.

EXAMPLES

Example 1: Toxins and Spores

Endotoxin-free mutant PA proteins, including wild type PA83, PA63, and LF were purified from *B. anthracis* as described in Park, S., et al., 2000 Protein expression and purification 18, 293-302. The PAΔΔ is a mutant from which amino acid residues at positions 162-167 and 304-317 of the amino acid sequences have been genetically deleted, such that the protein cannot be cleaved by furin and accumulates on the cell surface. PAdFF is a mutant in which phenylalanine residues at positions 313 and 314 have been deleted thereby making the protein unable to translocate LF and EF (Singh, Y., et al., 1994 The Journal of biological chemistry 269, 29039-29046). Concentrations of LT correspond to the concentration of each toxin component (i.e. 1 µg/mL LT is 1 µg/mL PA+1 µg/mL LF). Spores of the non-encapsulated, toxigenic Sterne-like strain A35 (Pomerantsev, A. P., et al., 2006 Infection and immunity 74, 682-693) used to infect mice were prepared as described in Moayeri, M., et al., 2010 PLoS pathogens 6, e1001222.

Example 2: Reagents

Rabbit anti-PA83 polyclonal serum #5308 and neutralizing anti-PA mouse monoclonal antibody (mAb) 14B7, which blocks binding of PA (both PA83 and PA63) to its cellular receptors was manufactured as described in Rosovitz, M. J., et al., 2003 The Journal of biological chemistry 278, 30936-30944. Antibodies against the N-terminus of MEK1 (Calbiochem-EMD Biosciences, San Diego, Calif.), horse radish peroxidase (HRP)-conjugated and non-conjugated anti-E-tag polyclonal antibodies (Bethyl Labs, Montgomery, Tex.) and various IR-dye tagged secondary antibodies (Rockland Labs, Boyertown, Pa.) were purchased. The dye 3-(4,5-dimethyl-2-thiazolyl)-2,5-diphenyl tetrazolium bromide (MTT) was purchased from Sigma (St. Louis, Mo.).

Example 3: VHH-Display Library Preparation from Genes Expressed in Immunized Alpacas Three alpacas were immunized with PA83 (100 µg) by five successive multi-site subcutaneous (SC) injections at three week intervals. For the first immunization, the adjuvant was alum/CpG and subsequent immunizations used alum. All alpacas achieved ELISA anti-PA titers of 1:1,000, 000. Blood was obtained from the alpacas for lymphocyte preparation seven days after the fifth immunization, and RNA was extracted using the RNEASY kit (Qiagen, Valencia, Calif.). Two VHH-display phage libraries were prepared as described in Maass, D. R., et al., 2007 International journal for parasitology 37, 953-962 and Tremblay, J. M., et al., 2010 Toxicon 56, 990-998. The forward and reverse primers used to amplify the VHH coding region repertoire contained Not1 and Asc1 sites, which were used to ligate the JSC vector for gene III phage display. The first library (JIG-2) was constructed using RNA obtained from peripheral blood lymphocytes (PBLs) of one immunized alpaca and contained about $1 \times 10^7$ independent clones, and the second library (JKF-1) was generated from RNA obtained from a pool of PBLs of the other two alpacas, and contained about $3 \times 10^7$ independent clones.

Example 4: ELISAs

Purified VHH preparations were serially diluted onto ELISA plates coated with 1 µg/ml of each of the different PA proteins, incubated for one hour at room temperature, washed and then incubated for one hour with HRP-anti-E-tag. Bound HRP was detected using 3,3',5,5'-tetramethylbenzidine (Sigma) and values were plotted as a function of the input VHH concentration. $EC_{50}$ values were calculated for the VHH concentration that secreted in a signal equal to 50% of the maximum signal.

Example 5: Anti-PA VHH Identification and Preparation

Phage library panning, phage recovery and clone fingerprinting were performed as described in Mukherjee, J., et al., 2012 PLoS ONE 7, e29941, Maass, D. R., et al., 2007 International journal for parasitology 37, 953-962 and Tremblay, J. M., et al., 2010 Toxicon 56, 990-998, as follows. The first panning process utilized the JIG-2 VHH-display library and employed purified PA83 or PA63 coated onto Nunc Immunotubes at 10 µg/ml for the first low stringency pan and 1 µg/ml for the second high stringency pan. After two panning cycles, 70% of random clones selected on each target produced a signal two-fold greater than background. The clones that produced strongest 'bug supernatant' ELISA (Tremblay, J. M., et al., 2013 Infection and immunity 81, 4592-4603) signals on plates coated with 0.5 µg/ml PA83 were fingerprinted. The VHHs that had been panned on PA83 or PA63 were observed to recognize both PA83 and PA63. VHH coding sequences were determined for 24 clones displaying clear unique fingerprints (Tremblay, J. M., et al., 2013 Infection and immunity 81, 4592-4603). Sequence alignments showed 11 distinct homology groups. Amino acid sequences of clones representing each group are shown in FIG. 3. A second panning process using the JKF-1 library was performed similar to the first panning process and PA83 was used as the target. About 300 colonies were picked randomly and screened by bug supernatant ELISA on replica plates coated with either 0.5 µg/ml PA, or 3 µg/ml 14B7 mAb (Little, S. F., et al., 1988 Infection and immunity 56, 1807-1813) followed by 1 µg/ml PA83. Screening on 14B7-captured PA83 was performed to block binding of VHHs recognizing the dominant epitope (C-group 1, FIG. 6) that was identified following the screening of the first library. About 70% of clones recognized PA83 and about 20% recognized 14B7-captured PA83. From data obtained by ELISA and DNA fingerprinting, about 70 different VHH coding sequences were obtained. The alignment of these 70 different VHH coding sequences led to the identification of eight new homology groups not previously identified in the first screen (VHHs: JKH-A4, JKH-C7, JKH-D12, JKM-A6, JKO-A4, JKO-B8, JKO-E12, AND JKO-H12 in FIGS. 3 and 6). At least one VHH from each homology group was selected for protein expression. Expression and purification of VHHs in *E. coli* as recombinant thioredoxin (Trx) fusion proteins containing hexahistidine (SEQ ID NO: 169) was performed as previously described in Tremblay, J. M., et al., 2010 Toxicon 56, 990-998. VHH heterodimers were genetically engineered to be linked by a 15-amino acid flexible spacer ((GGGGS)$_3$) (SEQ ID NO: 145). All VHHs were expressed with a carboxyl-terminal E-tag epitope. Competition ELISA analysis was performed as previously described, with minor modifications (Mukherjee, J., et al., 2012 PLoS ONE 7, e29941).

Example 6: Affinity Analyses

The kinetic parameters of the VHHs were assessed by performing surface plasmon resonance, using either a PROTEON XPR36 Protein Interaction Array System (Bio-Rad, Hercules, Calif.; VHHs: JHD-B6, JHE-D9, JIJ-A12, JIJ-B8, JIJ-D3, JI-E9, JIJ-F11, JIK-B8, JIK-B10, JIK-B12, and JIK-F4 in FIG. 6) or a BIACORE 3000 (GE Healthcare; VHHs: JKH-A4, JKH-C7, JKH-D12, JKM-A6, JKO-A4, JKO-B8, JKO-E12, and JKO-H12 in FIG. 6). In each assay, the VHH was immobilized to the chip (GLH for PROTEON, CM5 for BIACORE) by amine coupling chemistry, involving sequential activation of the chip surface with a mixture of 1-ethyl-3-(3-dimethylaminopropyl)carbodiimide (EDC) and sulfo-N-hydoxysuccinimide (sulfo-NHS), injection of PA83 at pH 5 (sodium acetate buffer), and deactivation with an ethanolamine injection.

For the PROTEON data set, a range of PA concentrations was passed over the chip surface at 100 µL/min for 60 s, and dissociation was recorded for 600 s or 1200 s. Running buffer for these assays was 10 mM Hepes, pH 7.4, 150 mM NaCl, 0.005% Tween-20. The surface was regenerated between runs with a 30 s injection of 50 mM HCl at 50 µL/min. Data were evaluated with PROTEON Manager software (version 3.1.0.6) using the Langmuir interaction model to obtain $K_D$ values. Reported values are the mean of at least four replicates.

For the BIACORE data set, VHHs were passed over the PA immobilized on the chip surface at 100 nM and 100 µl/min for 60 s, and dissociation was recorded for 600 s or 1200 s. Running buffer for these assays was 10 mM HEPES, pH 7.4, 150 mM NaCl, 0.005% Tween-20. The surface was regenerated between runs with a 30 s injection of 10 mM glycine (pH 3) at 50 µl/min. Dissociation and association phases of each curve were fit separately using BIAevaluation software (GE) using the 1:1 Langmuir model to obtain $K_D$ values. Reported values are the mean of three replicates. A series of four replicates at 100 nM through 2 µM JKO-B8 resulted in comparable $K_D$ values at each concentration. A negative control VHH (anti-EF) did not exhibit any binding to the PA-coated chip. JIK-B8 was run at the beginning and end of the series to provide a point of comparison to the PROTEON data set.

Example 7: Toxicity and Neutralization Assays

RAW264.7 mouse macrophages were grown in Dulbecco's modified Eagle medium (DMEM) supplemented with 10% fetal bovine serum, 10 mM HEPES, and 50 µg/mL gentamicin (all purchased from Life Technologies, Grand Island, N.Y.). For neutralization assays PA83 and LF (250 ng/ml) in serum-free Dulbecco's Modified Eagle Medium were incubated with each of various dilutions of antibody in 96-well plates for one hour prior to addition to RAW264.7 macrophages. Viability was assessed by MTT staining as described in Chen, Z., et al., 2009 Infection and immunity 77, 3902-3908, at a time point when greater than 90% of toxin-treated controls were observed to be lysed by assessment by light microscopy. In certain experiments PA83 or PA63 (1 µg/ml) were pre-bound to antibodies or were added to cells at 37° C. or 4° C. followed after one hour by washing with serum-free DMEM at the same temperature and addition of medium containing LF or antibodies prepared in LF (1 µg/ml). Cells were then incubated at 37° C. for 12-16 hours. Viability was then assessed by MTT staining relative to untreated cell controls.

Example 8: Mouse Studies

For toxin challenge, Balb/cJ mice (female, 8 weeks old, Jackson Laboratories, Bar Harbor, Me.) were treated with antibody agents by the IV route at the doses (molar ratios relative to PA) and times described in brief description of the figures. Mice were challenged with LT (45 g, IV) and monitored for 10 days for survival. For spore challenges, C57BL/6J mice (8 weeks old, female, Jackson Laboratories) were challenged with the lethal dose of 2×10$^7$ spores (SC, 200 µl) before or after antibody administration (SC) at various doses and times as noted in brief description of the figures.

Example 9: Ethics Statement

All examples were performed under protocols approved by Tufts University and National Institute of Allergy and Infectious Diseases (NIAID) Animal Care and Use Committees. Work with alpacas was performed at Tufts under approved protocol Tuskegee University School of Veterinary Medicine (TUSVM) and Institutional Animal Care and Use Committee (IACUC) Protocol #G2011-08. Mouse studies were performed at NIAID under approved protocols LPD8E and LPD9E.

Example 10: Anthrax PA-Binding VHHs

VHH-display phage libraries were prepared from genetic material obtained from three alpacas, which had been immunized with purified anthrax PA83. Two separate libraries were selected for clones binding to PA83 or, to PA83 immobilized on mAb 14B7. The mAb 14B7 is a well-characterized neutralizing mAb that binds to an immunodominant epitope through which PA binds to its receptor.

Of total clones obtained and sequenced, 19 VHHs with apparently unrelated sequences were identified (FIG. 3). Competition assays between the various VHHs, and with 14B7 and 2D3 mAbs, which bind distinct immunodominant regions of PA83 (Little, S. F., et al., 1988 Infection and immunity 56, 1807-1813) showed that the identified VHHs fall into four distinct competition groups (identified as 1, 2, 3, and 4 in FIG. 6) and thus likely each protein in a group binds to one of four non-overlapping epitopes on PA. Ten of the 11 VHHs selected by binding to PA83-coated tubes (VHHs: JHD-B6, JHE-D9, JIJ-A12, JIJ-B8, JIJ-D3, JIJ-E9, JI-F11, JIK-B8, JIK-B10, JIK-B12, and JIK-F4 in FIG. 6) competed with 14B7. Eight unique PA-binding VHHs, including six that bind PA83 at sites different than 14B7 (FIG. 7A and FIG. 7B) were subsequently selected by binding to 14B7-immobilized (and thereby blocked) PA (VHHs: JKH-A4, JKH-C7, JKH-D12, JKM-A6, JKO-A4, JKO-B8, JKO-E12, and JKO-H12 in FIG. 6). Binding of one of the VHH, clone JIJ-B8 was not blocked by either mAb, and binding of another clone JKO-H2 was inhibited by both mAbs (FIG. 7A and FIG. 7B). The VHHs were characterized for PA affinity by dilution ELISA (for $EC_{50}$) and by surface plasmon resonance (for $K_D$) (FIG. 6). A selected VHH representative of each of the four epitope competition groups is illustrated by a shaded portion in FIG. 6. These are JIK-B8 (C-group 1), JKH-C7 (C-group 3), JKH-D12 (C-group 2), and JKO-H2 (C-group 4).

Example 11: Anthrax Toxin Neutralization

Cell-based anthrax toxin neutralization assays were performed on each of the 19 unique VHHs, and the data showed potencies ranging from $IC_{50}$ of about 200 μM to no activity in an assay using PA at 1.25 nM (FIG. 6; representative assay with antibodies from each competition group shown in FIG. 7C). VHHs recognizing the immunodominant PA domain (group 1) differed widely in their ability to neutralize the toxin, with four of 12 showing no neutralizing ability. VHHs JIK-B8 and JKO-E12 of the C-group 1 class displayed the highest affinity and lowest $IC_{50}$ values. One VHH recognized a second epitope (JKH-C7, group 3, FIG. 6) showed potent anthrax neutralizing activity (FIG. 7C). VHHs that had been characterized as recognizing C-group 2 and C-group 4 showed weak or undetectable toxin neutralizing activity (FIG. 7C). VHH JKO-H2 (group 4) displayed no recognition of PA63, suggesting that furin cleavage either removes the epitope or alters it in a manner that it cannot be recognized.

Example 12: Heterodimeric VHH-Based Neutralizing Agents (VNAs) Protect Against Anthrax Toxin and Spore Infection in Mice Linking toxin-neutralizing VHHs into heteromultimeric VNAs has been found to improve toxin affinity and, more importantly, to substantially improve in vivo antitoxin efficacy (Mukherjee, J., et al., 2012 PLoS ONE 7, e29941; Tremblay, J. M., et al., 2013 Infection and immunity 81, 4592-460; Vance, D. J., et al., 2013 The Journal of biological chemistry 288, 36538-36547; Yang, Z., et al., 2014 The Journal of infectious diseases 2014 Sep. 15; 210(6):964-72).

Figure 1C:
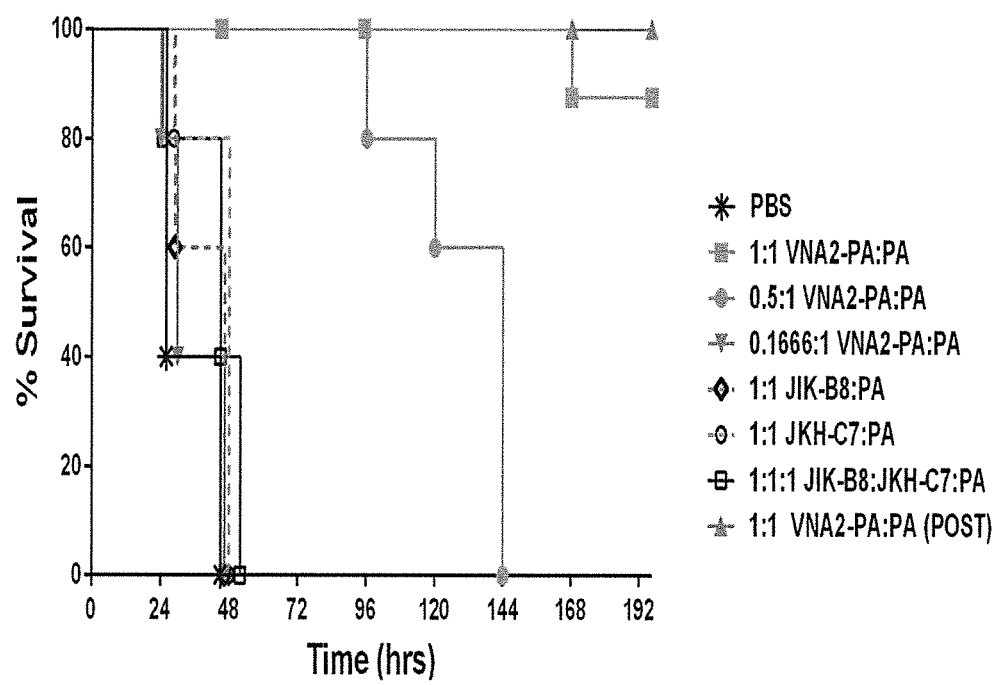
Figure 2A:
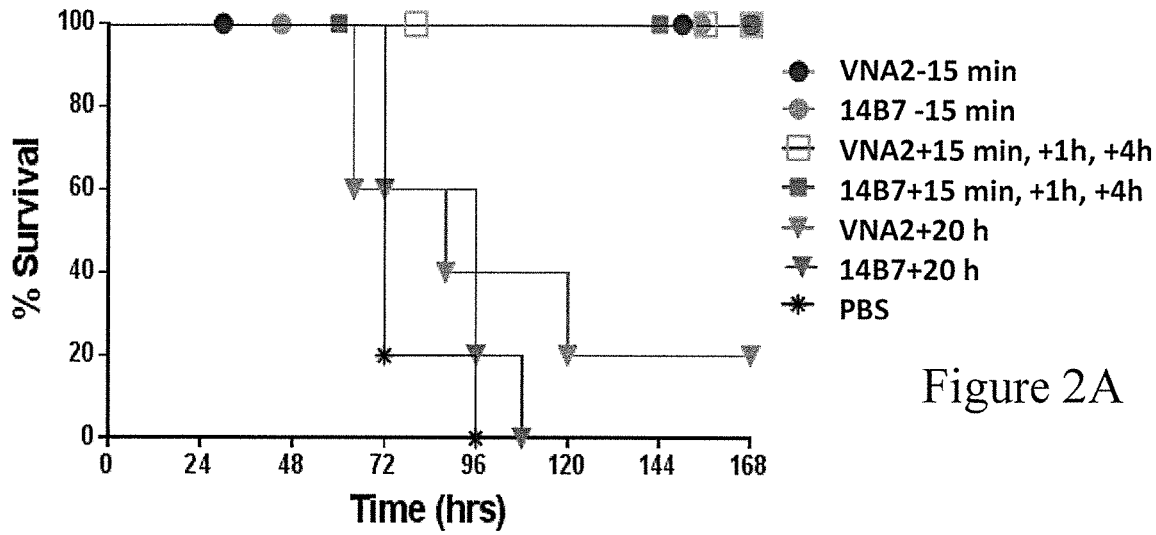
FIG. 2A and FIG. 2D are Meyer-Kaplan survival plots showing percent survival (% survival, ordinate) of subjects as a function of time in days (abscissa) following contact with A35 Sterne-like toxigenic *B. anthracis* strain spores ($2\times10^7$ spores, SC) and VHH binding/neutralizing agents.
Figure 2B:
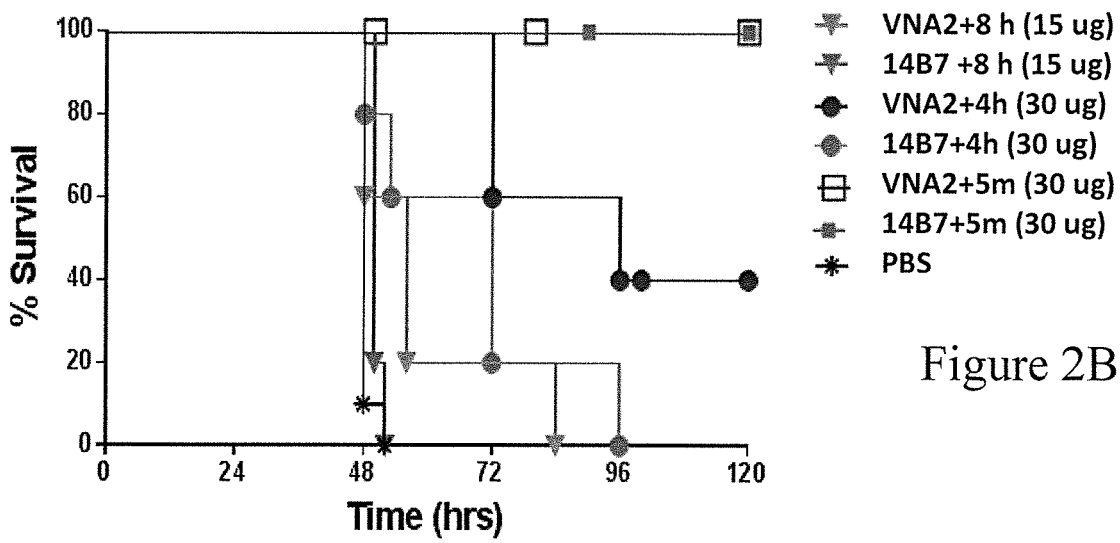
FIG. 2B shows data obtained after antibody was administered post-infection at indicated times and doses. Control mice were treated with PBS at 15 min, 1 hour and 4 hours post infection.
Figure 2C:
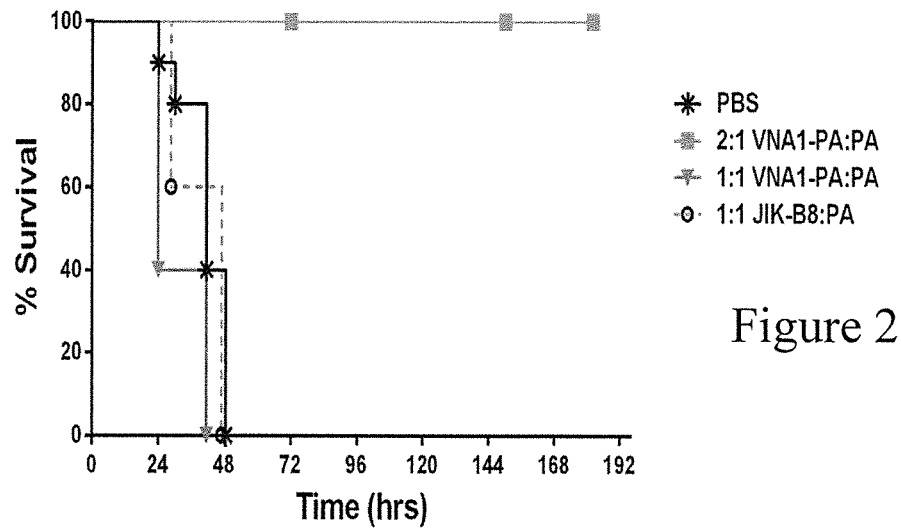
FIG. 2C contains data from Balb/cJ mice injected intravenously (IV) with antibody at indicated molar ratios (Ab:toxin) 10 minutes prior to injection with LT (45 μg for each toxin component). Control groups received PBS instead of antibody. Animals were monitored for 10 days post treatment for signs of malaise and survival.
Figure 2D:
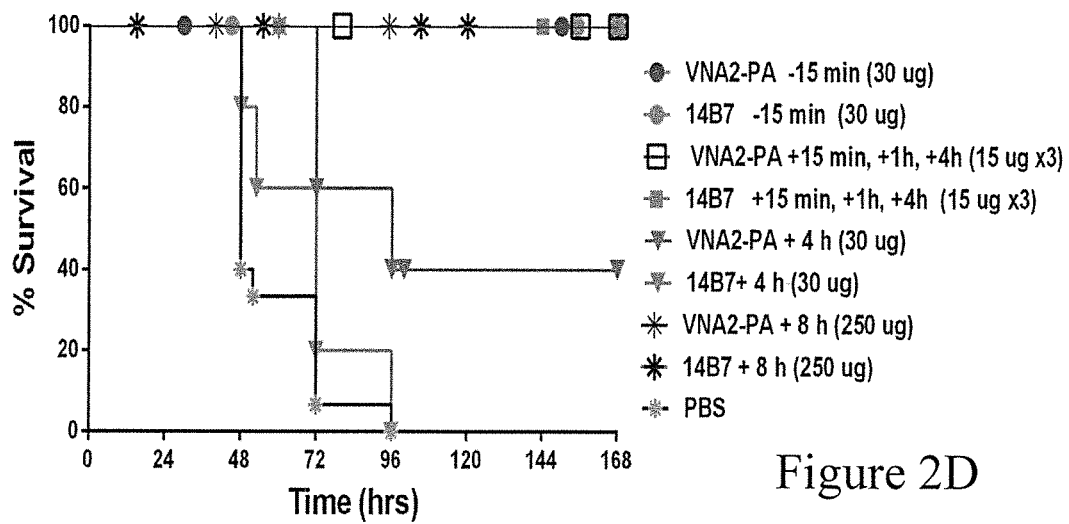

A heterodimeric VNA (VNA2-PA) was prepared to contain the two, potent neutralizing VHHs, JIK-B8 and JKH-C7, separated by a short unstructured peptide, was expressed and purified (amino acid sequence shown in FIG. 4A). This construct VNA2-PA, was observed to have potent neutralizing toxin activity (FIG. 7C). VNA2-PA was compared to monomeric VHHs for the ability to protect mice from anthrax toxin. The toxin dose between 1-2 LD100 (45 μg LT) was administered by IV route for the Balb/cJ strain. Treatment doses were selected to test efficacy at various molar ratios of agent to toxin. Heterodimeric VNAs each bind at two separate sites on each toxin, so a dose that can fully occupy both binding sites must be present at a 2:1 molar ratio agent:toxin. Each single monomer VHH was observed as not able to protect mice or provide any beneficial effect at a 1:1 molar ratio, with percent survivals as low as that for mice administered control PBS. The heterodimeric VNA2-PA in contrast was highly protective at 1:1 (FIG. 1C) yielding 100% protection for the entire time course. Thus, VNA2-PA was able to shift the time to death significantly even at submolar ratios to toxin. Importantly, the heterodimer offered greater protection against toxin than a pool of the two VHHs used in a 1:1:1 ratio with toxin, providing evidence of the improved in vivo efficacy of the heterodimer form (FIG. 1C). VNA2-PA treatment two hour post-toxin administration was also highly protective (FIG. 1C). This finding was surprising in light of the fact that the bulk of PA has been shown to be cleaved to PA63 and removed from circulation by two hours after a bolus administration (Moayeri, M., et al., 2007 Infection and immunity 75, 5175-5184). Thus, it is here envisioned that a significant amount of active PA not measurable in circulation (plasma) may remain accessible to antibody at crucial tissue sites. A second VHH heterodimer engineered by the methods herein, VNA1-PA, incorporating as component monomers the neutralizing JIK-B8 VHH with a non-neutralizing VHH (JIJ-B8) was observed to fail to provide any protection if administered 1:1, but was fully protective in this assay if administered at a two-fold molar excess (FIG. 4B and FIG. 2C).

VNA2-PA was tested with 14B7 mAb control for protection of C57BL/6J mice against infection with a single LD100 dose of the A35 Sterne-like toxigenic B. anthracis strain. Antibody provided 15 min prior to subcutaneous spore infection or at three sequential times of dosing, at 15, 60 and 240 min post-infection, was also fully protective (FIG. 2A-FIG. 2D).

A single administration of the VNA2-PA antibody at the lower dose of 30 μg at four hours post infection resulted in survival of 2/5 mice. Mice treated with this dose of 14B7 died during the time course, likely because only one third the number of antibody molecules were present compared to VNA2-PA. Increasing the time gap between spore infection and antibody administration to eight hours resulted in a complete loss of protection unless antibody was increased to a much higher dose of 250 μg, at which dose a surprising full protection of the entire mouse group was observed (FIG. 2A-FIG. 2D).

Example 13: Heterodimeric VHH-Based Neutralizing Agents (VNAs) Protect Against BoNT/B Toxin in Mice BoNT/B neutralizing heterodimer VHHs were tested for the ability to protect mice from BoNT/B lethality. An amount of BoNT/B toxin of 10, 40, 100 and 500 LD50 respectively was administered by intraperitoneal injection to groups of five C57BL/6J mice. The mice receiving the toxin were treated with 2 g of one of BoNT/B neutralizing VHH heterodimers (SEQ ID NO: 131, SEQ ID NO: 133, SEQ ID NO: 135, or SEQ ID NO: 137). Mice were monitored at least five times per day for survival and symptoms of botulism for seven days.

Figure 5A:
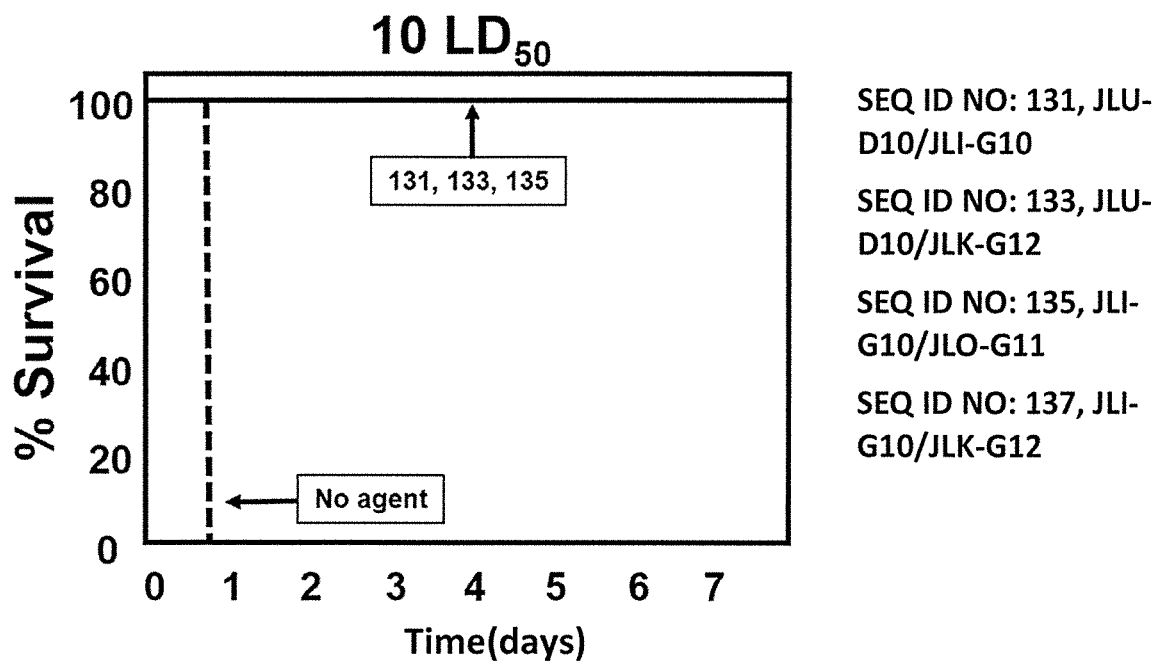
Figure 5B:
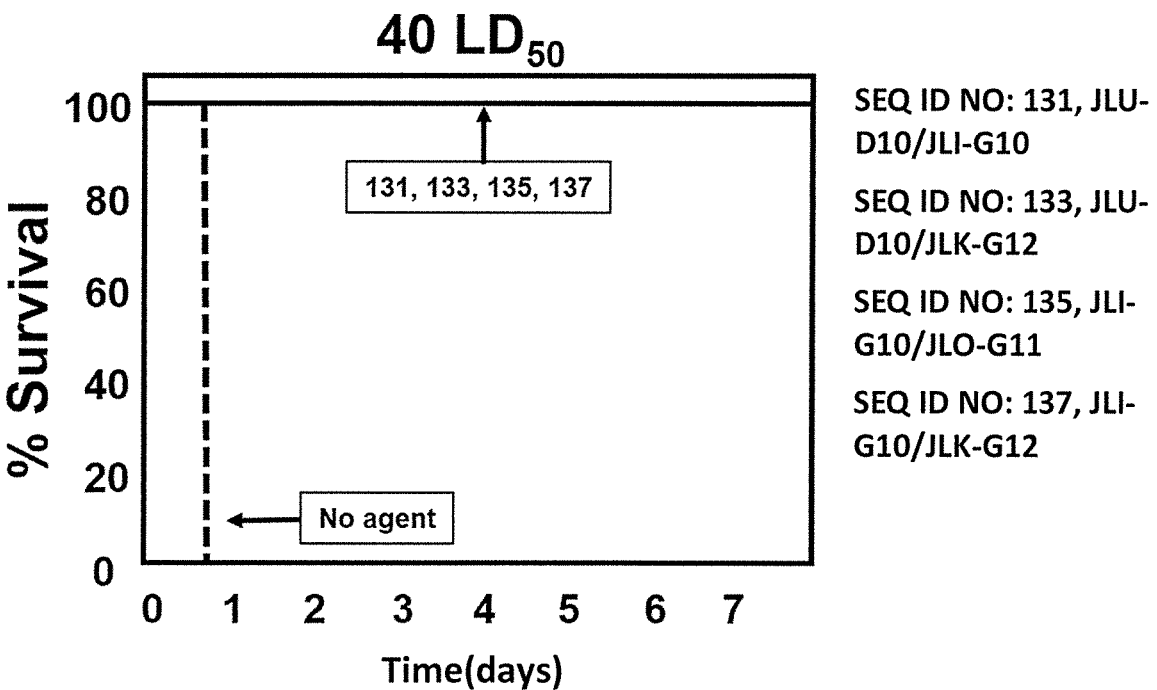
Figure 5C:
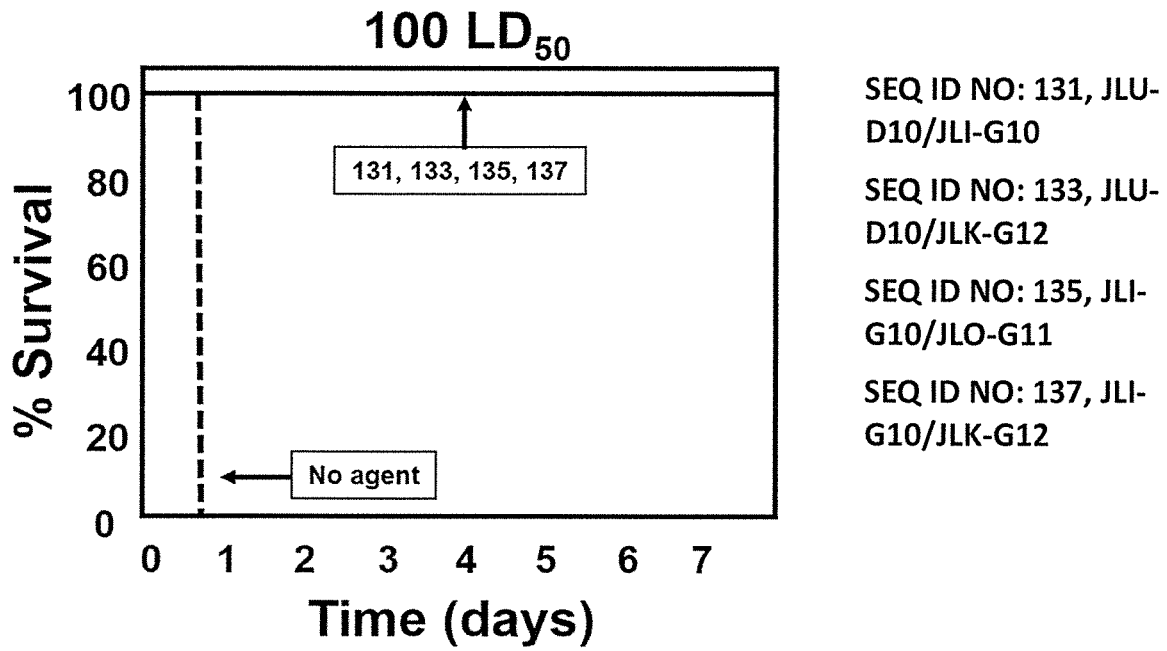

Mice contacted with BoNT/B toxin of 10, 40 and 100 LD50 respectively by intraperitoneal injection were treated with 2 g of one of BoNT/B neutralizing VHH heterodimers SEQ ID NO: 131, SEQ ID NO: 133, SEQ ID NO: 135, or SEQ ID NO: 137. It was observed that the treated mice were fully protected, having a survival rate of 100%. In contrast, control mice untreated with VHH heterodimers died within 24 hours as shown in FIG. 5A-FIG. 5C.

Figure 5D:
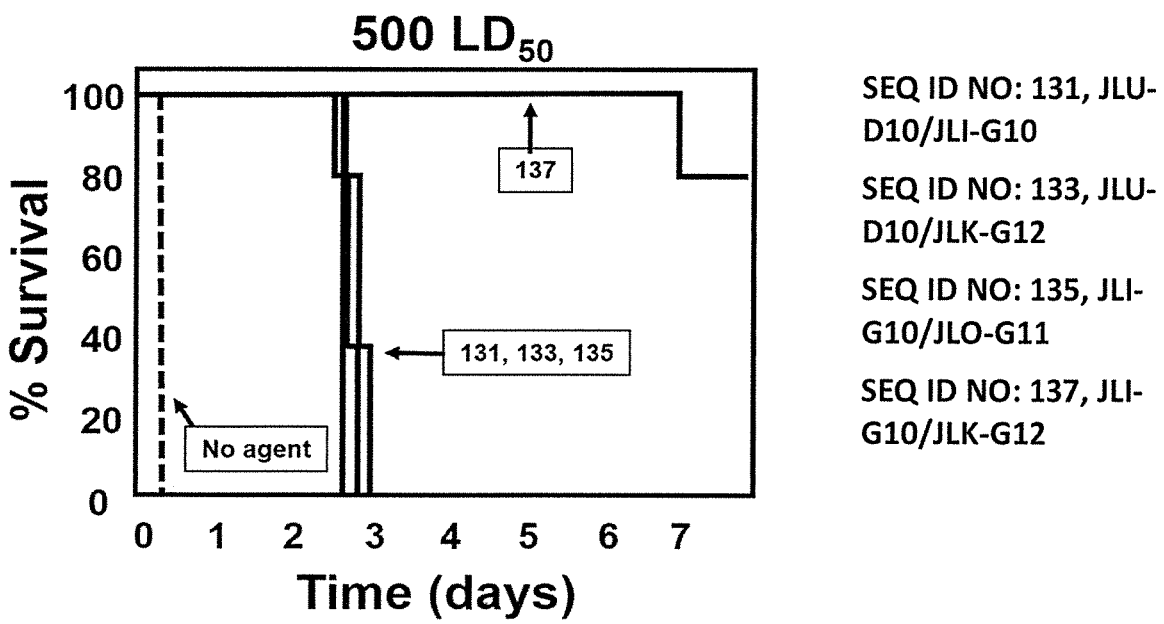

At the even greater BoNT/B toxin concentration of 500 LD50, VHH heterodimers SEQ ID NO: 131, SEQ ID NO: 133 and SEQ ID NO: 135 provided protection for two days and VHH heterodimer SEQ ID NO: 137 showed 100% survival rate till day 7 and 80% survival rate thereafter (FIG. 5D).

APPENDICES OF TOXIN-BINDING VHH PROTEINS AND ENCODING NUCLEIC ACIDS

Appendix B

Anthrax Protective Antigen (PA) Positive VHHs
Included in Appendix B are the following: 8 anthrax protective antigen (PA)-binding VHHs; 16 BoNT/B-binding VHHs; and 12 BoNT/E-binding VHHs:

JKH-A4, SEQ ID NO: 1
QVQLAETGG-GLVQAGGSLRLSCSASGLTFGNYAMGWFRQAP GKEREFVASISRSGSN TWYAEPLKGRFAIS-RDNDKNALYLQMNSLKPEDTAVYYCAGGSYN-SDWWNYMYWGQG TQVTVSSEPKTPKPQ

SEQ ID NO: 2
CAGGTGCAGCTGGCGGAGACGGGGGGAGGAT-TGGTGCAGGCTGGGGGCTCGCTGAGA CTCTCCTGTTCAGCCTCTGGGCTCACCTTCGG-GAACTATGCCATGGGCTGGTTCCGC CAGGCTCCAGGGAAGGAGCGTGAGTTTGTAG-CATCTATTTCTCGGAGTGGTAGTAAC ACATGGTATGCAGAACCCCTGAAGGGCCGAT-TCGCCATCTCCAGAGACAACGACAAG AACGCGCTCTATCTGCAAATGAACAGCCT-GAAACCTGAGGACACGGCCGTTTATTAC TGTGCTGGAGGATCTTATAATAGTGACTGGTG-GAACTATATGTACTGGGGCCAGGGG ACCCAGGTCACTGTCTCCTCAGAACCCAA-GACACCAAAACCACAA

JKH-C7, SEQ ID NO: 3
QVQLVESGGGGLVQAGGSLRLSCAASGRTFSG-YAMGWFRQAPGKEREFVADISWSGH NTYYGDSVKGRFTISRD-TAKNTVYLQMNSLKPEDTAVYYCAAEGARTH-LSDSYYFPG LWAE-PPVGYWGQGTQVTVSSEPKTPKPQ

SEQ ID NO: 4
CAGGTGCAGCTGGTGGAGTCGGGTGGGG-GAGGACTGGTGCAGGCTGGGGGCTCTCTG AGACTCTCCTGTGCAGCCTCTGGACGCACCTT CAGTGGCTATGCCATGGGCTGGTTC CGCCAGGCTCCGGGGAAGGAGCGT-GAGTTTGTAGCCGATATTAGCTGGAGTGGTCAT AACACGTACTATGGAGACTCCGTGAAGGGCC-GATTCACCATCTCCAGAGACACCGCC AAGAACACGGTGTATCTGCAAATGAACAGCCT-GAAACCTGAGGACACGGCCGTTTAT TACTGTGCAGCGGAGGGGGCCCGTA-CACACCTTAGTGATAGTTACTACTTCCCGGGC CTCTGGGCCGAACCCCCCGTGGGC-TACTGGGGCCAGGGGACCCAGGT-CACTGTCTCC TCAGAACCCAAGACAC-CAAAACCACAA

JKH-D12, SEQ ID NO: 5
QVQLVETGGGLVQAGGTLRLSCAASGRTFT-SYYIGWFRQEPGKEREFVASIGWTDDN TYY-ADSVKGRFTISRDNAETTAYLQMSGLKPED-TAVYYCAADYGSGIRAWYNWIYWG QGTQVTVSSEPKTPKPQ

SEQ ID NO: 6
CAGGTGCAGCTGGTGGAGACCGGGGGAGGAT-TGGTGCAGGCTGGGGGCACTCTGAGA CTCTCCTGTGCAGCCTCTGGACGTACCTT-CACGAGCTATTACATTGGCTGGTTCCGC CAG-GAACCAGGGAAGGAGCGT-GAGTTTGTAGCAAGTATCGGCTGGACCGATGA TAAC ACATACTATGCAGACTCCGTGAAGGGCC-GATTCACCATCTCCAGAGACAACGCCGAG ACCACGGCATATCTGCAAATGTCGGGCCT-GAAACCTGAGGACACGGCCGTTTATTAC TGTGCAGCCGACTACGGGTCAGGGA-TACGGGCCTGGTATAATTGGATTTACTGGGGC CAGGGGACCCAGGT-CACCGTCTCCTCAGAACCCAAGACAC-CAAAACCACAA

JKM-A6, SEQ ID NO: 7
QLQLAETGGGLVQPGGSLRLSCAASGATLDTYIIT-WFRQAPGKEREAVSCINRSGST TYSDSVKGRFTISRDNAQKTVYLQMNSLNPED-TAIYYCAADASYRTCGGSWWNWAYW GQGTQVTVSSEPKTPKPQ

SEQ ID NO: 8
CAGTTGCAGCTCGCGGAGACGGGAG-GAGGCTTGGTGCAGCCTGGGGGGTCTCTGAGA CTCTCCTGTGCAGCCTCTGGCGCCACTTTGGA-TACTTATATCATAACCTGGTTCCGC CAGGCCCCAGGGAAGGAGCGTGAGGCCGTCT-CATGTATTAATCGTAGTGGTAGCACG ACCTAT-TCAGACTCCGTGAAGGGCCGATTCAC-CATCTCCAGAGACAACGCCCAGAAA ACGGTGTATCTGCAGATGAACAGCCT-GAACCCTGAGGACACAGCCATTTATTACTGC GCAGCGGATGCTTCGTACCGTACTTGCGGCGG-GAGTTGGTGGAATTGGGCGTACTGG GGCCAGGGGACCCAGGT-CACCGTCTCCTCAGAACCCAAGACAC-CAAAACCACAA

JKO-A4, SEQ ID NO: 9
QVQLAESGGGSVQPGGSLRLSCAASGFTFS-SYTMSWVRQAPGKGIEWVSDINGGGDR TDY-ADSVKGRFTISRDNARNTLYLQMNSLQPED-TAVYYCAKDLSYVSGTYFANDWGQ GTQVTVSSEPKTPKPQ

SEQ ID NO: 10
CAGGTGCAGCTCGCGGAGTCTGGAGGAGGCTCGGTGCAACCTGGGGGGTCTCTGAGA CTCTCCTGTGCAGCCTCTGGATTCACCTTCAGTAGTTATACTATGAGCTGGGTCCGC CAGGCTCCAGGAAAGGGGATCGAGTGGGTCTCAGATATTAATGGGGGTGGTGATAGA ACAGACTATGCAGACTCCGTGAAGGGCCGATTCACCATCTCCAGAGACAACGCCAGG AACACGCTGTATCTGCAAATGAACAGCCTGCAACCTGAGGACACGGCCGTGTATTAC TGTGCAAAAGATCTGAGCTACGTTAGTGGTACTTATTTCGCGAACGACTGGGGCCAG GGGACCCAGGTCACCGTCTCCTCCGAACCCAAGACACCAAAACCACAA

JKO-B8, SEQ ID NO: 11
QLQLAESGGGLVQ

GACTC TCCTGTGGAGCCTCTGGAAT-
GAGTTTGGATTACTATGCCATAGCCTGGTACC
GCCAGGCC CCAGGGAAGGAGCGT-
GAGGGGGTCTCATGTATTAGTGT-
TAGTGGCAGTAGCGCACAATAT TTA-
GACTCCGTGAGGGGTCGCTTCATCATCTCCAAA-
GACAACACCAAGAGCACGGCGTAT
CTGCAAATGAACAGCCTGAAGCCTGAA-
GACACAGCCGTTTAT-
TACTGCGCAGCCCTGGCC GACTGTGCAGGC-
TATGCCAGTCTTACCTTTGACTTTGATTCTTGG
GGCCAGGGGACCCAG
GTCGCCGTCTCCTCGGCGCACCACAGCGAA-
GACCCCTCG

JLJ-F9, SEQ ID NO: 23
QVQLVESGGGLVQAGGSLRLSCAPSRLTLDFFA-
IAWFRQAPGKEREGVSCISSHDGSTYY
TDSVKGRFTISKDNAKNTVYLQMNSLKPED-
TAVYYCALDHNVGTCQLTQAEYDYWGQGTQ
VTVSSAHHSEDPS

SEQ ID NO: 24
CAGGTGCAGCTGGTGGAGTCCGGTG-
GAGGCTTGGTGCAGGCTGGGGGGTCTCTGA-
GACTC TCCTGTGCACCCTCGCGATTAACTTTG-
GATTTCTTTGCCATAGCCTGGTTCCGCCAGGCC
CCAGGGAAGGAGCGTGAGGGGGTCTCATGT-
ATTAGTAGTCATGATGGTAGCACATACTAC
ACAGACTCCGTGAAGGGCCGATTCACCATCTC-
CAAAGACAACGCCAAGAACACGGTGTAT
CTGCAAATGAACAGCCTGAAGCCT-
GAGGACACAGCCGTTTATTACTGTGCCCTA-
GACCAT AACGTGGGTACCTGCCAACTCACC-
CAAGCTGAGTATGACTACTGGGGCCAGGGA
CCCAG GTCACCGTCTCCTCGGCGCAC-
CACAGCGAAGACCCCTCG

JLJ-G3, SEQ ID NO: 25
QVQLVESGGGLVQSGGSLRLSCAASGSIDS-
LYHMGWYRQAPGKERELVARVQDGGSTAYK
DSVKGRFTISRDFSRSTMYLQMNSLKPED-
TAIYYCAAKSTISTPLSWGQGTQVTVSSEPK
TPKPQ

SEQ ID NO: 26
CAGGTGCAGCTGGTGGAGTCCGGGG-
GAGGCTTGGTGCAGTCTGGGGGGTCTCTGA-
GACTC TCCTGTGCAGCCTCTGGAAGTATCGA-
TAGTCTCTATCATATGGGCTGGTACCGCCAGG
CT CCAGG-
GAAGGAGCGCGAGTTGGTCGCACGAGTTCAA-
GATGGGGGTAGCACAGCGTACAAA
GACTCTGTGAAGGGGCGATTCAC-
CATCTCCAGAGACTTTTCCAGGAGCAC-
GATGTATCTG CAAATGAACAGCCTGAAACCT-
GAGGACACGGCCATCTATTACTGTGCGGCGA
AGAGTACA ATT-
AGCACCCCCTTGTCCTGGGGCCAGGGGACCC
AGGTCACCGTCTCCTCGGAACCCAAG ACAC-
CAAAACCACAA

JLK-D7, SEQ ID NO: 27
QVQLVESGGGLVQAGGSLRLS-
CAASGFTLGHNQVAWFRQAPGKEREGVACISAT-
GASTHY ADPVKGRFTVSRDNTKNV-
VYLQVNSLKPEDTANYVCASRFSLMSIDASMCL-
SAPQYDRWG QGTQVRISSEPKTPKPQ

SEQ ID NO: 28
CAGGTGCAGCTGGTGGAGTCCGGTG-
GAGGCTTGGTGCAGGCTGGGGGGTCTCTGA-
GACTC TCCTGTGCAGCCTCTGGATT-
CACTTTGGGACATAATCAAGTAGCCTGGTTCC
GCCAGGCC CCAGGCAAGGAGCGT-
GAGGGGGTCGCGTGTATTAGCGC-
CACCGGTGCTAGCACACACTAT GCA-
GACCCCGTGAAGGGCCGATTTACCGTCTCCA
GAGACAACACCAAGAACGTGGTGTAT
CTGCAAGTGAACAGCCTGAAACCT-
GAGGACACGGCCAATTATGTCTGTGCAAGCA-
GATTC TCCCTTATGTCGATCGATGCGAG-
CATGTGCCTTTCGGCGCCTCAGTATGACCGCT
GGGGC
CAGGGGACCCAGGTCAGAATCTCCTCAGAAC
CCAAGACACCAAAACCACAA

JLK-F7, SEQ ID NO: 29
QVQLVETGGLVQPGGSLRLSC-
TASGFTLGHHRVGWFRQAPGKEREGVA-
CISATGLSSHYS DFVIGRFTVSRDNDNNV-
VYLQVNGLKPEDTAVYYCASRFSLNSVDANM
CLSEPQYDNWGQ GTPVRISSEPKTPKPQ

SEQ ID NO: 30
CAGGTGCAGCTGGTGGA-
GACGGGTGGCTTGGTGCAGCCTGGGGGGTCT
CTGAGACTCTC TGTACAGCCTCTGGATT-
CACTTTGGGACAC-
CATCGCGTTGGCTGGTTCCGCCAGGCCCCA
GGAAAGGAGCGTGAGGGGGTCGCGTGTATT-
AGCGCCACTGGTCTTAGTTCACACTATTCA
GACTTCGTGATCGGCCGATT-
TACCGTCTCCAGA-
GACAACGACAACAACGTGGTGTATCTA
CAAGTGAACGGCCTGAAACCT-
GAGGACACAGCCGTTTATTACTGTGCAAGCA-
GATTCTCC CTTAATTCGGTC-
GATGCGAATATGTGCCTTTCGGAGCCTCAGTA
TGACAACTGGGGCCAG
GGGACCCCGGTCAGAATCTCCTCAGAACC-
CAAGACACCAAAACCACAA

JLK-G12, SEQ ID NO: 31
QVQLVESGGGLVQAGGSLRLSCAASE-
FRAEHFAVGWFRQAPGKEREGVSCVDASGD-
STAY ADSVKGRFTISRDNNKNVVYLQMD-
SLEPEDTGDYYCGASYFTVCAKSMRKIEYRY
WGQGT QVTVSSEPKTPKPQ

SEQ ID NO: 32
CAGGTGCAGCTGGTGGAGTCCGGTG-
GAGGCTTGGTGCAGGCTGGGGGGTCTCTGA-
GACTC TCCTGTGCAGCCTCTGAATTCCGTGCG-
GAGCATTTTGCCGTGGGCTGGTTCCGCCAG
GCC CCAGGGAAGGAGCGTGAGGGGGTCT-
CATGTGTAGACGCGAGTGGTGATAGTACAG-
CATAT GCGGACTCTGTGAAGGGCCGATTCAC-
CATCTCCAGAGACAACAACAAGAACGTAGT
GTAT CTGCAAATGGACAGCCTGGAACCTGAA-
GACACAGGAGATTATTATTGTGGAGCCTCGTAC
TTTACTGTCTGCGCCAAGAGCATGCGGAAAAT
TGAATATAGGTACTGGGGCCAGGGGACC
CAGGTCACCGTCTCCTCAGAACCCAAGACAC-
CAAAACCACAA

JLO-C8, SEQ ID NO: 33
QVQLAESGGGLVQPGGSLRLSCAASGRAL-
NYYVIGWFRQAPGKEREGVSCIASSEAYTDY
ADSVQGRFTISRDKALNTVYLDMKRLKPDD-
TAVYYCAARLRDPNWCGRNADEYDSWGQGT
QVTVSSEPKTPKPQ

SEQ ID NO: 34
CAGGTGCAGCTCGCGGAGTCAGGCG-
GAGGCTTGGTGCAGCCTGGGGGGTCTCTGA-

GACTC TCCTGTGCAGCCTCTGGACGCGCTTTGAATTATTATGTCATAGGCTGGTTCCGCCAGGCC CCAGGGAAGGAGCGTGAGGGGGTCTCATGTATTGCGAGTAGCGAAGCCTACACAGACTAT GCAGACTCCGTGCAAGGCCGATTCACCATCTCGAGAGACAAGGCTCTGAATACGGTGTAT TTGGATATGAAGCGCCTGAAACCTGACGACACAGCCGTTTATTATTGTGCAGCCCGGTTG CGTGATCCTAATTGGTGCGGGCGGAATGCGGATGAGTATGACTCCTGGGGCCAGGGGACC CAGGTCACCGTCTCCTCAGAACCCAAGACACCAAAACCACAA

JLO-G7, SEQ ID NO: 35
QVQLVESGGGLVQAGGSLRLSCAASGFPFGSYYMSWVRQAPGKGPEWVSDISNGGIITRY SDSVKGRFTISRDNAKNILYLQMNSLKPEDTALYFCATGTGRDWSREYRGQGTQVTVSSE PKTPKPQ

SEQ ID NO: 36
CAGGTGCAGCTGGTGGAGTCCGGTGGAGGCTTGGTGCAGGCTGGGGGGTCTCTGAGACTC TCCTGTGCAGCCTCTGGATTCCCCTTCGGTAGTTACTACATGAGCTGGGTCCGCCAGGCT CCAGGAAAGGGGCCCGAGTGGGTCTCAGATATTAGCAATGGTGGTATTATTACAAGGTAT TCAGACTCCGTGAAGGGCCGATTCACCATCTCCCGAGACAACGCCAAGAACATATTGTAT CTGCAAATGAACAGCCTGAAACCTGAAGACACGGCCCTGTATTTCTGTGCGACAGGGACC GGTAGAGACTGGAGCAGGGAGTACCGGGGCCAGGGGACCCAGGTCACCGTCTCCTCAGAA CCCAAGACACCAAAACCACAA

JLO-G11, SEQ ID NO: 37
QVQLAESGGGLVQPGGSLRLSCEASGFHLEHFAVGWFRQAPGKEREGVSCISASGDSTTY ADSVKGRSTISKDNAKNAVYLQMDSLRPEDTGDYYCAASHFSVCGKNIRKIEYRYWGQGT PVTVSSEPKTPKPQ

SEQ ID NO: 38
CAGGTGCAGCTCGCGGAGTCTGGTGGAGGCTTGGTGCAGCCTGGGGGGTCTCTGAGACTC TCCTGTGAAGCCTCAGGATTCCATTTGGAGCATTTTGCCGTAGGCTGGTTCCGCCAGGCC CCAGGGAAGGAGCGTGAGGGGGTCTCATGTATAAGCGCGAGTGGTGATAGTACAACGTAT GCAGACTCCGTGAAGGGCCGATCCACCATCTCCAAAGACAACGCCAAGAACGCGGTGTAT CTGCAAATGGACAGCCTGAGACCCGAGGACACAGGCGATTATTACTGTGCAGCCTCGCAC TTCAGTGTCTGCGGCAAGAACATTCGGAAAATTGAGTATAGGTACTGGGGCCAGGGGACC CCGGTCACCGTCTCCTCAGAACCCAAGACACCAAAACCACAA

JLU-A4, SEQ ID NO: 39
QVQLVETGGGLVQPGGSLRLSCVVSGLTFNSNYMSWVRQAPGKGPELVSYINSEDGSTFY ADSVKGRFTISRDNNENTLYLQMSSLKPEDTARYYCALGIAGATRGQGTQVTVSSEPKTP KPQ

SEQ ID NO: 40
CAGGTGCAGCTCGTGGAGACCGGGGGAGGCTTGGTGCAGCCGGGGGGGTCTCTGAGACTC TCCTGTGTAGTGTCTGGATTAACCTTCAATAGCAACTACATGAGTTGGGTCCGCCAGGCT CCAGGGAAGGGGCCCGAGTTGGTCTCATATATTAATTCTGAAGATGGTAGTACCTTTTAT GCAGACTCCGTGAAGGGCCGATTCACCATCTCGCGAGACAACAACGAGAATACACTGTAT CTGCAAATGAGCAGCCTGAAGCCTGAGGACACGGCCCGCTATTACTGTGCACTGGGGATC GCTGGTGCAACTCGGGGCCAGGGGACCCAGGTCACCGTCTCCTCAGAACCCAAGACACCA AAACCACAA

JLU-D10, SEQ ID NO: 41
QVQLVESGGGLVQPGGSLRLSCAASGFTLDSYAIGWFRQAPGKEREGVACISASGSGTDY VDSVKGRFTVSRDQAKSMVFLQMNNMKPEDAAVYYCAADYRPRPLPIQAPCTMTGGNYWG QGTQVTVSSEPKTPKPQ

SEQ ID NO: 42
CAGGTGCAGCTCGTGGAGTCAGGGGGAGGCTTGGTGCAGCCTGGGGGGTCTCTGAGACTC TCCTGTGCAGCCTCTGGATTCACTTTAGATAGTTATGCAATAGGCTGGTTCCGCCAGGCC CCAGGGAAGGAGCGTGAGGGGGTCGCATGGTATTAGTGCTAGTGGTAGTGGCACGGACTAT GTAGACTCCGTGAAGGGCCGATTCACCGTCTCCAGAGACCAGGCCAAGAGCATGGTGTTT CTGCAAATGAACAACATGAAACCTGAGGACGCAGCCGTTTATTACTGTGCAGCAGATTAT CGGCCGAGGCCCCTGCCGATTCAGGCGCCGTGTACAATGACAGGTGGCAACTACTGGGGC CAGGGGACCCAGGTCACCGTCTCCTCAGAACCCAAGACACCAAAACCACAA

JLU-H6, SEQ ID NO: 43
QVQLVESGGGLVQPGGSLTLSCVASGSNLDYFAIGWFRQAPGKEREGVSCISTSSDMSKY ADSVKGRFTISRDNTRNTVYLQMNSLEPEDTAVYYCAAKRRRYGLDRDMCLMDSVGMDVW GKGTLVTVSSAHHSEDPS

SEQ ID NO: 44
CAGGTGCAGCTGGTGGAGTCGGGGGGAGGCTTGGTGCAGCCTGGGGGGTCTCTGACACTC TCCTGTAGCCTCTGGATCCAATTTGGATTATTTTGCGATAGGCTGGTTCCGCCAGGCCCC AGGGAAGGAGCGTGAGGGGGTCTCATGTATTAGTACGAGTAGTGACATGTCAAAGTATGC AGACTCCGTGAAGGGCCGCTTCACCATCTCCAGAGACAACACCAGGAACACGGTGTATCT GCAAATGAACAGCCTGGAACCCGAAGATACGGCCGTTTATTATTGTGCAGCAAAGCGCCG CCGATATGGTCTCGATCGTGATATGTGTCTTATGGATTCGGTCGGCATGGACGTGTGGGG CAAAGGGACCCTGGTCACCGTCTCCTCGGCGCACCACAGCGAAGACCCCTCG

JLU-H9, SEQ ID NO: 45
QVQLVESGGGLVQPGGSLRLSCAAPGFTLDYYAIGWFRQAPGKEREGVSCIRSRGDRTNY ADSVKGRFTVSRDNAKNTAYLQMNNLKPEDTGVYFCAAAPRTTVQDLCVTPLLGGADWVS WGQGTQVTVSSEPKTPKPQ

SEQ ID NO: 46
CAGGTGCAGCTCGTGGAGTCAGGAGGAGGCTTGGTGCAGCCTGGGGGGTCTCTGAGACTC TCCTGTGCAGCTCCTGGATTCACTTTGGATTATTATGCCATAGGCTGGTTCCGCCAGGCC

CCAGGGAAGGAGCGTGAGGGGGTCTCATGTATTCGTAGTCGTGGTGATCGGACAAATTATGCAGACTCCGTGAAGGGCCGATTCACCGTCTCCAGAGACAACGCCAAGAACACGGCGTAT CTGCAAATGAACAACCTGAAACCTGAGGACACAGGCGTTTATTTCTGTGCAGCTGCTCCG AGGACTACTGTTCAGGATTTGTGTGTAACCCCTCTTTTGGGGGGTGCTGACTGGGTTTCC TGGGGCCAGGGGACCCAGGTCACCGTCTCCTCGGAACCCAAGACACCAAAACCACAA

JLU-H10, SEQ ID NO: 47
QLQLVESGGGLVQPGGSLRLSCAASGFPLGDYTVGWFRQAPGKEREGVSCISKGSRGLRY GDSVKGRFTVARDNAKSTVTLQMDSLKPEDTAVYSCAAGPAMFNQCHMVDNYFTYWGQGT QVTVSSAHHSEDPS

SEQ ID NO: 48
CAGTTGCAGCTGGTGGAGTCTGGCGGAGGCTTGGTGCAGCCTGGGGGGTCTCTGAGACTC TCCTGTGCAGCCTCTGGATTCCCTTTGGGTGATTATACCGTGGGCTGGTTCCGCCAGGCC CCAGGGAAGGAGCGTGAGGGGGTCTCATGTATTAGTAAAGGTAGTAGAGGCTTAAGATAC GGAGACTCCGTGAAGGCCGATTCACCGTTGCCAGAGACAACGCCAAGAGCACGGTAACTCTGCAAATGGACAGCCTGAAACCGGAGGACACAGCCGTTTATTCTTGTGCTGCAGGGCCG GCCATGTTCAATCAATGTCATATGGTCGACAATTACTTTACATACTGGGGTCAGGGGACC CAGGTCACCGTCTCCTCGGCGCACCACAGCGAAGACCCCTCG

New BoNT/E-Binding VHHs
JLD-B12, SEQ ID NO: 49
QVQLVETGGGLVQAGGSLRLSCAASGRTFSNYAMGWFRQAPGKEREFVAAISWSGAHTYY ADSVKGRFTISRDNAKSTMYLQMNSLKPEDTAVYYCNADLERYSDFGREVDDYWGQGTQV TVSSEPKTPKPQ SEQ ID NO: 50
CAGGTGCAGCTCGTGGAGACAGGTGGAGGATTGGTGCAGGCTGGGGGGTCTCTGAGACTC TCCTGTGCAGCCTCTGGACGCACCTTCAGTAACTATGCCATGGGCTGGTTCCGCCAGGCT CCAGGGAAGGAGCGTGAGTTTGTCGCAGCTATTAGCTGGAGTGGTGCTCACACATACTAT GCAGACTCCGTGAAGGGCCGATTCACCATCTCCAGAGACAACGCCAAGAGCACGATGTAT CTGCAAATGAACAGCCTGAAACCTGAGGACACGGCCGTCTATTACTGTAATGCAGA TCTC GAGCGGTATAGTGACTTCGGTAGGGAGGTGGATGACTACTGGGGCCAGGGGACCCAGGTC ACCGTCTCCTCAGAACCCAAGACACCAAAACCACAA JLE-A12, SEQ ID NO: 51
QVQLVESGGGLVQPGGSLRLSCTASGLTLAKWTINWFRQAPGKEREGISCISSSSGSTYY ADSVKGRFTISRDNAENTVYLQMSSLKPEDTAVYYCAADSFKGCTFLSSTTHYNNMDYWG KGTLVTVSSAHHSEDPS SEQ ID NO: 52
CAGGTGCAGCTCGTGGAGTCGGGTGGAGGCTTGGTGCAGCCTGGGGGGTCTCTGAGACTC TCGTGTACAGCCTCTGGATTAACTTTGGCTAAGTGGACCATCAACTGGTTCGCCAGGCC CCAGGGAAGGAGCGCGAGGGGATCTCATGTATTAGTAGCAGTAGTGGTAGCACATACTAT GCAGACTCCGTGAAGGGCCGATTCACCATCTCCAGAGACAACGCCGAAAACACGGTATAT CTGCAAATGAGCAGCCTGAAACCTGAGGACACGGCCGTTATTACTGTGCAGCGATTCT TTTAAGGGCTGTACGTTCCTCAGTAGTACTACCCATTACAACAACATGGACTACTGGGGC AAAGGGACCCTGGTCACCGTCTCCTCAGCGCACCACAGCGAAGACCCCTCG JLE-B10, SEQ ID NO: 53
QVQLVESGGGLVQSGGSLRLSCAASRRTASNYAVAWFRQAPGKEREFVAAIGWSDDVTYY ADSVKGRFTVSRDNAKNTVYLQMNGLEPEDTAVYYCTTNGDRYSYRTASSYHYWGQGTQV TVSSAHHSEDPS SEQ ID NO: 54
CAGGTGCAGCTCGTGGAGTCGGGTGGGGATTGGTGCAGTCTGGGGGCTCTCTGAGACTC TCCTGTGCAGCCTCTAGACGCACCGCCAGTAACTATGCCGTGGCCTGGTTCCGCCAGGCT CCAGGAAAGGAGCGTGAGTTTGTAGCAGCGATTGGCTGGAGTGATGATGTCACGTATTAC GCAGACTCCGTGAAGGGCCGATTCACCGTCTCCAGAGACAACGCCAAGAACACGGTGTAT CTGCAAATGAACGGCCTGGAACCTGAGGACACGGCCGTTATTACTGTACAACAAATGGT GATAGATACAGTTACAGGACGGCATCCAGCTATCACTACTGGGGCCAGGGGACCCAGGTC ACCGTCTCCTCAGCGCACCACAGCGAAGACCCCTCG JLE-C7, SEQ ID NO: 55
QVQLAETGGGSVQTGGSLRLSCAASGLPFRNYAMAWFRQAPGKEREFVAAISREGGRTYY ADFVKGRFTISRDNGRNTIYLEMNSLASEDTAIYYCAGVEGAYTYRTGASYTYWGQGTQV TVSSEPKTPKPQ SEQ ID NO: 56
CAGGTGCAGCTCGCGGAGACTGGGGGAGGATCGGTGCAGACTGGGGGCTCTCTGAGGCTC TCCTGTGCAGCCTCTGGACTGCCCTTCAGAAACTATGCCATGGCCTGGTTCCGCCAGGCT CCAGGGAAGGAGCGTGAGTTTGTAGCAGCTATTAGTCGGGAAGGCGGGAGGACATACTAT GCAGACTTCGTGAAGGGCCGATTCACCATCTCCAGAGACAACGGCAGGAACACGATATAT CTGGAGATGAACAGCCTGGCATCGGAGGATACGGCCATTTATTACTGTGCCGGTGTCGAG GGTGCTTATACTTATCGTACCGGGGCCTCGTATACTTACTGGGGCCAGGGGACCCAGGTC ACCGTCTCCTCAGAACCCAAGACACCAAAACCACAA JLE-E5, SEQ ID NO: 57
QVQLVETGGGLVQAGGSLRLSCAASGRSYAMGWFRQGPGKEREFVATISWSSTNTWYADS VKGRFTISRDNAKNTVYLQMNSLKPEDTAVYYCAASHRFSDYPMRSEDGMDYWGKGTL VT VSSEPKTPKPQ SEQ ID NO: 58
CAGGTGCAGCTGGTGGAGACGGGGGGAGGATTGGTGCAGGCTGGGGGCTCTCTGAGACTCTCCTGTGCAGCCTCTGGACGCAGTTATGCCATGGGCTGGTTCCGCCAGGGTCCAGGGAAGGAGCGTGAGTTTGTAGCCACTATCAGTTGGAGTAGTACTAACACATGGTATGCAGATTCCGTGAAGGGCCGATTCACCATCTCTAGAGACAACGCCAAGAACACGGTGTATCTGCAAATGAACAGCCTGAAACCTGAGGACACGGCTGTTTATTACTGTGCAGCGAGCCATCGTTTTAGC GACTATCCCATGAGGTCAGAGGACGGCATGGACTACTGGGGCAAAGGGACCCTGGTCACCGTCTCCTCAGAACCCAAGACACCAAAACCACAA JLE-E9, SEQ ID NO: 59
QVQLVETGGGLVQAGGSLRLSCAASGRTFSSYSMGWFRQAPGKEREYVAAVNSNGDSTFYADSIKGRFTVSRDAAKNTVYLQMNSLKPEDTALYYCAAVYGRYTYQSPKSYEYWGQGTQVTVSSEPKTPKPQ SEQ ID NO: 60
CAGGTGCAGCTGGTGGAGACGGGAGGAGGATTGGTGCAGGCTGGGGGCTCTCTGAGACTCTCGTGTGCAGCCTCTGGACGCACCTTCAGTAGCTATTCCATGGGCTGGTTCCGCCAGGCTCCAGGGAAGGAGCGTGAGTATGTAGCAGCAGTTAACTCCAATGGCGACAGTACATTCTAT GCCGACTCCATTAAGGGCCGATTCACCGTCTCCAGAGACGCCGCCAAGAACACAGTCTAT CTGCAAATGAACAGCCTGAAACCTGAGGACACGGCCCTTTATTACTGTGCAGCTGTCTAC GGTAGATACACTTACCAGTCCCCAAAATCGTATGAGTACTGGGGCCAGGGGACCCAGGTCACCGTCTCCTCAGAACCCAAGACACCAAAACCACAA JLE-G6, SEQ ID NO: 61
QLQLVETGGGLVKPGGSLRLSCVVSGFTFDDYRMAWVRQAPGKELEWVSSIDSWSINTYYEDSVKGRFTISTDNAKNTLYLQMSSLKPEDTAVYYCAAEDRLGVPTINAHPSKYDYNYWGQGTQVTVSSEPKTPKPQ SEQ ID NO: 62
CAGTTGCAGCTCGTGGAGACTGGTGGAGGCTTGGTGAAGCCTGGGGGTTCTCTGAGACTC TCCTGTGTAGTCTCCGGATTCACTTTTGATGATTATCGCATGGCTTGGGTCCGCCAGGCTCCAGGGAAGGAGCTGGAGTGGGTGTCCAGTATAGATAGTTGGAGTATCAACACATACTAT GAAGACTCCGTGAAGGGCCGGTTCACCATCTCCACAGACAACGCCAAGAATACACTGTAT CTGCAAATGAGCAGCCTGAAACCTGAGGACACGGCCGTGTATTACTGTGCAGCAGGACCGCTTAGGTGTACCGACTATTAACGCCCACCCTTCAAAATATGATTATAACTACTGGGGGCAGGGGACCCAGGTCACCGTCTCCTCAGAACCCAAGACACCAAAACCACAA JLE-H5, SEQ ID NO: 63
QVQLVESGGGLVQAGGSLRLSCAASGRTFTSYAMGWFRQAPGKEREFVASISWRGSYTYYSDSVKGRFTISRDYAENTMYLQMNSLKPEXTGRYYCATLTGDVSVGEYDNRGQGTQVTVSSAHHSEDPS SEQ ID NO: 64
CAGGTGCAGCTGGTGGAGTCCGGTGGAGGCTTGGTGCAGGCTGGGGGGTCTCTGAGACTC TCCTGTGCAGCCTCTGGACGCACCTTCACTAGTTATGCCATGGGCTGGTTCCGCCAGGCT CCAGGGAAGGAGCGTGAGTTTGTAGCGTCTATTAGCTGGCGCGGTAGTTACACATACTAT TCAGACTCCGTGAAGGGCCGATTCACCATCTCCAGAGATTACGCCGAGAACACGATGTAT CTGCAAATGAACAGCCTGAAACCTGAGGNNACGGGCAGATATTACTGTGCAACCTTAACCGGCGACGTGAGTGTCGGCGAGTATGACAACCGGGGCCAGGGGACCCAGGTCACTGTCTCC TCAGCGCACCACAGCGAAGACCCCTCG JLF-H5, SEQ ID NO: 65
QVQLVESGGGSVQPGGSLRLSCVASGFTFTNYAMAWVRQVSGKGLEGVAAISSEGFIYIP DSVKGRFTISRDNAKNTVYLQMDNLQSEDTAIYHCAAVDWKRVAAMNSYNMDYWGKGTPV TVSAEPKTPKPQ SEQ ID NO: 66
CAGGTGCAGCTGGTGGAGTCGGGGGGAGGCTCGGTGCAGCCTGGGGGGTCTCTGAGACTC TCCTGTGTAGCCTCTGGATTCACCTTCACTAATTACGCGATGGCCTGGGTCCGCCAGGTA TCAGGGAAGGGGCTCGAGGGTGTGGCCGCTATTAGTAGTGAGGGTTTCATATATATCCCA GACTCAGTGAAGGGCCGATTCACCATCTCCAGAGACAACGCCAAGAACACGGTGTATCTA CAAATGGACAACCTCCAGTCTGAGGATACGGCCATATATCACTGTGCGGCAGTTGATTGG AAACGGGTCGCCGCGATGAACAGCTACAACATGGACTACTGGGGAAAAGGGACCCCGGTC ACCGTCTCCGCAGAACCCAAGACACCAAAACCACAA JLG-G8, SEQ ID NO: 67
QLQLVESGGGLVQAGGSLRLSCAASGRTFSSYAMGWFRQAPGKEREHVAAISWSGGYTYY ANSVKGRFTISRDNAKNTVYLQMNSLKPEDTAVYYCNGVQDHSDSLQNWGQGTQVTVSSE PKTPKPQ SEQ ID NO: 68
CAGTTGCAGCTGGTGGAGTCGGGCGGAGGATTGGTGCAGGCTGGGGGGTCTCTGAGACTCTCCTGTGCAGCCTCTGGACGCACCTTCAGTAGCTATGCCATGGGCTGGTTCCGCCAGGCTCCAGGGAAGGAACGTGAGCATGTCGCAGCTATTAGCTGGAGTGGTGGTTACACATACTATGCAAACTCCGTGAAGGGCCGATTCACCATCTCCAGAGACAACGCCAAGAACACGGTGTAT CTGCAAATGAACAGCCTGAAACCTGAGGACACGGCCGTCTATTACTGTAATGGAGTTCAG GACCATAGCGACTCCCTTCAGAACTGGGGCCAGGGACCCAGGTCACCGTCTCCTCAGAA CCCAAGACACCAAAACCACAA JLG-G12, SEQ ID NO: 69
QLQLVETGGGLVQAGGSLRLSCAASGRTFSSYAVGWFRQAPGKEREFVAAISWSGSYAYY ADSVKGRFTISRD-

NAKNTVYLQMNSLKPEDTAVYYCNGDLEGYSNHETGDYWGQGTQVTV SSEPKTPKPQ

SEQ ID NO: 70
CAGTTGCAGCTGGTGGAGACGGGAGGAGGATTGGTGCAGGCTGGGGGGTCTCTGAGACTCTCCTGTGCAGCCTCTGGACGCACCTTCAGTAGTTATGCCGTGGGCTGGTTCCGCCAGGCTCCAGGGAAGGAGCGTGAGTTTGTCGCAGCTATTAGCTGGAGTGGTAGTTACGCATACTATGCAGACTCCGTGAAGGGCCGATTCACCATCTCCAGAGACAACGCCAAGAACACGGTGTAT CTGCAAATGAACAGCCTGAAACCTGAGGACACGGCCGTCTATTACTGTAATGGAGATCTT GAGGGTTATAGCAACCATGAAACCGGGGACTACTGGGGCCAGGGGACCCAGGTCACCGTCTCCTCAGAACCCAAGACACCAAAACCACAA

JLH-H4, SEQ ID NO: 71
QLQLAESGGGLVQAGGSLRLSCAASGRTFSSYAMGWFRQAPGKEREFVAAISWTGGYTYY ASSVKGRFTISRDNAKNTMYLQMNSLKPEDTAVYYCNADLESYSEYPESYY WGQGTQVTV SSEPKTPKPQ

SEQ ID NO: 72
CAGTTGCAGCTGGCGGAGTCGGGAGGAGGATTGGTGCAGGCTGGGGGGTCTCTGAGACTCTCCTGTGCAGCCTCTGGACGCACCTTCAGTAGCTATGCCATGGGCTGGTTCCGCCAGGCTCCAGGGAAGGAGCGTGAGTTTGTCGCAGCTATTAGCTGGACTGGTGGTTACACATACTATGCAAGCTCCGTGAAGGGCCGATTCACCATCTCCAGAGACAATGCCAAAAACACGATGTAT CTGCAAATGAACAGCCTGAAACCGGAGGACACGGCCGTCTATTACTGTAATGCAG TTTA GAATCCTATAGCGAGTATCCCGAGAGCTACTACTGGGGCCAGGGGACCCAGGTCACCGTC TCCTCAGAACCCAAGACACCAAAACCACAA

Appendix C

Included in Appendix C are the following: Amino acid and nucleic acid sequences of 2 anthrax edema factor (EF)-binding VHHs; 7 anthrax lethal factor (LF)-binding VHHs; and 6 VHHs binding both anthrax EF and LF (EF/LF cross-specific)

New Anthrax EF-Binding VHHs
JMN-E2, SEQ ID NO: 73
QVQLAESGGGLVQAGGSLTLSCAASGLNFDKYAIGWYRQAPGKEREGVSCISKYYNH RMYSDSVKGRFTVSSNYAKNTVYLQMTNLKP EDTAVYYCAAGCIDPEDWGQGTQVTV SSEPKTPKPQ SEQ ID NO: 74
CAGGTGCAGCTGGCGGAGTCGGGGGGAGGCTTGGTGCAGGCTGGGGGGTCTCTGACACTCTCCTGTGCAGCCTCTGGCCTCAATTTCGATAAATATGCCATAGGCTGGTACCGCCAGGCCCCAGGGAAAGAGCGTGAGGGGGTTTCATGTATTAGTAAGTATTACAATCATCGGATGTATAGTGACTCCGTGAAGGGCCGATTCACCGTCTCCAGTAACTATGCCAAGAACACGGTGTACCTGCAAATGACCAATCTGAAACCGGAGGATACGGCCGTTTATTACTGTGCGGCAGGGTGTATTGACCCGGAAGATTGGGGCCAGGGGACCCAGGTCACCGTCTCCTCAGAACCCAAGACACCAAAACCACAA JMN-F3, SEQ ID NO: 75
QVQLVETGGGQVQTGGSLRLSCAASEPTFTPKVVGWFRQAPVKERDFVATITIRTGR TLYADSVKGRFTISGDGANNTVYLQMNGLKPEDTAVYYCAASLPLAIP PTQASAYEY WGLGTQVTVSSEPKTPKPQ SEQ ID NO: 76
CAGGTGCAGCTGGTGGAGACCGGGGGAGGCCAGGTGCAGACTGGGGGATCTCTGAGA CTCTCTTGCGCAGCCTCTGAACCCACCTTCACTCCGAAAGTTGTGGGCTGGTTCCGC CAGGCTCCAGTGAAGGAGCGTGACTTTGTAGCAACTATAACAATCCGTACCGGTCGC ACACTCTATGCAGATTCCGTGAAGGGCCGATTCACCATCTCCGGAGACGGCGCCAAC AATACGGTGTATCTACAAATGAACGGCCTGAAACCTGAGGACACGGCCGTTTATTAC TGCGCCGCATCTCTTCCGCTAGCAATACCACCGACGCAGGCTTCGGCATATGAATAC TGGGGCCTGGGGACCCAGGTCACCGTCTCCTCAGAACCCAAGACACCAAAACCACAA New Anthrax LF-Binding VHHs
JMO-A2, SEQ ID NO: 77
QVQLVETGGGLVQPGGSLRLSCSVSGLHFRFANMGWFRQAPGKQRELVAYITTGDNT NYVDHVKGRFTISRDNAKNTVYLQMNSLKPEDTAVYYCNIVNALGEFNPRNDWGQGT QVTVSSEPKTPKPQ SEQ ID NO: 78
CAGGTGCAGCTGGTGGAGACGGGGGGAGGCTTGGTGCAGCCTGGGGGGTCTCTGAGA CTCCTGTTCAGTCTCTGGCCTCCACTTCAGGTTCGCGAACATGGGATGGTTTCGC CAGGCTCCAGGGAAGCAGCGCGAGTTGGTCGCATATATTACTACTGGTGATAACACT AACTATGTAGACCACGTGAAGGGCCGATTCACCATCTCCAGAGACAACGCCAAGAAC ACGGTGTATCTGCAAATGAACAGCCTGAAACCTGAAGACACGGCCGTCTACTACTGT AATATAGTCAATGCGCTGGGGGAGTTCAATCCCCGAAACGACTGGGGCCAGGGGACC CAGGTCACCGTCTCCTCAGAACCCAAGACACCAAAACCACAA JMO-B3, SEQ ID NO: 79
QVQLVETGGGWVQAGGSLRLSCAASGRAASGNAMAWFRQAPGKEREFVALISWSGGR PYYANSVKGRFAISRDNATNTVYLQMNRLKPEDTAVYYCAASPTIAILPTPYDYWGQ GTQVTVSSEPKTPKPQ SEQ ID NO: 80
CAGGTGCAGCTGGTGGAGACGGGTGGGGGTGGGTACAGGCTGGGGGCTCTCTGAGA CTCTCCTGTGCAGCCTCTGGACGCGCCGCAGTGGAAATGCCATGGCCTGGTTCCGC CAGGCTCCAGGAAAGGAGCGTGAGTTTGTAGCATTGATTAGTTGGAGTGGTGGTCGC CCATACTATGCAAACTCCGTGAAGGGCCGATTCGCCATCTCCAGAGACAACGCCACG AATACGGTGTATCTGCAAATGAACAGACTGAAACCTGAGGACACGGCCGTTTATTAC TGTGCAGCGTCGCCTACCATAGCGATACTACC

TACTCCGTATGACTACTGGGGCCAG GGGACCCAGGTCACCGTCTCCTCAGAACC- CAAGACACCAAAACCACAA

JMO-B9, SEQ ID NO: 81
QVQLVETGGGLVQAGASLRLSCAASGRTF- STDHMGWFRQAPQKEREFVAAINAWSGL SIYY- ADSVKGRFTISRDNDKKTAYLQMNSLKPED- TAVYYCAAKEMGRGWVPQSSDDY DAWGQGTQVTVSSEPKTPKPQ

SEQ ID NO: 82
CAGGTGCAGCTGGTGGAGACGGGGGGAGGAT- TGGTGCAGGCTGGGGCCTCTCTGAGA CTCTCCTGTGCAGCCTCTGGACGCACCTTCAG TACCGATCACATGGGCTGGTTCCGC CAGGCTC- CACAGAAGGAGCGT- GAGTTTGTGGCAGCAATAAATGCATG- GAGTGGACTC AGCATTTACTATGCAGACTCCGTGAAGGGCC- GATTCACCATCTCCAGAGACAACGAC AAGAAAACGGCATATCTACAAATGAACAGCCT- GAAACCTGAGGACACGGCCGTTTAT TACTGTGCAGC- CAAGGAGATGGGTAGGGGTTGGGTGC- CACAGAGCTCAGACGACTAT GACGCCTGGGGCCAGGGGACCCAGGT- CACCGTCTCCTCAGAACCCAAGACACCAAAA CCACAA

JMO-C1, SEQ ID NO: 83
QVQLVETGGGLVQAGGSLRLSCAVS- GRTFSSYAMAWFRQAPGKERDFVAAISWSGGA PHYEDSVKGRFTISRD- NAKNMVYLQMNSLKPDDTAVYYCAAAK- AGYYSGSYYVGGGM YDYWGQGTQVTVSSEPKTPKPQ

SEQ ID NO: 84
CAGGTGCAGCTGGTGGAGACTGGAGGAGGAT- TGGTGCAGGCTGGGGGCTCTCTGAGA CTCTCCTGTGCAGTCTCTGGACGCACCTTCA GTAGCTATGCCATGGCCTGGTTCCGC CAGGCTCCAGGGAAGGAGCGTGAT- TTTGTAGCAGCTATTAGCTGGAGTGGTGGTGCC CCACACTATGAAGACTCCGTGAAGGCCGATT- CACCATCTCCAGAGACAACGCCAAG AACATGGTATATCTCCAAATGAACAGCCT- GAAACCTGACGACACGGCCGTTTACTAC TGTGCAGCAGCGAAAGCAGGATAC- TATAGTGGTAGTTACTACGTGGGGGGGGTATG TATGACTACTGGGGCCAGGGGACCCAGGT- CACCGTCTCCTCAGAACCCAAGACACCA AAACCACAA

JMO-C10, SEQ ID NO: 85
QVQLVETGGLVQAGGSLRLSCAASGSIG- RVDNMGWYRQTPGKERERVAIITGGGTAI YADTVKGRFTVSRDNAKNTIYLQMNSVKPED- TAVYFCNADISRSIESIVYRSYWGQG TQVTVSSEPKTPKPQ

SEQ ID NO: 86
CAGGTGCAGCTGGTGGAGACAG- GAGGCTTGGTGCAGGCTGGGGGTCTCTGA- GACTC TCCTGTGCAGCCTCCG- GAAGCATCGGCAGGGTCGATAACATGGGCTG GTACCGCCAA ACTCCAGG- GAAAGAGCGCGAGCGGGTCGCAATCAT- TACTGGAGGCGGTACCGCGATC TATGCA- GACACCGTGAAGGGCCGATTCACCGTCTCCA GAGACAACGCCAAGAACACA ATATATCTA- CAAATGAACAGCGTGAAACCT- GAGGACACAGCCGTCTATTTCTGTAAT GCCGA- CATCAGTCGTAGTATTGAGTCCATCGTCTATCG TTCCTACTGGGGCCAGGGG ACCCAGGT- CACCGTCTCCTCAGAACCCAAGACAC- CAAAACCACAA

JMO-F4, SEQ ID NO: 87
QVQLVETGGGLVQPGGSLRLSCAASGNIFSI- NAMGWYRQAPGKQRELVAAISNSGST NYED- SVKGRFTVSRDNAKNTVYLQMNSLKPED- TAVYYCNAFDLVAGTRLGSWGQGTQ VTVSSEPKTPKPQ

SEQ ID NO: 88
CAGGTGCAGCTGGTGGAGACGGGGG- GAGGCTTGGTGCAGCCTGGGGGGTCTCTGAGA CTCTCCTGTGCAGCCTCTGGAAA- CATCTTCAGTATCAATGC- CATGGGCTGGTACCGC CAGGCTCCAGG- GAAGCAGCGCGAGTTGGTCGCAGCTATTAGT AATAGTGGTAGCACA AACTATGAAGACTCCGT- GAAGGGCCGATTCACCGTCTCCAGA- GACAACGCCAAGAAC ACGGTGTATCTGCAAATGAACAGCCT- GAAACCTGAGGACACGGCCGTCTATTACTGT AATGCCTTCGATT- TAGTAGCTGGTACTAGGCTGGGGTCCTGGGG CCAGGGGACCCAG GTCACCGTCTCCTCG- GAACCCAAGACACCAAAACCACAA

JMO-F12, SEQ ID NO: 89
QVQLVESGGGLVQPGGSLRLSCAASEFTLE- HAAVGWFRQAPGKEREGVSCISSRDSN TYY- ADSVKGRFTISRDNAENTVYLQMNSLKPED- TAVYYCATDVPCWDGSNWSLGHEY DYWGQGTQVTVSSEPKTPKPQ

SEQ ID NO: 90
CAGGTGCAGCTGGTGGAGTCGGGGG- GAGGCTTGGTGCAGCCTGGGGGGTCTCTGAGA CTCTCCTGTGCAGCCTCTGAATTCACTTTG- GAACATGCCGCCGTAGGCTGGTTCCGC CAGGCCCCAGG- GAAGGAGCGCGAGGGGGTCTCTTGTATT- AGTAGTCGTGATAGTAAC ACATACTATGCA- GACTCCGTGAAGGGCCGATTCACCATCTCCA GAGACAATGCCGAA AACACGGTATATCTGCAAATGAACAGCCT- GAAACCTGAGGACACGGCCGTTTATTAC TGTGCGACA- GATGTCCCCTGCTGGGACGGTAGTAACTGGTC CCTCGGTCATGAGTAT GAC- TACTGGGGCCAGGGGACCCAGGT- CACCGTCTCCTCAGAACCCAAGACACCAAAA CCACAA

New Anthrax EF/LF-Binding (Cross-Specific) VHHs

JMO-G1, SEQ ID NO: 91
QVQLVETGGGLVQPGGSLRLSCAASGSISSI- NAMGWYRQAPGKQRELVAAITIRGNT VYGDSVKGRFTVSRD- NAKNTVYLQMNSLKPEDTAVYYCNAKSTPS- LYAAGYGVDYWG EGTLVTVSSEPKTPKPQ

SEQ ID NO: 92
CAGGTGCAGCTGGTGGAGACGGGGG- GAGGCTTGGTGCAGCCTGGGGGGTCTCTGAGA CTCTCCTGTGCAGCCTCTG- GAAGCATCTCCAGTATCAATGC- CATGGGCTGGTACCGC CAGGCTCCAGG- GAAGCAGCGCGAGTTGGTCGCGGCTATTACT ATTCGTGGTAACACA GTCTATGGAGACTCCGT- GAAGGGCCGATTCACCGTCTCCAGA- GACAACGCCAAGAAC ACGGTGTATCTGCAAATGAACAGCCT-

GAAACCTGAGGACACGGCCGTCTATTACTGT
AATGC-
CAAGTCGACCCCGAGCTTGTACGCCGCCGGC-
TACGGCGTGGACTACTGGGGC
GAAGGGACCCTAGT-
CACCGTCTCCTCAGAACCCAAGACAC-
CAAAACCACAA

JMO-C9, SEQ ID NO: 93
QVQLVETGGGLVQAGGSLRLSCAASGNISSI-
NAMAWYRQAPGQQRELVAGITSGGRT
QYTDSVKGRFTISRDNAKNTVYLQMESLKPED-
TAVYYCNAKSPPSTWATGGGMNYWG
KGTLVTVSSEPKTPKPQ

SEQ ID NO: 94
CAGGTGCAGCTGGTGGAGACGGGGG-
GAGGCTTGGTGCAGGCTGGGGGGTCTCT-
GAGA CTCTCCTGTGCAGCCTCTGGGAA-
CATCTCCAGTATCAATGCCATGGCCTGGTACC
GC
CAGGCTCCAGGGCAGCAGCGCGAGCTGGTCG
CAGGGATTACTAGTGGTGGCAGGACA
CAATATACAGACTCCGTGAAGGGCCGATTCAC-
CATCTCCAGAGACAACGCCAAGAAC
ACGGTGTATCTGCAAATGGAGAGTCT-
GAAACCTGAGGACACAGCCGTCTATTACTGT
AATGCAAAAGCCCTCCCAGTACCTGGGC-
CACGGGGGGGGGCATGAACTACTGGGGC
AAAGGGACCCTGGT-
CACCGTCTCCTCAGAACCCAAGACAC-
CAAAACCACAA

JMN-D10, SEQ ID NO: 95
QVQLVETGGALVQAGGSLRLSCAA-
SETSSVSLSWMGWYRQAPGKERELVAGINRDRP
KYKESVKGRFTISRDNAQNTVYLQMNSLKPED-
TAVYYCNTVPPRGDYWGQGTQVTVS SEP-
KTPKPQ

SEQ ID NO: 96
CAGGTGCAGCTGGTGGAGACAGGAG-
GAGCCTTGGTGCAGGCGGGGGGGTCTCT-
GAGA CTCTCCTGTGCAGCCTCTGAGA-
CATCTTCAGTATCGCTATCATGGATGGGCTGG
TAC CGCCAGGCTCCTGG-
GAAGGAGCGCGAGTTGGTCGCAGGCAT-
TAATCGTGATAGGCCA
AAGTATAAAGAGTCCGTGAAGGGCCGATT-
CACCATCTCCAGAGACAACGCCCAGAAT
ACGGTGTATCTGCAAATGAACAGCCT-
GAAACCTGAGGACACAGCCGTCTATTACTGT
AATACGGTTCCACCACGCGGCGAC-
TACTGGGGCCAGGGGACCCAGGT-
CACCGTCTCC TCAGAACCCAAGACAC-
CAAAACCACAA

JMN-E12, SEQ ID NO: 97
QVQLVESGGGLVQPGGSLRVSCVASGNIS-
SVAAMAWYRQRPEKRRELVAVITNSGGT
AYTDSVRGRFTISRDNVKSTVYLQMNNLKPED-
TAVYYCNARGLDAGSGRIDYWGQGT
QVTVSSEPKTPKPQ

SEQ ID NO: 98
CAGGTGCAGCTGGTGGAGTCCGGTG-
GAGGCTTGGTGCAGCCTGGGGGGTCTGAGA
GTCTCCTGTGTAGCCTCTGGAAA-
CATCTCCAGTGTCGCTGC-
CATGGCTGGTACCGC CAGA-
GACCAGAGAAGCGCCGCGAATTGGTCGCAG
TCATTACTAACAGCGGTGGCACA GCCTATACA-
GACTCCGTGAGGGGCCGATTCAC-
CATCTCCAGAGACAATGTCAAGTCA
ACGGTGTATCTACAAATGAATAACCT-
GAAACCTGAGGACACAGCCGTGTATTACTGT
AATGCGAGGGGGTTA-
GACGCCGGGTCAGGGCGCATTGAC-
TACTGGGGCCAGGGAACC CAGGT-
CACCGTCTCCTCAGAACCCAAGACACCAAAA
CCACAA

JMN-F1, SEQ ID NO: 99
QVQLVESGGGLAQTGGSLNLS-
CAASGPTFSGYGMGWFRQAPGKEREFLA-
VIRWSVGN TLYAESVKGRFTIS-
RDKVKNTGYLQIDNLKPEDTAVYYCAAGAYVT
TRSRDYAYWGQ GTQVTVSSEPKTPKPQ

SEQ ID NO: 100
CAGGTGCAGCTGGTGGAGTCGGGGGGAGGAT-
TGGCGCAGACTGGGGGCTCTCTGAAC
CTCTCCTGTGCAGCCTCTGGACCGACTTTCA
GCGGCTATGGTATGGGCTGGTTCCGC
CAGGCTCCAGGGAAGGAGCGTGAAT-
TTCTAGCGGTAATTCGCTGGAGTGTAGGTAAT
ACATTGTATGCAGAGTCCGTCAAGGGCCGATT-
CACCATCTCCAGAGACAAGGTCAAG
AACACGGGTATCTGCAAATAGACAACCT-
GAAACCCGAGGACACGGCCGTTTATTAC
TGTGCAGCGGGGGCGTACGTAAC-
TACGAGGTCCCGCGACTATGCC-
TACTGGGGCCAG GGGACCCAGGT-
CACCGTCTCCTCAGAACCCAAGACACCAAA
ACCACAA

JLO-A4, SEQ ID NO: 101
QVQLVETGGRQVQTGDSLNLS-
CAASEHTFSPKVMGWFRQAPGKGREFVATITIR-
GGR TLYADSVKGRFAISKD-
GAKNTVYLQMNSLKPEDTAVYYCAASRELAIP
PTQPSAYDH WGQGTQVTVSSAHHSEDPS

SEQ ID NO: 102
CAGGTGCAGCTCGTGGA-
GACCGGCGGACGTCAGGTGCA-
GACTGGGGACTCTCTGAAC
CTCTCTTGCGCAGCTTCT-
GAACACACCTTCAGTCCTAAAGT-
TATGGGGTGGTTCCGC
CAGGCTCCAGGCAAGGGGCGT-
GAGTTTGTAGCAACTAT-
CACAATCCGTGGCGGTCGC ACACTCTATGCA-
GATTCCGTGAAGGGCCGATTTGCCATCTCCA
AAGACGGCGCCAAG
AATACGGTGTATCTGCAAATGAACAGTCT-
GAAACCTGAGGACACGGCCGTTTATTAC
TGTGCAGCAAGTCGTGAGCTAGCGATAC-
CACCGACGCAGCCTTCGGCATACGACCAC
TGGGGCCAGGGGACCCAGGT-
CACCGTCTCCTCAGCGCACCACAGCGAA-
GACCCCTCG

Appendix D

Included in Appendix D are 2 Anthrax PA-Binding VNAs
New Anthrax PA-Binding VNAs
VNA1-PA (JKD-11) SEQ ID NO:103
QVQLAESGGGLVQPGGSLGLSCVVASERSIN-
NYGMGWYRQAPGKQRELVAQISSGGT TNY-
ADSVEGRFTISRDNVKKMVHLQVNSLKPED-
TAVYYCNSLLRTFSWGQGTQVTVS
SEPKTPKPQA-
IAGGGGSGGGGSGGGGSLQGQVQLVESGG-
GLVQPGGSLSVSCAASGS IARP- GAMAWYRQAPGKERELVASITPGGLTNYADSVTGRFTISRDNAKRTVYLQMNS LQPEDTAVYYCHARIIPLGLGSEYRDHWGQGTQVTVSSAHHSEDPS SEQ ID NO: 104
CAGGTGCAGCTGGCGGAGTCGGGCGGAGGCTTGGTGCAGCCTGGGGGGTCTCTGGACTCTCCTGTGTAGTCGCCTCTGAAAGAAGCATCAATAATTATGGCATGGGCTGGTAC CGCCAGGCTCCAGGGAAGCAGCGCGAGTTGGTCGCGCAAATTAGTAGTGGTGGTACC ACAAATTATGCAGACTCCGTAGAGGGCCGATTCACCATCTCCA GAGACAACGTCAAG AAAATGGTGCATCTTCAAGTGAACAGCCTGAAACCTGAGGACACGGCCGTCTATTAC TGTAATTCGCTACTCCGAACTTTTTCCTGGGGCCAGGGGAC CCAGGTCACCGTCTCC TCGGAACCCAAGACACCAAAACCACAAGCGATCGCTGGTGGAGGCGGTTCAGGCGGA GGTGGCTCTGGCGGTGGCGGTTCCCTGCAGG GTCAGKTGCAGCTSGYGGAGTCCGGG GGCGGCTTGGTGCAGCCGGGGGGTCTCTGAGTGTCTCCTGTGCAGCCTCTGGAAGC ATCGCAAGACCAGGTGCCATGGCCTGGTACCGCCAGGCTCCAGGGAAGGAGCGCGAG TTGGTCGCGTCTATTACGCCTGGTGGTCTTACAAACTATGCGGACT CCGTGACGGGC CGATTCACCATTTCCAGAGACAACGCCAAGAGGACGGTGTATCTGCAGATGAACAGC CTCCAACCCGAGGACACGGCCGTCTATTACTGTCATGCACGAATAATTCCCCTAGGA CTTGGGTCCGAATACAGGGACCACTGGGGCCAGGGGACTCAGGTCACCGTCTCCTCA GCGCACCACAGCGAAGACCCCTCG VNA2-PA (JKU-1) SEQ ID NO: 105
QVQLAESGGGLVQPGGSLGLSCVVASERSINNYGMGWYRQAPGKQRELVAQISSGGT TNYADSVEGRFTISRDNVKKMVHLQVNSLKPEDTAVYYCNSLLRTFSWGQGTQVTVS SEPKTPKPQA-IAGGGGSGGGGSGGGGSLQGQVQLAESGGGGLVQAGGSLRLSCAASG RTFSGYAMGWFRQAPGKEREFVADISWSGHNTYYGD SVKGRFTISRDTAKNTVYLQM NSLKPEDTAVYYCAAEGARTHLSDSYYFPGLWAEPPVGYWGQGTQVTVSSEPKTPKP Q SEQ ID NO: 106
CAGGTGCAGCTGGCGGAGTCGGGCGGAGGCTTGGTGCAGCCTGGGGGGTCTCTGGACTCTCCTGTGTAGTCGCCTCTGAAAGAAGCATCAATAATTATGGCATGGGCTGGTAC CGCCAGGCTCCAGGGAAGCAGCGCGAGTTGGTCGCGCAAATTAGTAGTGGTGGTACC ACAAATTATGCAGACTCCGTAGAGGGCCGATTCACCATCTCCA GAGACAACGTCAAG AAAATGGTGCATCTTCAAGTGAACAGCCTGAAACCTGAGGACACGGCCGTCTATTAC TGTAATTCGCTACTCCGAACTTTTTCCTGGGGCCAGGGGAC CCAGGTCACCGTCTCC TCGGAACCCAAGACACCAAAACCACAAGCGATCGCTGGTGGAGGCGGTTCAGGCGGA GGTGGCTCTGGCGGTGGCGGTTCCCTGCAGG GTCAGGTGCAGCTCGCGGAGTCGGGT GGGGGAGGACTGGTGCAGGCTGGGGGCTCTCTGAGACTCTCCTGTGCAGCCTCTGGA CGCACCTTCAGTGGCTATGCCATGGGCTGGTTCCGCCAGGCTCCGGGGAAGGAGCGT GAGTTTGTAGCCGATATTAGCTGGAGTGGTCATAACACGTACTATGGAGACTCCGTG AAGGGCCGATTCACCATCTCCAGAGACACCGCCAAGAACACGGTGTATCTGCAAATG AACAGCCTGAAACCTGAGGACACGGCCGTTTATTACTGTGCAGCGGAGGGGCCCGT ACACACCTTAGTGATAGTTACTACTTCCCGGGCCTCTGGGCCGAACCCCCCG TGGGC TACTGGGGCCAGGGGACCCAGGTCACTGTCTCCTCAGAACCCAAGACACCAAAACCA CAA Appendix E Included in Appendix E are 10 BoNT/B-protease light chain (BLc) binding VHHs; 2 BoNT/E-protease light chain (ELc) binding VHHs; 4 BoNT/B-binding VHH heterodimers; and 3 BoNT/E-binding VHH heterodimers.

New BoNT/B-Protease Light Chain (BLc) Binding VHHs

JLS-G8, SEQ ID NO: 107
QVQLVESGGGSVQAGGSLRLTCTGSGRSFALYYMAWFRQAPGKEREFVAAISHNSLSAIV ADSLKGRFTISRDNARNQVVLQMNSLKPEDTAVYYCAADFSPSTYNTNYYRTGSYQYWGQ GTQVTVSSEPKTPKPQ

SEQ ID NO: 108
CAGGTGCAGCTGGTGGAGTCGGGGGGAGGATCGGTGCAGGCTGGGGGCTCTCTGAGACTCACCTGTACAGGCTCTGGACGCAGTTTCGCGCTCTATTACATGGCCTGGTTCCGCCAGGCT CCAGGGAAGGAGCGTGAGTTTGTAGCAGCTATCAGCCACAATTCGTTAAGCGCAATCGTT GCAGACTCCCTAAAGGGCCGATTCACCATCTCCAGAGACAACGCCAGAAACCAGGTGGTT CTACAAATGAACAGCCTGAAACCTGAGGACACGGCCGTTTATTACTGTGCAGCAGACTTT TCGCCCTCGACCTATAATACAAATTACTACCGCACCGGTTCGTATCAGTATTGGGGCCAG GGGACCCAGGTCACCGTCTCCTCAGAACCCAAGACACCAAAACCACAA

JND-A12, SEQ ID NO: 109
QVQLVETGGGLVQAGGSLGLSCAASGLSFNWYDVGWFRQAPGKEREFVASRSSGGGSTYY GDSVKGRFSISTDNAKNTAYLQMNSLKPEDTAVYYCAADWTGRAGFSVGYY RPDEYDYWG QGTQVTVSEEPKTPKPQ

SEQ ID NO: 110
CAGGTGCAGCTGGTGGAGACGGGAGGAGGATTGGTGCAGGCTGGGGGCTCTCTGGGACTC TCCTGTGCAGCCTCTGGACTGTCCTTTAATTGGTATGACGTGGGCTGGTTCCGCCAGGCT CCAGGGAAGGAGCGTGAGTTTGTAGCGTCTCGTAGCTCGGGTGGTGGTAGTACATATTAT GGAGACTCCGTGAAGGGCCGATTCAGCATCTCCACAGACAATGCCAAGAACACGGCGTAT CTGCAAATGAACAGCCTAAAACCTGAGGACACGGCCGTTTACTACTGTGCAGCAGATTGG ACAGGCCGCGCAGGCTTCAGTGTTGGTTAC-

JND-B4, SEQ ID NO: 111
  QVQLVETGGGLVQPGGSLRLSCVASGFTLDSYAIGWFRQAPGKEREGVSCMSSGDGSTYY TNSVKGRFTISRDNAQNTVYLQMNSLKPEDTAVYYCAADGFDYCSAYVPGRGMNYSGKGT LVTVSSEPKTPKPQ

SEQ ID NO: 112
  CAGGTGCAGCTGGTGGAGACGGGGGGAGGCTTGGTGCAGCCTGGGGGGTCTCTGAGACTC TCCTGTGTAGCCTCTGGATTCACTTTGGATTCATATGCCATAGGCTGGTTCCGCCAGGCC CCAGGGAAGGAGCGTGAGGGGGTCTCATGTATGAGTAGTGGTGATGGTAGCACATACTAT ACAAACTCCGTGAAGGGCCGATTCACCATCTCCAGAGACAACGCCCAGAACACGGTG TAT CTGCAAATGAACAGCCTGAAACCTGAGGACACAGCCGTTTATTACTGTGCAGCAGATGGG TTTGACTATTGTTCAGCTTATGTGCCCGGGAGAGGCATGAACTACTCGG GCAAAGGGACC CTGGTCACCGTCTCCTCAGAACCCAAGACACCAAAACCACAA

JND-C7, SEQ ID NO: 113
  QVQLVETGGGLVQPGGSLRLSCAGSGFTLDNYAVGWFRQAPGKEREGVSCISSSDDNTDY SDSVKGRFTISRDNAKDTVYLQMNSLKPEDTAIYYCAAESPTFGFSCTVATDPYDYWGQG TQVTVSSEPKTPKPQ

SEQ ID NO: 114
  CAGGTGCAGCTGGTGGAGACGGGTGGAGGCTTGGTGCAGCCTGGGGGGTCTCTGAGACTC TCCTGTGCAGGCTCTGGATTCACTTTGGATAATTATGCCGTCGGCTGGTTCCGCCAGGCC CCAGGGAAGGAGCGTGAGGGGGTCTCATGTATTAGTAGTAGTGATGATAACACTGACTAT TCAGACTCCGTGAAGGGCCGATTCACCATCTCCAGAGACAACGCCAAGGACACGGTCTAT CTGCAAATGAACAGCCTGAAACCTGAGGACACAGCGATTTATTACTGTGCAGCAG AAAGCCCGACGTTCGGGTTCAGCTGTACGGTAGCCACTGATCCATATGACTACTGGGGCCAGGGG ACCCAGGTCACCGTCTCCTCAGAACCCAAGACACCAAAACCACAA

JND-E4, SEQ ID NO: 115
  QVQLVETGGGLVQPGGSLRLSCAASGFTLDGYAAGWFRQAPGKERELVSWISSTDGSTYY AASVKGRFTVSRDNAKNTVYLQMNSLKPEDTAVYYCTAGLGLDVSDYVYDYWGQGTQVTV SSEPKTPKPQ

SEQ ID NO: 116
  CAGGTGCAGCTGGTGGAGACGGGGGGAGGCTTGGTGCAGCCTGGGGGGTCTCTGAGGCTC TCCTGTGCAGCCTCTGGATTCACTTTGGATGGCTATGCCGCAGGCTGGTTCCGCCAGGCC CCAGGGAAGGAGCGTGAGTTGGTCTCATGGATTAGTAGCACTGATGGTAGCACATACTAT GCAGCCTCCGTGAAGGGCCGATTCACCGTCTCCAGAGACAACGCCAAGAACACGGTGTAT CTACAAATGAACAGCCTGAAACCTGAGGACACAGCCGTTTATTACTGTACAGCAGGTCTA GGGCTTGACGTTAGCGACTATGTATATGACTACTGGGGCCAGGGGACCCAGGTCACCGTC TCCTCAGAACCCAAGACACCAAAACCACAA

JND-E5, SEQ ID NO: 117
  QVQLVESGGGLVQPGGSLRLSCAASGFTLDYYGIGWVRQAPGKEREEVSCITSGGLTNYPD SVKGRFTISRDNAKNTVYLQMNSLKPEDTAVYYCAIDRVGVCAMEDFGSWGQGTQVTVSS EPKTPKPQ

SEQ ID NO: 118
  CAGGTGCAGCTGGTGGAGTCGGGCGGCTTGGTGCAGCCTGGGGGGTCTCTGAGACTCTCC TGTGCAGCCTCTGGATTCACTTTGGATTATTATGGCATAGGCTGGGTCCGCCAGGCCCCA GGGAAGGAGCGTGAGGAGGTCTCATGTATTACTAGTGGTGGTCTCACAAACTATCCAGAC TCCGTGAAGGGCCGATTCACCATCTCCAGAGACAACGCCAAGAACACAGTGTATCTGCAA ATGAACAGCCTGAAACCTGAGGACACGGCCGTTTATTACTGTGCAATCGACCGTGTGGGA GTATGCGCGATGGAGGACTTTGGTTCCTGGGGCCAGGGGACCCAGGTCACCGTCTCCTCG GAACCCAAGACACCAAAACCACAA

JND-E9, SEQ ID NO: 119
  QVQLVETGGGLVQAGDSLRLSCAASGRTFNYYAMAWFRQAPGKEREFVAFINWSGDSTYY AGSVKGRFTISRDNAKNTVYLQMNNLKPEDTAVYSCAAEFGTFSYLQGDDYSYWGQGTQV TVSSEPKTPKPQ

SEQ ID NO: 120
  CAGGTGCAGCTGGTGGAGACAGGTGGAGGATTGGTGCAGGCTGGGGACTCTCTGAGACTC TCCTGTGCAGCCTCTGGACGCACCTTCAATTACTATGCCATGGCCTGGTTCCGCCAGGCC CCAGGAAAGGAGCGTGAATTTGTAGCATTTATTAACTGGAGCGGCGATAGTACATACTAT GCAGGCTCCGTGAAGGGCCGATTCACCATCTCCAGAGACAACGCCAAGAACACGGTGTAT CTGCAAATGAACAACCTGAAACCTGAGGACACGGCCGTTTATTCCTGTGCAGCAGAATTC GGTACATTTCCTACTTGCAAGGCGATGACTATAGCTACTGGGGCCAGGGGACCCAGGTC ACCGTCTCCTCAGAACCCAAGACACCAAAACCACAA

JND-F3, SEQ ID NO: 121
  QVQLVESGGGLVQAGGSLRLSCAASGRSFSSYRMGWFRQAPGKERELVAGISWSGSSTWY ADSVKGRFTISRDNAKNTVYLQMNSLKPEDTAVYYCAADGLGTDWSDAIWDYWGQGTQVT VSSEPKTPKPQ

SEQ ID NO: 122
  CAGGTGCAGCTGGTGGAGTCTGGAGGAGGATTGGTGCAGGCTGGGGGCTCTCTGAGACTC TCCTGTGCAGCCTCTGGACGCAGCTTCAGTAGCTATCGCATGGGCTGGTTCCGCCAGGCT CCAGGGAAGGAGCGTGAGCTTGTAGCAGGTATTAGCTGGAGTGGAAGTAGTACATGGTAT GCAGACTCCGTGAAGGGCCGATTCACCATCTCCAGAGACAACGCCAAGAACACGGTGTAT CTGCAAATGAACAGCCTGAAACCCGAGGACACGGCCGTTTATTACTGTGCACAGGATGGG CTAGGGACGGATTGGAGCGATGCCATATGGGACTACTGGGGCCAGGGGACCCAGGTCACC GTCTCCTCAGAACCCAAGACACCAAAACCACAA

JND-F7, SEQ ID NO: 123
QVQLVESGGGLVQAGGSLRLSCAASGRNFSHY-AMGWFRQAPGKAREFVATINRDGDSTYY TNSVKGRFTISRENAKNTGYLQMNSLKPED-TAVYYCGVQYSWSGTSIYWREYEYAYWGQGAQVTVSSEPKTPKPQ

SEQ ID NO: 124
CAGGTGCAGCTGGTGGAGTCGGGGGGAGGATTGGTGCAGGCTGGGGGCTCTCTGAGACTCTCCTGTGCAGCCTCTGGACGCAATTTCAGTCACTATGCCATGGGCTGGTTCCGCCAGGCTCCAGGGAAGGCGCGTGAGTTTGTAGCAACTATTAACCGGGATGGTGATAGCACATACTATACGAACTCCGTGAAGGGCCGATTCACCATCTCCAGAGAGAACGCCAAGAACACGGGATAT CTGCAAATGAACAGCCTGAAACCTGAGGACACGGCCGTTTATTACTGTGGAGTACAATAC TCGTGGTCGGGTACAAGTATTTACTGGAGGGAGTATGAGTATGCCTACTGGGGCCAGGGG GCCCAGGTCACCGTCTCCTCAGAACCCAAGACACCAAAACCACAA

JNE-B10, SEQ ID NO: 125
QVQLVESGGGLVQPGGSLRLSCAASGFPF-HAYYMSWVRQAPGKGLEWVSHIGNGGIITRYADSVKGRFTISRDNAKNTLYLQMTNLKPED-TALYYCTLGTRDDLGPERGQGTQVTVSSEPKTPKPQ

SEQ ID NO: 126
CAGGTGCAGCTGGTGGAGTCGGGTG-GAGGCTTGGTGCAGCCTGGGGGGTCTCTGAGACTC TCCTGTGCAGCCTCTGGATTCCCCTTCCATGCCTACTACATGAGCTGGGTCCGCCAGGCTCCAGGAAAGGGGCTCGAGTGGGTCTCCCATATTGGCAATGGTGGTATTATTACACGCTAT GCAGACTCCGTGAAGGGCCGGTTCACCATCTCCAGAGACAACGCCAAGAACACGCTGTAT CTGCAAATGACCAACCTGAAACCTGAGGACACGGCCCTGTATTATTGTACCCTGGGGACCCGCGACGACCTGGGGCCTGAGAGGGGCCAGGGGACCCAGGTCACCGTCTCCTCAGAACCC AAGACACCAAAACCACAA

New BoNT/E-Protease Light Chain (ELc) Binding VHHs
JNB-B12, SEQ ID NO: 127
QVQLVESGGGLVQPGGSLRLSCAASE-GIFSVDAMGWYRQVPGKQRELVARITRGGSIIYADSVKGRFTISRDSAKNTVYLQMNSLKPED-TAVYYCNRLYRGTLTFGQGTQVTVSSAHHSEDPS SEQ ID NO: 128
CAGGTGCAGCTCGTGGAGTCGGGTG-GAGGCTTGGTGCAGCCTGGGGGGTCTCTGAGACTC TCCTGTGCAGCCTCTGAGGGAATCTTCAGTGTTGATGCCATGGGCTGGTACCGCCAGGTT CCAGGGAAGCAGCGCGAGTTGGTCGCACGAATTACCCGTGGTGGTAGCATAATTTATGCAGACTCCGTGAAGGGCCGATTCACCATCTCCAGAGACAGCGCCAAGAACACGGTGTATCTG CAAATGAACAGCCTGAAACCTGAGGACACGGCCGTCTATTACTGTAATCGCCTTTATAGGGGTACCCTAACGTTCGGCCAGGGGACCCAGGTCACCGTCTCCTCAGCGCACCACAGCGAAGACCCCTCG JNC-D5, SEQ ID NO: 129
QVQLVETGGGLVQAGGSLRLSCAASGRTFSI-QVQLVETGGGLVQAGGSLRLSCAASGRTFSI-YAMGWFRQAPGREREFVASISRMGWSTYYGDSVKGRFTASRDNAKNTLYLQMNSLELED-TAVYFCAASASALRVNQWDYWGQGTQVTVSSEPKTPKPQ SEQ ID NO: 130
CAGGTGCAGCTGGTGGAGACCGGCGGAGGATTGGTGCAGGCTGGGGGCTCTCTGAGACTCTCCTGTGCAGCCTCTGGACGCACCTTCAGTATCTATGCCATGGGCTGGTTCCGCCAGGCTCCAGGGAGGGAGCGTGAGTTTGTAGCGTCTATTAGTCGGATGGGTTGGAGCACATATTATGGGGACTCCGTGAAGGGCCGATTCACCGCCTCCAGAGACAACGCCAAGAACACGCTGTAT CTACAAATGAACAGCCTCGAACTTGAGGACACGGCCGTATATTTTTGTGCGGCATCTGCGAGTGCGTTACGAGTTAATCAGTGGGACTACTGGGGCCAGGGGACCCAGGTCACCGTCTCC TCAGAACCCAAGACACCAAAACCACAA New BoNT/B-Binding VHH Heterodimers
JLU-D10/JLI-G10, SEQ ID NO: 131
QVQLVESGGGLVQPGGSLRLS-CAASGFTLDSYAIGWFRQAPGKEREGVA-CISASGSGTDYVDSVKGRFTVSRDQAKSMVFLQMNNMKPED-AAVYYCAADYRPRPLPIQAPCTMTGGNYWGQGTQVTVSSEPKTPKPQA-IAGGGGSGGGGSGGGGSLQGQVQLVESGG-GLVQAGGSLRLSC AASILTY-DLDYYYIGWVRQAPGKEREGVSCISSTDGATYYADSVKGRFTISRNNAKNTVY LQMNNLKPED-TAIYY-CAAAPLAGRYCPASHEYGYWGQGTQVTVS-SAHHSEDPS SEQ ID NO: 132
CAGGTGCAGCTCGTGGAGTCAGGGG-GAGGCTTGGTGCAGCCTGGGGGGTCTCTGAGACTC TCCTGTGCAGCCTCTGGATTCACTTTAGATAGTTATGCAATAGGCTGGTTCCGCCAGGCCCCAGGGAAGGAGCGTGAGGGGGTCGCATGTATTAGTGCTAGTGGTAGTGGCACGGACTAT GTAGACTCCGTGAAGGGCCGATTCACCGTCTCCAGAGACCAGGCCAAGAGCATGGTGTTT CTGCAAATGAACAACATGAAACCTGAGGACGCAGCCGTTTATTACTGTGCAGCAGATTAT CGGCCGAGGCCCCTGCCGATTCAGGCGCCGTGTACAATGACAGGTGGCAACTACTGGGGC CAGGGGACCCAGGTCACCGTCTCCTCAGAACCCAAGACACCAAAACCACAAGCGATCGCT GGTGAGGCGGTTCAGGCGGAGGTGGCTCTGGCGGTGGCGGTTCCCTGCA GGGTCAGGTG CAGCTCGTGGAGTCCGGTGGAGGCTTGGTGCAGGCTGGGGGGTCTCTGAGACTCTCCTGT GCAGCCTCTATACTCACTTATGATTTGGATTATTACATAGGCTGGGTCCGCCAGGCC CCAGGGAAGGAGCGTGAGGGGGTCTCATGTATTAGTAGTACTGATGGTGCCACATACTAT GCAGACTCCGTGAAGGGCCGATTCACCATCTCCAGAAACAACGCCAAGAACACGGTGTAT CTGCAAATGAACAACCTAAAACCTGAGGACACAGCCATTTATTATTGTGCAGCAGCCCCCCTGGCTGGGCGCTACTGTCCCGCCTCGCAT

GAGTATGGCTACTGGGGTCAGGGGACCCAGGTCACCGTCTCGTCAGCGCACCACAGCGAAGACCCCTCG

JLU-D10/JLK-G12, SEQ ID NO: 133

QVQLVESGGGLVQPGGSLRLSCAASGFTLDSYAIGWFRQAPGKEREGVACISASGSGTDYVDSVKGRFTVSRDQAKSMVFLQMNNMKPEDAAVYYCAADYRPRPLPIQAPCTMTGGNYWGQGTQVTVSSEPKTPKPQAIAGGGGSGGGGSGGGGSLQGQXQLXESGGGLVQAGGSLRLSC AASEFRAEHFAVGWFRQAPGKEREGVSCVDASGDSTAYADSVKGRFTISRDNNKNVVYLQMDSLEPEDTGDYYCGASYFTVCAKSMRKIEYRYWGQGTQVTVSSEPKTPKPQ

SEQ ID NO: 134

CAGGTGCAGCTCGTGGAGTCAGGGGGAGGCTTGGTGCAGCCTGGGGGGTCTCTGAGACTC TCCTGTGCAGCCTCTGGATTCACTTTAGATAGTTATGCAATAGGCTGGTTCCGCCAGGCCCCAGGGAAGGAGCGTGAGGGGTCGCATGTATTAGTGCTAGTGGTAGTGGCACGGACTATGTAGACTCCGTGAAGGGCCGATTCACCGTCTCCAGAGACCAGGCCAAGAGCATGGTGTTT CTGCAAATGAACAACATGAAACCTGAGGACGCAGCCGTTTATTACTGTGCAGCAGATTAT CGGCCGAGGCCCCTGCCGATTCAGGCGCCGTGTACAATGACAGGTGGCAACTACTGGGGC CAGGGGACCCAGGTCACCGTCTCCTCAGAACCCAAGACACCAAAACCACAAGCGATCGCT GGTGGAGGCGGTTCAGGCGGAGGTGGCTCTGGCGGTGGCGGTTCCCTGCA GGGTCAGKTG CAGCTSGYGGAGTCCGGTGGAGGCTTGGTGCAGGCTGGGGGGTCTCTGAGACTCTCCTGT GCAGCCTCTGAATTCCGTGCGGAGCATTTTGCCGTGGGCTGGTTCCGCCAGGCCCCAGGG AAGGAGCGTGAGGGGTCTCATGTGTAGACGCGAGTGGTGATAGTACAGCATATGCGGAC TCTGTGAAGGGCCGATTCACCATCTCCAGAGACAACAACAAGAACGTAGTGTATCTGCAA ATGGACAGCCTGGAACCTGAAGACACAGGAGATTATTATTGTGAGCCTCGTACTTTACT GTCTGCGCCAAGAGCATGCGGAAAATTGAATATAGGTACTGGGGCCAGGGGACCCAGGTC ACCGTCTCCTCAGAACCCAAGACACCAAAACCACAA

JLI-G10/JLO-G11, SEQ ID NO: 135

QVQLVESGGGLVQAGGSLRLSCAASILTYDLDYYYIGWVRQAPGKEREGVSCISSTDGATYYADSVKGRFTISRNNAKNTVYLQMNNLKPEDTAIYYCAAAPLAGRYCPASHEYGYWGQGTQVTVSSAHHSEDPSAIAGGGGSGGGGSGGGGSLQGQVQLVESGGGLVQPGGSLRLSCEA SGFHLEHFAVGWFRQAPGKEREGVSCISASGDSTTYADSVKGRSTISKDNAKNAVYLQMDSLRPEDTGDYYCAASHFSVCGKNIRKIEYRYWGQGTPVTVSSEPKTPKPQ

SEQ ID NO: 136

CAGGTGCAGCTGGTGGAGTCCGGTGGAGGCTTGGTGCAGGCTGGGGGGTCTCTGAGACTC TCCTGTGCAGCCTCTATACTCACTTATGATTTGGATTATTATTACATAGGCTGGGTCCGC CAGGCCCCAGGGAAGGAGCGTGAGGGGTCTCATGTATTAGTAGTACTGATGGTGCCACA TACTATGCAGACTCCGTGAAGGGCCGATTCACCATCTCCAGAAACGCCAAGAACACG GTGTATCTGCAAATGAACAACCTAAAACCTGAGGACACAGCCATTTATTATTGTGCAGCA GCCCCCCTGGCTGGGCGCTACTGTCCCGCCTCGCATGAGTATGGCTACTGGGGTCAGGGG ACCCAGGTCACCGTCTCGTCAGCGCACCACAGCGAAGACCCCTCGGCGATCGCTGGTGGA GGCGGTTCAGGCGGAGGTGGCTCTGGCGGTGGCGGTTCCCTGCA GGGTCAGGTGCAGCTG GTGGAGTCGGTGGAGGCTTGGTGCAGCCTGGGGGGTCTCTGAGACTCTCCTGTGAAGCC TCAGGATTCCATTTGAGCATTTTGCCGTAGGCTGGTTCCGCCAGGCCCCAGGGAAGGAG CGTGAGGGGTCTCATGTATAAGCGCGAGTGGTGATAGTACAACGTATGCAGACTCCGTG AAGGGCCGATCCACCATCTCCAAAGACAACGCCAAGAACGCGGTGTATCTGCAAATGGAC AGCCTGAGACCCGAGGACACAGGCGATTATTACTGTGCAGCCTCGCACTTCAGTGTCTGC GGCAAGAACATTCGGAAAATTGAGTATAGGTACTGGGGCCAGGGGACCCCGGTCACCGTC TCCTCAGAACCCAAGACACCAAAACCACAA

JLI-G10/JLK-G12, SEQ ID NO: 137

QVQLVESGGGLVQAGGSLRLSCAASILTYDLDYYYIGWVRQAPGKEREGVSCISSTDGATYYADSVKGRFTISRNNAKNTVYLQMNNLKPEDTAIYYCAAAPLAGRYCPASHEYGYWGQGTQVTVSSAHHSEDPSAIAGGGGSGGGGSGGGGSLQGQVQLAESGGGLVQAGGSLRLSCAA SEFRAEHFAVGWFRQAPGKEREGVSCVDASGDSTAYADSVKGRFTISRDNNKNVVYLQMDSLEPEDTGDYYCGASYFTVCAKSMRKIEYRYWGQGTQVTVSSEPKTPKPQ

SEQ ID NO: 138

CAGGTGCAGCTGGTGGAGTCCGGTGGAGGCTTGGTGCAGGCTGGGGGGTCTCTGAGACTC TCCTGTGCAGCCTCTATACTCACTTATGATTTGGATTATTATTACATAGGCTGGGTCCGC CAGGCCCCAGGGAAGGAGCGTGAGGGGTCTCATGTATTAGTAGTACTGATGGTGCCACA TACTATGCAGACTCCGTGAAGGGCCGATTCACCATCTCCAGAAACAACGCCAAGAACACG GTGTATCTGCAAATGAACAACCTAAAACCTGAGGACACAGCCATTTATTATTGTGCAGCA GCCCCCCTGGCTGGGCGCTACTGTCCCGCCTCGCATGAGTATGGCTACTGGGGTCAGGGG ACCCAGGTCACCGTCTCGTCAGCGCACCACAGCGAAGACCCCTCGGCGATCGCTGGTGGA GGCGGTTCAGGCGGAGGTGGCTCTGGCGGTGGCGGTTCCCTGCA GGGTCAGGTGCAGCTG GCGGAGTCCGGTGGAGGCTTGGTGCAGGCTGGGGGGTCTCTGAGACTCTCCTGTGCAGCC TCTGAATTCCGTGCGGAGCATTTTGCCGTGGGCTGGTTCCGCCAGGCCCCAGGGAAGGAG CGTGAGGGGTCTCATGTGTAGACGCGAGTGGTGATAGTACAGCATATGCGGACTCTGTG AAGGGCCGATTCACCATCTCCAGAGACAACAACAAGAACGTAGTGTATCTGCAAATGGAC AGCCTGGAACCTGAAGACACAGGAGATTATTATTGTGAGCCTCGTACTTTACTGTCTGC GCCAAGAG

CATGCGGAAAATTGAATATAGGTACTGGGGCCAGGGGACCCAGGTCACCGTC TCCTCAGAACCCAAGACACCAAAACCACAA

New BoNT/E-Binding VHH Heterodimers

JLE-E5/JLE-E9, SEQ ID NO: 139
QVQLVETGGGLVQAGGSLRLSCAASGRSYAMGWFRQGPGKEREFVATISWSSTNTWYADS VKGRFTISRDNAKNTVYLQMNSLKPEDTAVYYCAASHRFSDYPMRSEDGMDYWGKGTLVT VSSEPKTPKPQAIAGGGGSGGGGSGGGGSLQGQVQLVETGGGLVQAGGSLRLSCAASGRT FSSYSMGWFRQAPGKEREYVAAVNSNGDSTFYADSIKGRFTVSRDAAKNTVYLQMNSLKP EDTALYYCAAVYGRYTYQSPKSYEYWGQGTQVTVSSEPKTPKPQ

SEQ ID NO: 140
CAGGTGCAGCTGGTGGAGACGGGGGGAGGATTGGTGCAGGCTGGGGGCTCTCTGAGACTCTCCTGTGCAGCCTCTGGACGCAGTTATGCCATGGGCTGGTTCCGCCAGGGTCCAGGGAAGGAGCGTGAGTTTGTAGCCACTATCAGTTGGAGTAGTACTAACACATGGTATGCAGATTCCGTGAAGGGCCGATTCACCATCTCTAGAGACAACGCCAAGAACACGGTGTATCTGCAAATGAACAGCCTGAAACCTGAGGACACGGCTGTTTATTACTGTGCAGCGAGCCATCGTTTTAGC GACTATCCCATGAGGTCAGAGGACGGCATGGACTACTGGGGCAAAGGGACCCTGGTCACCGTCTCCTCAGAACCCAAGACACCAAAACCACAAGCGATCGCTGGTGGAGGCGGTTCAGGCGGAGGTGGCTCTGGCGGTGGCGGTTCCCTGCAGGGTCAGGTGCAGCTGGTGGAGACGGGAGGAGGATTGGTGCAGGCTGGGGGCTCTCTGAGACTCTCGTGTGCAGCCTCTGGACGCACCTTCAGTAGCTATTCCATGGGCTGGTTCCGCCAGGCTCCAGGGAAGGAGCGTGAGTATGTA GCAGCAGTTAACTCCAATGGCGACAGTACATTCTATGCCGACTCCATTAAGGGCCGATTC ACCGTCTCCAGAGACGCGCCAAGAACACAGTCTATCTGCAAATGAACAGCCTGAAACCT GAGGACACGGCCGTCCTT TATTACTGTGCAGCTGTCTACGGTAGATACACTTACCAGTCCCCA AAATCGTATGAGTACTGGGGCCAGGGGACCCAGGTCACCGTCTCCTCAGAACCCAAGACACCAAAACCACAA

JLE-E5/JLE-G6, SEQ ID NO: 141
QVQLVETGGGLVQAGGSLRLSCAASGRSYAMGWFRQGPGKEREFVATISWSSTNTWYADS VKGRFTISRDNAKNTVYLQMNSLKPEDTAVYYCAASHRFSDYPMRSEDGMDYWGKGTLVT VSSEPKTPKPQAIAGGGGSGGGGSGGGGSLQGQVQLVETGGGLVKPGGSLRLSCVVSGFT FDDYRMAWVRQAPGKELEWVSSIDSWSINTYYEDSVKGRFTISTDNAKNTLYLQMSSLKP EDTAVYYCAAEDRLGVPTINAHPSKYDYNYWGQGTQVTVSSEPKTPKPQ

SEQ ID NO: 142
CAGGTGCAGCTGGTGGAGACGGGGGGAGGATTGGTGCAGGCTGGGGGCTCTCTGAGACTCTCCTGTGCAGCCTCTGGACGCAGTTATGCCATGGGCTGGTTCCGCCAGGGTCCAGGGAAGGAGCGTGAGTTTGTAGCCACTATCAGTTGGAGTAGTACTAACACATGGTATGCAGATTCCGTGAAGGGCCGATTCACCATCTCTAGAGACAACGCCAAGAACACGGTGTATCTGCAAATGAACAGCCTGAAACCTGAGGACACGGCTGTTTATTACTGTGCAGCGAGCCATCGTTTTAGC GACTATCCCATGAGGTCAGAGGACGGCATGGACTACTGGGGCAAAGGGACCCTGGTCACCGTCTCCTCAGAACCCAAGACACCAAAACCACAAGCGATCGCTGGTGGAGGCGGTTCAGGCGGAGGTGGCTCTGGCGGTGGCGGTTCCCTGCAGGGTCAGGTGCAGCTGGTGGAGACTGGTGGAGGCTTGGTGAAGCCTGGGGGTTCTCTGAGACTCTCCTGTGTAGTCTCCGGATTCACT TTTGATGATTATCGCATGGCTTGGGTCCGCCAGGCTCCAGGGAAGGAGCTGGAGTGGGTG TCCAGTATAGATAGTTGGAGTATCAACACATACTATGAAGACTCCGTGAAGGGCCGGTTC ACCATCTCCACAGACAACGCCAAGAATACACTGTATCTGCAAAT GAGCAGCCTGAAACCT GAGGACACGGCCGTGTATTACTGTGCAGCAGAGGACCGCTTAGGTGTACCGACTATTAAC GCCCACCCTTCAAAATATGATTATAACTACTGGGGCAGGGGACCCAGGTCACCGTCTCC TCAGAACCCAAGACACCAAAACCACAA

JLE-G6/JLE-E9, SEQ ID NO: 143
QLQLVETGGGLVKPGGSLRLSCVVSGFTFDDYRMAWVRQAPGKELEWVSSIDSWSINTYY EDSVKGRFTISTDNAKNTLYLQMSSLKPEDTAVYYCAAEDRLGVPTINAHPSKYDYNYWG QGTQVTVSSEPKTPKPQAIAGGGGSGGGGSGGGGSLQGQVQLVETGGGLVQAGGSLRLSC AASGRTFSSYSMGWFRQAPGKEREYVAAVNSNGDSTFYADSIKGRFTVSRDAAKNTVYLQ MNSLKPEDTALYYCAAVYGRYTYQSPKSYEYWGQGTQVTVSSEPKTPKPQ

SEQ ID NO: 144
CAGTTGCAGCTCGTGGAGACTGGTGGAGGCTTGGTGAAGCCTGGGGGTTCTCTGAGACTC TCCTGTGTAGTCTCCGGATTCACTTTTGATGATTATCGCATGGCTTGGGTCCGCCAGGCT CCAGGGAAGGAGCTGGAGTGGGTGTCCAGTATAGATAGTTGGAGTATCAACACATACTAT GAAGACTCCGTGAAGGGCCGGTTCACCATCTCCACAGACAACGCCAAGAATACACTGTAT CTGCAAATGAGCAGCCTGAAACCTGAGGACACGGCCGTGTATTACTGTGCAGCAGAGGAC CGCTTAGGTGTACCGACTATTAACGCCCACCCTTCAAAATATGATTATAACTACTGGGGG CAGGGGACCCAGGTCACCGTCTCCTCAGAACCCAAGACACCAAAACCACAAGCGATCGCT GGTGAGGCGGTTCAGGCGGAGGTGGCTCTGGCGGTGGCGGTTCCCTGCAGGGTCAGGTG CAGCTGGTGGAGACGGGAGGAGGATTGGTGCAGGCTGGGGGCTCTCTGAGACTCTCGTGT GCAGCCTCTGGACGCACCTTCAGTAGCTATTCCATGGGCTGGTTCCGCCAGGCTCCAGGG AAGGAGCGTGAGTATGTAGCAGCAGTTAACTCCAATGGCGACAGTACATTCTATGCCGAC TCCATTAAGGGCCGATTCACCGTCTCCAGAGACGCCGCCAAGAACACAGTCTATCTGCAA

ATGAACAGCCTGAAACCT-
GAGGACACGGCCCTTTAT-
TACTGTGCAGCTGTCTACGGTAGA  TACACT-

TACCAGTCCCCAAAATCGTATGAGTACTGGGG
CCAGGGGACCCAGGTCACCGTC
TCCTCAGAACCCAAGACACCAAAACCACAA

---

What is claimed is:

1. A recombinant binding protein that specifically binds to a *Bacillus anthracis* toxin, wherein the binding protein comprises an amino acid sequence selected from SEQ ID NO: 81, SEQ ID NO: 93, SEQ ID NO: 13, SEQ ID NO: 1, SEQ ID NO: 3, SEQ ID NO: 5, SEQ ID NO: 7, SEQ ID NO: 9, SEQ ID NO: 11, SEQ ID NO: 15, SEQ ID NO: 103, SEQ ID NO: 105, or a combination thereof.

2. The binding protein according to claim 1, which specifically binds to at least one of an Anthrax surface generated protective antigen (PA), an Anthrax lethal toxin (LT), or an Anthrax edema toxin (ET) of *B. anthracis*.

3. The binding protein according to claim 2, wherein the binding protein inhibits or prevents endocytosis of the toxin.

4. The binding protein according to claim 1, wherein the binding protein is heteromultimeric and comprises a plurality of non-identical binding regions, wherein each binding region specifically binds to a non-overlapping portion of the *Bacillus anthracis* toxin.

5. The binding protein according to claim 1, wherein the binding protein further comprises at least one of a tag epitope that is specifically bound by an anti-tag antibody and a linker that separates binding regions of the binding protein, wherein the linker comprises a peptide or a protein.

6. The binding protein of claim 1, wherein the binding protein comprises an amino acid sequence selected from SEQ ID NO: 81, SEQ ID NO: 93, SEQ ID NO: 13, or a combination thereof.

7. A composition comprising the binding protein of claim 1.

* * * * *